(12) United States Patent
Mamoun

US009611481B2

(10) Patent No.: US 9,611,481 B2
(45) Date of Patent: Apr. 4, 2017

(54) CHIMERIC POLYNUCLEOTIDES AND POLYPEPTIDES ENABLING THE SECRETION OF A POLYPEPTIDE OF INTEREST IN COMBINATION WITH EXOSOMES AND USES THEREOF

(75) Inventor: Robert Zaine El Abiddine Mamoun, St André de Sangonis (FR)

(73) Assignee: UNIVERSITE DE MONTPELLIER, Montpellier (FR)

( * ) Notice: Subject to any disclaimer, the term of this patent is extended or adjusted under 35 U.S.C. 154(b) by 0 days.

(21) Appl. No.: 13/497,779

(22) PCT Filed: Sep. 23, 2010

(86) PCT No.: PCT/FR2010/052006
§ 371 (c)(1),
(2), (4) Date: Mar. 22, 2012

(87) PCT Pub. No.: WO2011/036416
PCT Pub. Date: Mar. 31, 2011

(65) Prior Publication Data
US 2012/0321653 A1 Dec. 20, 2012

(30) Foreign Application Priority Data
Sep. 24, 2009 (FR) ..................... 09 04576

(51) Int. Cl.
*A61K 39/00* (2006.01)
*C12Q 1/68* (2006.01)
*C07K 14/435* (2006.01)
*G01N 33/574* (2006.01)
*A61K 39/395* (2006.01)
*C12N 15/62* (2006.01)

(52) U.S. Cl.
CPC ................... *C12N 15/625* (2013.01)

(58) Field of Classification Search
CPC ............ C12N 15/625; A01K 2217/075; A01K 2267/0306; A01K 2267/0362; A01K 2267/0375
USPC ....................................... 424/186
See application file for complete search history.

(56) References Cited

U.S. PATENT DOCUMENTS

2011/0268750 A1 11/2011 Mamoun et al.

FOREIGN PATENT DOCUMENTS

| WO | WO-03/016522 A2 | | 2/2003 |
|---|---|---|---|
| WO | WO03016522 | * | 2/2003 |
| WO | WO-03/076603 A2 | | 9/2003 |
| WO | WO-2004/073319 A2 | | 8/2004 |
| WO | WO2004073319 | * | 8/2004 |
| WO | WO-2009/115561 A1 | | 9/2009 |

OTHER PUBLICATIONS

De Gassart et al., Exosomal sorting of the cytoplasmic domain of the bovine leukemia virus TM env protein, Cell Biology International (2009), 33:36-48.*
De Gassart et al., Exosomal sorting of the cytoplasmic domain of bovine leukemia virus TM Env protein, 2009, Cell Biology International, 33:36-48.*
Novakovic et al., "Dileucine and YXXL Motifs in the Cytoplasmic Tail of the Bovine Leukemia Virus Transmembrane Envelope Protein Affect Protein Expression on the Cell Surface", 2004, Journal of Virology, 78z(15):8301-8311.*
Silverman et al., "Lysine residues form an integral component of a novel NH2-terminal membrane targeting Motif for Myristylated pp60(V-src)", 1992, 119(2):415-425.*
Novakovic, S. et al., "Dileucine and YXXL Motifs in the Cytoplasmic Tail of the Bovine Leukemia Virus Transmembrane Envelope Protein Affect Protein Expression of the Cell Surface," Journal of Virology, vol. 78, No. 15, pp. 8301-8311, (Aug. 2004).
De Gassart, A. et al., "Exosomal sorting of the cytoplasmic domain of bovine leukemia virus TM Env protein", Cell Biology International, vol. xx, pp. 1-13 (2008).
Reuther, G. W. et al., "Analysis of Function and Regulation of Proteins That Mediate Signal Transduction by Use of Lipid-Modified Plasma Membrane-Targeting Sequences", Methods in Enzymology, vol. 237, pp. 331-350, (2000).
Silverman, L. et al., "Lysine Residues Form an Intergral Component of a Novel $NH_2$-terminal Membrane Targeting Motif for Myristylated pp60$^{v-src}$", Journal of Cell Biology, vol. 119, No. 2, pp. 415-425, (Oct. 1992).
Zeelenberg, I.S., et al., "Targeting Tumor Antigens to Secreted Membrane Vesicles In vivo Induces Efficient Antitumor Immune Responses," Cancer Res., vol. 68, No. 4, pp. 1228-1235, (Feb. 15, 2008).
Delcayre, A., et al., "Exosome Display technology: Applications to the development of new diagnostics and therapeutics," Blood, Cells, Molecules, and Diseases, vol. 35, pp. 158-168, (2005).

(Continued)

*Primary Examiner* — Janet L Andres
*Assistant Examiner* — Barry A Chestnut
(74) *Attorney, Agent, or Firm* — Birch, Stewart, Kolasch & Birch, LLP

(57) ABSTRACT

The present invention provides a chimeric polypeptide comprising a plurality of polypeptide domains that are capable of being secreted in combination with membrane vesicles and in particular exosomes.
The invention also concerns the use of polypeptides of the invention and polynucleotides coding for these polypeptides, for the production of immunogenic compositions based on exosomes or DNA, to screen protein interactions. The present invention also concerns exploiting the properties of exosomes comprising a polypeptide of the invention and immunogenic compositions of the invention in immunology.
The present invention concerns the use of exosomes comprising a polypeptide of the invention as a diagnostic tool.
The present invention also concerns exploiting the properties of membrane vesicles and protein compositions of the invention for the prophylaxis and/or treatment of a disease due to a functional deficit, in particular to transport a protein or a nucleic acid, in particular to compensate for or make up for an enzymatic deficit, or in particular to induce a transcriptional or translational modification in the target cells or organs.

31 Claims, 28 Drawing Sheets

(56) References Cited

OTHER PUBLICATIONS

Kuate, S., et al., "Exosomal vaccines containing the S protein of the SARS coronavirus induce high levels of neutralizing antibodies," Virology, vol. 362, pp. 26-37, (2007).
Estelles, A., et al., "Exosome nanovesicles displaying G protein-coupled receptors for drug discovery," International Journal of Nanomedicine, vol. 2, No. 4, pp. 751-760, (2007).
De Gassart, A., et al., "Exosomal sorting of the cytoplasmic domain of bovine leukemia virus TM Env protein," Cell Biology International, vol. 33, pp. 36-48, (2009).
Zitvogel, L., et al., "Eradication of established murine tumors using a novel cell-free vaccine: dendritic cell-derived exosomes," Nature Medicine, vol. 4, No. 5, pp. 594-600, (May 1998).
Colino, J., et al., "Exosomes from Bone Marrow Dendritic Cells Pulsed with Diptheria Toxiod Preferentially Induce Type 1 Antigen-Specific IgG Responses in Naive Recipients in the Absence of Free Antigen[1]," The Journal of Immunology, vol. 177, pp. 3757-3762, (2006).
Chaput, N., et al., "Exosome-based immunotherapy," Cancer Immunol. Immunother., vol. 53, pp. 234-239, (2004).
Pornillos, O., et al., "Mechanisms of enveloped RNA virus budding," Trends in Cell Biology, vol. 12, No. 12, pp. 569-579, (Dec. 2002).
Raposo, G., et al., "Human Macrophages Accumulate HIV-1 Particles in MHC II Compartments," Traffic, vol. 3, pp. 718-729, (2002).
Gould, S. J., et al., "The Trojan exosome hypothesis," PNAS, vol. 100, No. 19, pp. 10592-10597, (Sep. 16, 2003).
Cann, A. J., et al., "The Region of the Envelope Gene of Human Immunodeficiency Virus Type 1 Responsible for Determination of Cell Tropism," Journal of Virology, vol. 66, No. 1, pp. 305-309, (Jan. 1992).
Delamarre, L., et al., "The HTL V-I Envelope Glycoproteins: Structure and Functions," Journal of Acquired Immune Deficiency Syndromes and Human Retrovirology, vol. 13, Suppl. 1, pp. S85-S91, (1996).
Straub, OC, et al., "Bovine immunodeficiency virus and analogies with human immunodeficiency virus," Leukemia, vol. 13, Suppl. 1, pp. S106-S109, (1999).
De Gassart, A., et al., "Exosome Secretion: The Art of Reutilizing Nonrecycled Proteins?" Traffic, vol. 5, pp. 896-903, (2004).
International Search Report for PCT/EP2009/053221.
Delcayre, A., et al., "Exosomes as novel therapeutic nanodevices," Current Opinion in Molecular Therapeutics, vol. 8, No. 1, pp. 31-38, (2006).
James H. Hurley, "Membrane binding domains"; Biochim. Biophys. Acta 1761(8): 805-811).

* cited by examiner

A
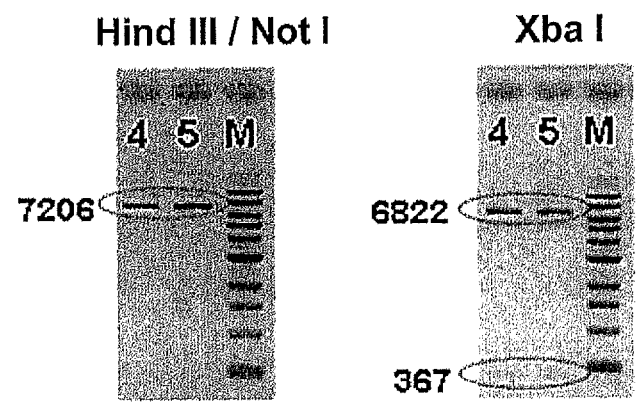
B
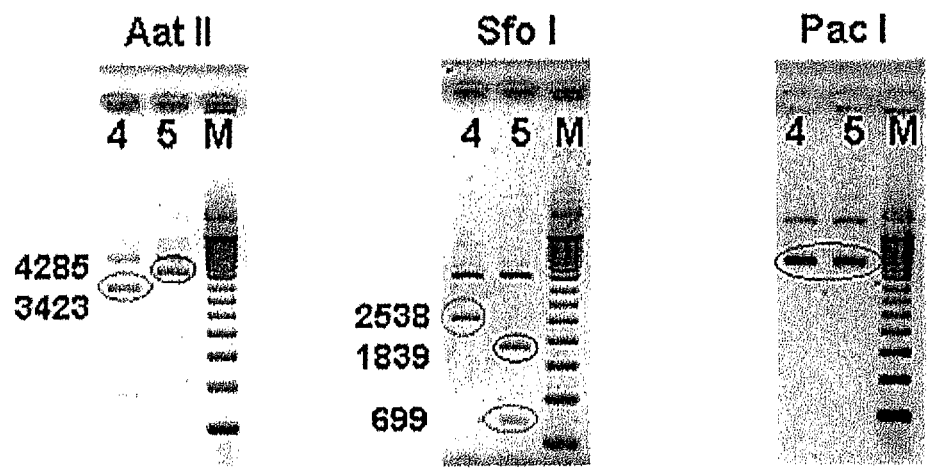
Figure 6

Src-SNAP-DCTM (SSC)

```
     EcoRI
  1 GAATTCGCCA CCATGGGCAG CAGCAAGAGC AAGCCCAAGG ACCCCAGCCA
    CTTAAGCGGT GGTACCCGTC GTCGTTCTCG TTCGGGTTCC TGGGGTCGGT
               M  G  S    S  K  S    K  P  K  D    P  S  Q      Frame 1

NheI
 51 GCGCCGCCGC AAGTCTAGAG GCCCGGGAGG CAGCGCTAGC ATGGACAAAG
    CGCGGCGGCG TTCAGATCTC CGGGCCCTCC GTCGCGATCG TACCTGTTTC
     R  R  R   K  S  R     G  P  G  G  S  A  S   M  D  K  D    Frame 1

101 ACTGCGAAAT GAAGCGCACC ACCCTGGATA GCCCTCTGGG CAAGCTGGAA
    TGACGCTTTA CTTCGCGTGG TGGGACCTAT CGGGAGACCC GTTCGACCTT
      C  E  M   K  R  T    T  L  D  S   P  L  G    K  L  E     Frame 1

151 CTGTCTGGGT GCGAACAGGG CCTGCACGAG ATCAAGCTGC TGGGCAAAGG
    GACAGACCCA CGCTTGTCCC GGACGTGCTC TAGTTCGACG ACCCGTTTCC
     L  S  G  C   E  Q  G   L  H  E    I  K  L  L    G  K  G   Frame 1

201 AACATCTGCC GCCGACGCCG TGGAAGTGCC TGCCCCAGCC GCCGTGCTGG
    TTGTAGACGG CGGCTGCGGC ACCTTCACGG ACGGGGTCGG CGGCACGACC
      T  S  A    A  D  A  V   E  V  P   A  P  A   A  V  L  G   Frame 1

251 GCGGACCAGA GCCACTGATG CAGGCCACCG CCTGGCTCAA CGCCTACTTT
    CGCCTGGTCT CGGTGACTAC GTCCGGTGGC GGACCGAGTT GCGGATGAAA
       G  P  E    P  L  M   Q  A  T    W  L  N    A  Y  F      Frame 1

301 CACCAGCCTG AGGCCATCGA GGAGTTCCCT GTGCCAGCCC TGCACCACCC
    GTGGTCGGAC TCCGGTAGCT CCTCAAGGGA CACGGTCGGG ACGTGGTGGG
      H  Q  P   E  A  I  E   E  F  P    V  P  A  L   H  H  P   Frame 1

351 AGTGTTCCAG CAGGAGAGCT TTACCCGCCA GGTGCTGTGG AAACTGCTGA
    TCACAAGGTC GTCCTCTCGA AATGGGCGGT CCACGACACC TTTGACGACT
     V  F  Q   Q  E  S  F    T  R  Q   V  L  W    K  L  L  K   Frame 1

401 AAGTGGTGAA GTTCGGAGAG GTCATCAGCT ACCAGCAGCT GGCCGCCCTG
    TTCACCACTT CAAGCCTCTC CAGTAGTCGA TGGTCGTCGA CCGGCGGGAC
     V  V  K    F  G  E   V  I  S  Y    Q  Q  L    A  A  L     Frame 1

451 GCCGGCAATC CCGCCGCCAC CGCCGCCGTG AAAACCGCCC TGAGCGGAAA
    CGGCCGTTAG GGCGGCGGTG GCGGCGGCAC TTTTGGCGGG ACTCGCCTTT
     A  G  N    P  A  A  T   A  A  V    K  T  A  L   S  G  N   Frame 1

501 TCCCGTGCCC ATTCTGATCC CCTGCCACCG GGTGGTGTCT AGCTCTGGCG
    AGGGCACGGG TAAGACTAGG GGACGGTGGC CCACCACAGA TCGAGACCGC
     P  V  P    I  L  I  P    C  H  R   V  V  S    S  S  G  A   Frame 1

551 CCGTGGGGGG CTACGAGGGC GGGCTCGCCG TGAAAGAGTG GCTGCTGGCC
    GGCACCCCCC GATGCTCCCG CCCGAGCGGC ACTTTCTCAC CGACGACCGG
     V  G  G    Y  E  G   G  L  A  V    K  E  W    L  L  A     Frame 1
```

Figure 32

```
                                          SbfI          AscI
601  CACGAGGGCC ACAGACTGGG CAAGCCTGGG CTGGGTCCTG CAGGAAGCGG
     GTGCTCCCGG TGTCTGACCC GTTCGGACCC GACCCAGGAC GTCCTTCGCC
      H  E  G  H   R  L  G   K  P  G   L  G  P   A  G  S  G      Frame 1

651  CGCGCCCCAC TTCCCTGAAA TCTCCTTCCC CCCTAAACCC GATTCTGATT
     GCGCGGGGTG AAGGGACTTT AGAGGAAGGG GGGATTTGGG CTAAGACTAA
      A  P  H   F  P  E  I   S  F  P   P  K  P   D  S  D  Y      Frame 1

701  ATCAGGCCTT GCTACCATCC GCGCCAGAGA TCTACTCTCA CCTCTCCCCC
     TAGTCCGGAA CGATGGTAGG CGCGGTCTCT AGATGAGAGT GGAGAGGGGG
      Q  A  L   L  P  S   A  P  E  I   Y  S  H   L  S  P         Frame 1

751  ACCAAACCCG ATTACATCAA CCTTCGACCG GCGCCCTAGG ACCCCCATGT
     TGGTTTGGGC TAATGTAGTT GGAAGCTGGC CGCGGGATCC TGGGGGTACA
      T  K  P  D   Y  I  N   L  R  P   A  P  *     Frame 1

801  TTCACGCACC CTCAGGCTGT GGTGGGCAC TGGCTTAGTG GAATAGTCAG
     AAGTGCGTGG GAGTCCGACA CCACCCGTG ACCGAATCAC CTTATCAGTC

NotI
851  TGTACCATCA CAAGCCTCTT CTTGCTGCCA GCACCGAGTT CGAAGCGGCC
     ACATGGTAGT GTTCGGAGAA GAACGACGGT CGTGGCTCAA GCTTCGCCGG

D-SNAP-DCTM (DSC)

```
     EcoRI
  1  GAATTCGCCA CCATGGGCAG CAGCAAGAGC AAGTCTAGAG GCCCGGGAGG
                  M  G  S   S  K  S   K  S  R  G   P  G  G       Frame 1

NheI
 51  CAGCGCTAGC ATGGACAAAG ACTGCGAAAT GAAGCGCACC ACCCTGGATA
      S  A  S   M  D  K  D  C  E  M   K  R  T    T  L  D  S     Frame 1

101  GCCCTCTGGG CAAGCTGGAA CTGTCTGGGT GCGAACAGGG CCTGCACGAG
       P  L  G   K  L  E   L  S  G  C   E  Q  G    L  H  E       Frame 1

151  ATCAAGCTGC TGGGCAAAGG AACATCTGCC GCCGACGCCG TGGAAGTGCC
      I  K  L  L  G  K  G   T  S  A   A  D  A  V   E  V  P      Frame 1

201  TGCCCCAGCC GCCGTGCTGG GCGGACCAGA GCCACTGATG CAGGCCACCG
       A  P  A   A  V  L  G   G  P  E   P  L  M   Q  A  T  A    Frame 1

251  CCTGGCTCAA CGCCTACTTT CACCAGCCTG AGGCCATCGA GGAGTTCCCT
       W  L  N   A  Y  F   H  Q  P  E   A  I  E   E  F  P       Frame 1

301  GTGCCAGCCC TGCACCACCC AGTGTTCCAG CAGGAGAGCT TTACCCGCCA
       V  P  A  L  H  H  P   V  F  Q   Q  E  S  F   T  R  Q     Frame 1

351  GGTGCTGTGG AAACTGCTGA AAGTGGTGAA GTTCGGAGAG GTCATCAGCT
       V  L  W   K  L  L  K   V  V  K   F  G  E   V  I  S  Y    Frame 1

401  ACCAGCAGCT GGCCGCCCTG GCCGGCAATC CCGCCGCCAC CGCCGCCGTG
       Q  Q  L   A  A  L   A  G  N  P   A  A  T   A  A  V       Frame 1

451  AAAACCGCCC TGAGCGGAAA TCCCGTGCCC ATTCTGATCC CCTGCCACCG
       K  T  A  L   S  G  N   P  V  P   I  L  I  P   C  H  R    Frame 1

501  GGTGGTGTCT AGCTCTGGCG CCGTGGGGGG CTACGAGGGC GGGCTCGCCG
       V  V  S   S  S  G  A   V  G  G   Y  E  G   G  L  A  V    Frame 1

551  TGAAAGAGTG GCTGCTGGCC CACGAGGGCC ACAGACTGGG CAAGCCTGGG
       *  K  E  W   L  L  A   H  E  G   H  R  L  G   K  P  G    Frame 1

SbfI            AscI
601  CTGGGTCCTG CAGGAAGCGG CGCGCCCCAC TTCCCTGAAA TCTCCTTCCC
       L  G  P  A   G  S   G  A  P  H   F  P  E  I   S  F  P    Frame 1

651  CCCTAAACCC GATTCTGATT ATCAGGCCTT GCTACCATCC GCGCCAGAGA
       P  K  P   D  S  D  Y   Q  A  L   L  P  S   A  P  E  I    Frame 1

701  TCTACTCTCA CCTCTCCCCC ACCAAACCCG ATTACATCAA CCTTCGACCG
       Y  S  H  L  S  P   T  K  P  D   Y  I  N   L  R  P        Frame 1

751  GCGCCCTAGG ACCCCCATGT TTCACGCACC CTCAGGCTGT GGTGGGGCAC
       A  P  *   Frame 1

801  TGGCTTAGTG GAATAGTCAG TGTACCATCA CAAGCCTCTT CTTGCTGCCA

NotI
851  GCACCGAGTT CGAAGCGGCC GC
```

Figure 33

CHIMERIC POLYNUCLEOTIDES AND POLYPEPTIDES ENABLING THE SECRETION OF A POLYPEPTIDE OF INTEREST IN COMBINATION WITH EXOSOMES AND USES THEREOF

This application is the National Phase under 35 U.S.C. §371 of PCT International Appl. No. PCT/FR2010/052006 which has an International filing date of Sep. 23, 2010, which claims priority to French Application No. 09/04576 filed on Sep. 24, 2009.

The invention relates to chimeric polynucleotides and polypeptides enabling the secretion of a polypeptide of interest in association with exosomes, and to their use in particular for the production of immunogenic compositions based on chimeric polypeptides, DNA or exosomes, for the screening of protein interactions, or for the transport of proteins or nucleic acids.

The present invention provides a chimeric polypeptide capable of being secreted in association with exosomes when it is expressed in appropriate eukaryotic cells, said chimeric polypeptide comprising a plurality of polypeptide domains.

The invention also concerns a membrane vesicle, in particular an exosome, which comprises a polypeptide of the invention, an immunogenic composition based on such exosomes and a method for the production of such exosomes.

The invention also provides a polynucleotide coding for a polypeptide of the invention and an immunogenic composition comprising it, in particular a DNA vaccine comprising it.

The present invention also concerns exploiting the properties of the membrane vesicles and immunogenic compositions of the invention for prophylaxis and/or treatment of an infection by a pathogenic agent, a pathogenic organism, a tumor antigen or a cytoplasmic agent, in particular to elicit or promote, in vivo, in a host (human or non-human), a humoral and/or cellular response against a virus, a bacterium, a parasite or a tumor.

The present invention also concerns the use of exosomes comprising a polypeptide of the invention as a diagnostic tool.

The present invention also concerns exploiting the properties of the membrane vesicles and protein compositions of the invention for the prophylaxis and/or treatment of a disease due to a functional or metabolic deficit, in particular to transport a protein or a nucleic acid, in particular to compensate for or make up for an enzymatic deficit, or in particular to induce a transcriptional or translational modification in the pertinent target cells or organs, or to modify the cellular metabolism.

The present invention also relates to the use of membrane vesicles of the invention for the production of antibodies directed against the peptide or the polypeptide of interest.

The present invention also relates to the use of membrane vesicles of the invention for the study of interactions between proteins and for the study of molecules interacting with the proteins of interest.

Exosomes have the shape of small spheres delimited by a lipid bilayer. Such membrane vesicles are secreted naturally by various types of cells, in particular by epithelial cells, tumor cells and certain cells of the immune system (mastocytes, T and B lymphocytes, dendritic cells, in particular Langerhans cells). Exosomes are distinguished from other membrane vesicles secreted by cells by their small size (50 to 100 nm in diameter) and by their membrane protein composition (adhesion, transport, signal transduction molecules and molecules of the major histocompatibility complex, inter alia).

In particular, exosomes can act as internal vesicles of multivesicular endosomes (in particular late endosomes) secreted by the cell during fusion of those endosomes with the plasma membrane; multivesicular endosomes are generally involved in the transport of molecules in the lysosome compartments (protein degradation pathway), but in certain cells such as reticulocytes and certain antigen-presenting cells, they can be directed to the plasma membrane with which they fuse to liberate exosomes into the extracellular medium.

Previous studies have shown that exosomes are capable of inducing humoral and/or cellular immune responses (Delcayre et al, 2002). Exosomes are considered to be vectors for antigens that are capable of directly stimulating T lymphocytes in vitro in an antigen-specific manner. Indeed, exosomes secreted by dendritic cells express molecules of the major histocompatibility complex class I and II. (MHC). The functional peptide/MHC complexes carried by the exosomes are transferred from one dendritic cell to another that has never encountered the antigen from which the peptides associated with the molecules of the MHC molecules derive. By stimulating naive dendritic cells step by step, the secreted exosomes having an antigenic peptide on their surface contribute to amplification of the specific T CD4 and T CD8 response (Delcayre and Le Pecq, 2006). As an example, when loaded with tumor peptides and injected into mice, those exosomes are capable of promoting a strong immune response and of causing pre-established solid tumors to regress (Zitvogel et al, 1998).

Exosomes are capable of displaying exogenic antigens either in the form of whole native proteins or in the form of peptides associated with MHC I and II molecules (Colino and Snapper 2006). Displaying antigen at the surface of exosomes is similar to displaying at a membrane of a cell or an enveloped virus. However, exosomes are neither living nor infectious, and so they have the advantage of being able to be manipulated as an ordinary product without having to take confinement precautions, in contrast to a virus. Thus, exosomes can be used to present peptides or antigenic polypeptides for the purposes of immunization. This technique, known as "exosome display", does not necessarily require the direct display of antigen by the MHC (Chaput et al, 2004). However, the development of this innovative vaccination technique assumes that an effective molecular "tool" is available to enable targeting of antigenic proteins with exosomes. But such a "tool" has not as yet been described.

The study of retroviruses, and more particularly the human immunodeficiency virus (HIV), has revealed their capacity to hijack the cellular machinery for the biogenesis of multivesicular endosomes in order to bud to the plasma membrane (Pornillos et al, 2002). Such viruses can also use that machinery at the endosomal membrane, its normal functional site (Raposo et al, 2002). Thus, according to the "Trojan Exosomes" (Gould et al, 2003) hypothesis, such viruses use the pre-existing exosome biogenesis pathway for the formation of viral particles.

The envelope of retroviruses is constituted by the external envelope glycoprotein (SU) and the transmembrane glycoprotein (TM). These envelope glycoproteins derive from cleavage of the precursor protein known as ENV. Expression of the env gene results in synthesis of the envelope glycoproteins of the retroviruses, in the form of a protein precursor that passes through the Golgi before reaching the portion of the membrane (endosomal or plasma) that will become the viral envelope during budding of the virions. During this passage, this oligomeric precursor is glycosylated and cleaved into surface glycoproteins (SU) and transmembrane (TM) glycoproteins. The proteins SU and TM remain associated and are anchored in the vesicular or cellular membrane via a hydrophobic transmembrane helix of the TM protein.

The TM glycoprotein of retroviruses is multifaceted due to the association of its external, transmembrane and cytoplasmic (CD™) domains, which form the only protein of the retroviruses enabling communication either side of the membranes of the virus and the infected cell (Cann et al, 1992; Delamarre et al, 1996). In particular, it is involved in the phenomenon of penetration of the virus into the target cell, causing fusion between viral and cellular membranes. Further, during its intracellular journey, the TM protein is capable of having an influence on sorting, outcome, targeting and budding of viral particles by interactions with the cytoskeleton and also with the ubiquitation and budding machinery (Cann et al, 1992; Delamarre et al, 1996; Straub and Levy, 1999).

A previous study suggests that the cytoplasmic domain of the TM protein of two retroviruses, the bovine leukemia virus (BLV) and Human Immunodeficiency Virus, can induce addressing and secretion of a recombinant protein in exosomes (De Gassart et al, 2004; 2009). Cells from the K562 line (an erythroleukemic cell line of human origin), which secrete exosomes constitutively, were transfected with retroviral vectors that enabled expression, in a eukaryotic system, of two types of chimeric protein: (i) a chimera comprising the extracellular domain of the murine CD8 protein and transmembrane and cytoplasmic domains of the TM glycoprotein of BLV (TM-BLV/CD8 chimera; De Gassart et al, 2004; 2009), and (ii) a chimera comprising the extracellular and transmembrane domains of the murine CD8 protein and the cytoplasmic domain of the TM protein of HIV (TM-HIV/CD8 chimera; De Gassart et al, 2004). The two chimeras are expressed both in transfected K562 cells and in exosomes secreted by those cells. In particular, expression of the chimeric TM-BLV/CD8 protein in cells from the K562 line disappeared rapidly after transit in the trans-Golgian network and the late endosomal compartments to fetch up in the exosomes secreted by those cells. It appears that the chimera comprising the cytoplasmic domain of the TM protein of BLV is more strongly addressed to exosomes than the chimera comprising the cytoplasmic domain of the TM protein of HIV.

However, as will be proven by the results presented in the example section of the present application, exosomes carrying the chimeric construct TM-BLV/CD8 described by De Gassart et al are only effectively produced in cells from the K562 line, and are few or are not effectively produced in other cell types such as cells from the HEK293 line.

The present invention concerns novel chimeric polypeptides having addressing properties in the exosomes. The chimeric polypeptides of the invention comprise only cytosolic domains and/or nuclear domains and are anchored in the membrane of the membrane vesicles, in particular exosomes, without being inserted into the lipid bilayer of a vesicular or cellular membrane, nor do they pass through that lipid bilayer. The present application also describes other chimeric polypeptides that are capable of being anchored in the membrane of membrane vesicles, in particular exosomes. These additional chimeric polypeptides comprise one or more membrane domain(s), in particular at least one transmembrane domain. The anchoring function in the vesicular or cellular membranes of these additional chimeric polypeptides is provided by their membrane domain(s), which enable them to be inserted into the lipid bilayer of a vesicular or cellular membrane and if necessary of passing through it in part.

In accordance with a particular aspect of the invention, these additional chimeric polypeptides are used jointly with the chimeric polypeptides of the invention.

The chimeric polypeptides described in this application and in particular the chimeric polypeptides of the invention are in particular distinguished from those described in the prior art, especially those described by De Gassart et al, in that they can much more efficiently address a peptide or a polypeptide of interest to the exosomes produced by the cells of the HEK293 line, and thus very greatly amplify (10 to 100 times) the production of exosomes comprising said peptide or polypeptide of interest. Further, in contrast to the constructs described by De Gassart et al, which can only be used effectively in cells from the K562 line, these polypeptides can be addressed to exosome membrane and secreted in association with membrane vesicles, in particular exosomes produced by various cell types, in particular HEK293 cells or T lymphocytes or B lymphocytes, and not solely by cells from the K562 line. The present invention in particular enables the production of large quantities of membrane vesicles, in particular exosomes, which can be used as research tools and also in diagnostics, in medical applications and in particular for immunization, in particular vaccination.

Such membrane vesicles (in particular exosomes) could also be produced in vivo by a human or non-human host (in particular a human or non-human mammal or a bird), for example to immunize them, and in particular to vaccinate them, by administration to that host of a composition, in particular an immunogenic composition the active principle of which is a polynucleotide coding for a polypeptide of the invention, in particular an immunogenic composition based on DNA, and more particularly a DNA vaccine, or an immunogenic composition the active principle of which consists of membrane vesicles (in particular exosomes) comprising a polypeptide of the invention.

In a first aspect, the present invention provides a chimeric polypeptide characterized in that it comprises or consists of the following domains:

(i) a peptide or polypeptide of interest;
(ii) an infra-membrane targeting domain; and
(iii) a cytoplasmic domain (CD) of a membrane protein, enabling, in eukaryotic cells, addressing of said chimeric polypeptide to membrane vesicles, in particular to exosome-forming vesicles, and/or to the cellular compartment(s) involved in the formation of the membrane vesicles, and in particular exosome-forming vesicles, or a mutated derivative of said CD domain, said mutated derivative being defined by substitution, deletion and/or insertion of one or more residue(s) in the sequence of a reference CD domain and said mutated derivative conserving said addressing capacity of the CD domain, the CD domain or its mutated derivative comprising at least one motif YxxL and a motif PxxP, in which x represents any residue;

it being understood that the domains present in the chimeric polypeptide, in particular the domains (i), (ii) and (iii), are cytosolic or nuclear domains (for example, the domains (i) and (iii) are cytosolic) and that said chimeric polypeptide is deprived of a signal peptide for importation into the endoplasmic reticulum. The term "residue" as used in the present application refers to an amino acid residue.

These residues are indicated by using the single letter abbreviated code, for example, Y for a tyrosine residue, L for a leucine residue, P for a proline residue and x for any residue.

The motif PXXP in the CD domain or its mutated derivative is preferably the motif PSAP (SEQ ID NO. 88) or the motif PTAP (SEQ ID NO. 89).

The chimeric polypeptide of the invention is in particular capable of being secreted in combination with membrane vesicles, in particular with exosomes, when it is expressed in appropriate eukaryotic cells. When exosomes comprising the polypeptide of the invention are secreted, the peptide or the polypeptide of interest is included (entirely) in the cytosolic fraction of these exosomes. This in particular shows that the chimeric polypeptide of the invention is free of signal peptide which would enable importation into the endoplasmic reticulum.

In accordance with a particular embodiment, the domains (i) to (iii) are positioned in succession in the following order, from the N-terminal end to the C-terminal end in the chimeric polypeptide of the invention: infra-membrane targeting domain (ii)—peptide or polypeptide of interest (i)—CD domain or its mutated derivative (iii).

Alternatively, the domains (i) to (iii) may be positioned in a different order, for example in the following order: infra-membrane targeting domain (ii)—CD domain or its mutated derivative (iii)—peptide or polypeptide of interest (i). One or the other of domains (ii) or (iii) or the two domains (ii) and (iii) may also be positioned between two identical or different domains of type (i); they may also be inserted within one domain (i), for example in the order N-terminal of (i)-(ii) [or (iii)]-(iii) [or (ii)]-remaining C-terminal fragment of (i).

The term "chimeric" as used here designates a polypeptide that combines a plurality of domains of at least two different types as regards their function and/or their cell location, at least two of said domains deriving from distinct molecules, in particular deriving either from different proteins of the same species or different species or from the same protein of different species.

A "chimeric polypeptide" as defined in the present application may be the expression product of a recombinant polynucleotide and may be expressed by the recombinant pathway in a host cell. Said chimeric polypeptide is thus a fusion polypeptide, for example.

The term "domain" of a protein or of a polypeptide means a region having a functional and/or cell localization property for said protein or said polypeptide.

The term "infra-membrane targeting domain" or "membrane addressing domain" or "membrane recruitment domain" (or for association with cellular and vesicular membranes) denotes, in the present application, a domain that in a cell, and in particular in a eukaryotic cell (for example an exosome-producing cell), is capable of anchoring to a cellular membrane and/or a vesicular membrane without being inserted into said membrane or said membrane(s), anchoring to the membrane or to the membranes being accomplished by means of one or more anchoring molecule(s) (said domain being capable of binding said anchoring molecule or molecules) and/or by interactions (in particular electrostatic interactions) between said infra-membrane targeting domain and said membrane or membranes. In a particular embodiment, said domain is capable, in a cell and in particular in a eukaryotic cell (for example an exosome-producing cell), of binding to or interacting with the internal face (i.e. the cytoplasmic face) of the plasma membrane and/or membrane vesicles, via one or more anchoring molecule(s) and/or by interactions (in particular electrostatic interactions).

The term "infra-membrane targeting", "membrane addressing" or "membrane recruitment", when it is applied to domain (ii) present in the chimeric polypeptide of the invention, implies an ability to interact (via one or more anchoring molecule(s) and/or by interactions, in particular electrostatic interactions) with a cellular membrane (in particular the plasma membrane) and/or a vesicular membrane. If necessary (but not necessarily), this term also implies an active uptake cellular charge in order to bring said domain (ii) and, as a consequence, a chimeric polypeptide comprising said domain (ii), close to a cellular membrane (in particular the plasma membrane) or vesicular membrane, such that interactions with said membrane become possible.

The infra-membrane targeting domain is sufficient to enable anchoring of the chimeric polypeptide of the invention to the lipid bilayer of cellular or vesicular membranes (via one or more anchoring molecule(s) and/or by interactions). Thus, because of its presence in the chimeric polypeptide of the invention, the infra-membrane targeting domain enables a chimeric polypeptide of the invention expressed in a cell, and in particular a eukaryotic cell, to be anchored to (occasionally said to be "anchored in") a cellular or vesicular membrane, without said polypeptide being inserted into said membrane. In a preferred embodiment of the invention, the infra-membrane targeting domain provides the chimeric polypeptide of the invention with the property of binding (via one or more anchoring molecule(s) and/or by interactions, in particular electrostatic interactions) to the vesicular and cellular membrane and in particular to the internal face of the plasma membrane and membrane vesicles.

In accordance with a particular embodiment of the invention, the infra-membrane targeting domain comprises 5 to 40 residues, preferably 8 to 25 or 12 to 25 residues and more preferably 14 to 25 or 16 to 23 residues, for example 8, 9, 10, 11, 12, 13, 14, 15, 17, 18, 19, 20, 21, 22, 23, 24, or 25 residues.

The term "anchoring molecule" as used in the present application means any molecule that is capable of being inserted into the lipid bilayer (in particular into at least one sheet of the lipid bilayer) of a cellular or vesicular membrane and in particular a lipid or a lipid molecule (i.e. a molecule comprising one or more lipids); the infra-membrane targeting domain and the chimeric polypeptide of the invention are thus said to be "lipid anchored".

In accordance with a particular embodiment of the invention, the anchoring molecule in the context of the invention comprises or consists of one or more lipid(s), said lipid or lipids comprising a hydrophobic carbon chain that can embed itself into the lipid bilayer of a cellular or vesicular membrane.

In accordance with a particular embodiment of the invention, the lipid(s) present in the anchoring molecule is (are) selected from fatty acids, for example from myristic and palmitic acids, and the isoprenoids, in particular geranylgeranyls and farnesyls.

In accordance with a particular embodiment of the invention, the anchoring molecule or molecules is (are) linked to the infra-membrane targeting domain present in the chimeric polypeptide of the invention via a covalent bond.

In accordance with a particular embodiment of the invention, the "infra-membrane targeting domain" enables the chimeric polypeptide of the invention to be anchored to the lipid bilayer via one or more fatty acid(s), in particular one or more fatty acid(s) selected from myristic acids, palmitic acids and gernayl-geranyls, and/or via a peptide or a peptide structure capable of interacting with one or more lipid(s) or lipid motif(s) present in a lipid bilayer, in particular with a phospholipid. Thus, the chimeric polypeptide of the invention is anchored to the cellular and vesicular membranes without being inserted into said membranes.

In a preferred embodiment, this domain is sufficient to bind a fatty acid and in particular a myristic acid, a palmitic acid or a geranyl-geranyl. Said binding may in particular be to a G (for example in the case of a myristic acid), C or S residue of the infra-membrane targeting domain. In particular, it may be an amide or thioester bond. The fatty acid, in particular myristic acid, may bind to the infra-membrane targeting domain via a covalent bond.

In accordance with a particular embodiment of the invention, the infra-membrane targeting domain comprises or consists of a peptide or a peptide structure (i.e. a structure comprising one or more amino acid residue(s) and preferably one or more concatenation(s) of at least two consecutive amino acid residue(s)) capable of interacting with one or more lipid(s) (in particular one or more fatty acid(s)) or with one or more lipid motif(s) (in particular one or more lipid motif(s) comprising or consisting of one or more fatty acid(s)) present in a lipid bilayer, in particular with a phospholipid.

The infra-membrane targeting domain and the peptide or the polypeptide of interest of the chimeric polypeptide of the invention may or may not be derived from the same entity, in particular from the same protein.

In a preferred embodiment, the infra-membrane targeting domain is that of an extrinsic membrane protein or is a mutated derivative of an infra-membrane targeting domain of an extrinsic membrane protein.

In a preferred embodiment, the "infra-membrane targeting domain" comprises or consists of a consensus sequence enabling attachment, for example by acylation or by prenylation, of a fatty acid and in particular myristic acid, a palmitic acid or a geranyl-geranyl.

Said consensus sequence may comprise or consist of the following sequence: M-G-$X_1$-$X_2$-$X_3$-S/C (in which $X_1$, $X_2$, and $X_3$ independently designate any residue), in particular in the case in which it enables attachment of a myristic acid. When a fatty acid binds to this consensus sequence, it is generally to the G residue, for example in position 2.

In accordance with a particular embodiment,
$X_1$ is selected from C, S and L; and/or
$X_2$ is selected from S, I, V, M and L; and/or
$X_3$ is selected from K, Q, H, F, C and S.

When said consensus sequence enables the attachment of a myristic acid, it is preferably localized in the N-terminal position (for example in position 2) in the infra-membrane targeting domain, and thus in the polypeptide of the invention.

In a preferred embodiment, the "infra-membrane targeting domain" comprises a plurality of basic amino acid residues, in particular a plurality of residues selected from K, R and H. The term "a plurality of" as used here means at least two, and preferably at least three, for example, two, three, four, five or more than five.

These amino acids may in particular be involved in interactions with the lipids of the cellular or vesicular membranes, in particular with choline (for example with phosphatidyl choline), and thus can enhance the infra-membrane targeting affinity for these membranes.

The basic amino acids of the infra-membrane targeting domain may be localized in the consensus sequence described above and/or outside this consensus sequence.

Thus, in accordance with a particular embodiment of the invention, the infra-membrane targeting domain of the invention:

comprises or consists of a sequence selected from the following sequences: M-G-x-x-K-S/C-K-x-K and M-G-x-x-K-S/C-K-x-K-x-x-x-x-R-R-R, in which x designates any residue); such a sequence may, for example, enable the attachment of a myristic acid (for example in position 2); or consists of a mutated derivative of this sequence, said mutated derivative conserving the capacity of this domain to become anchored in the lipid bilayer of a cellular membrane.

The infra-membrane targeting domain may in particular originate from a protein of the Src protein family, in particular from a protein selected from the proteins Src, Yes, Lyn, Fyn, Lck, Blk, Fgr, Hck and Yrk (Resh, 1994), and more particularly from the N-terminal portion of one of these proteins. As an example, this domain may originate from the proteins c-Src or v-Src (preferably c-Src). This domain may, for example, comprise or consist of the 15, 16, 17, 18, 19, 20, 21, 22, 23, 24 or 25 N-terminal amino acids of one of these proteins, and in particular the protein Src.

Alternatively, the infra-membrane targeting domain may originate from other acylated proteins, in particular proteins from viral capsids, for example the MA protein of the human immunodeficiency virus (HIV), or filovirus proteins.

Thus, the infra-membrane targeting domain may originate from a Src protein, and in particular comprise or consist of the following sequence: M-G-S-S-K-S-K-P-K-D-P-S-Q-R-R-R (SEQ ID NO. 104) or M-G-S-S-K-S-K-P-K-D-P-S-Q-R-R-R-K-S-R-G-P-G-G (SEQ ID NO. 105) or consist of a mutated derivative of the domain with sequence M-G-S-S-K-S-K-P-K-D-P-S-Q-R-R-R or M-G-S-S-K-S-K-P-K-D-P-S-Q-R-R-R-K-S-R-G-P-G-G.

The term "originate from a particular protein" as used in the present application indicates that the pertinent peptide or polypeptide comprises or consists of that particular protein or a fragment of said particular protein or a mutated derivative of said protein or a fragment by substitution or deletion of amino acids.

Among other peptides or peptide structures that are capable of interacting with one or more lipid(s) or a particular lipid motif, which can be used to target the internal face of cellular or vesicular membranes, the following can be cited: FYVE domains (Hurley, J H; 2006). Thus, in accordance with a particular embodiment of the invention, the infra-membrane targeting domain comprises or consists of one or more FYVE domain(s).

The expression "membrane vesicle" as used in the present application means any vesicle composed of a lipid bilayer enclosing a cytosolic fraction such as that produced by eukaryotic cells. This expression in particular includes vesicles secreted into the extracellular space, i.e. exosomes.

The term "exosomes", as used in the present application means nanovesicles of cellular membranes as defined above. These exosomes may be purified from supernatants obtained from cell cultures by differential centrifuging, ultrafiltration or adsorption onto a support or by any other method, as illustrated in the examples.

The expression "secreted in combination with membrane vesicles, in particular with exosomes" as used in the present application means that a chimeric polypeptide of the invention and/or at least one of its degradation products is secreted in the extracellular space, not in the soluble form in this extracellular space, but in the form that is anchored to the internal face of the membrane of the membrane vesicles, in particular exosomes.

Since the chimeric polypeptide of the invention does not comprise a signal peptide for importation into the endoplasmic reticulum, it is a permanent resident of the cytosol or nucleus (it remains localized in the cytosol or in the nucleus) and will thus not be integrated into the membrane nor at the surface of a membrane vesicle and in particular of an exosome secreted by an exosome-producing cell, but inside (i.e. in the lumen) of that membrane vesicle. In addition, that polypeptide is addressed to membrane and anchored to the membrane of the membrane vesicles, in particular exosomes, via a peptide that is capable of interacting with one or more lipids) or a lipid motif present in the internal layer of a lipid bilayer, in particular a phospholipid or, as is preferable via one or more fatty acid(s) (in particular one more fatty acid(s) selected from myristic acid, palmitic acids and geranyl-geranyls), which interact with the infra-membrane targeting domain.

This (these) fatty acid(s) may be attached in a co-translational manner to enable the chimeric polypeptide produced in the cytoplasm of a cell to anchor itself post-translationally in the cellular or vesicular membranes.

In accordance with a particular embodiment, the chimeric polypeptide of the invention is produced with and is integrated into the exosomes before they leave the cell.

Secretion of a peptide or of a polypeptide in association with the membrane vesicles (in particular exosomes) in particular requires (1) addressing said peptide or polypeptide to the location(s) for formation of the membrane vesicles, in particular exosomes, and (2) vesicular budding from the membrane in which said peptide or polypeptide is anchored.

The term "addressing," also termed "sorting", "needling" or "intracellular routing" as used in the present application refers to the process that enables a polypeptide, the synthesis of which starts in the cytosol, to be directed to and reach the compartments involved in budding of membrane vesicles, in particular exosome-forming vesicles, and/or to reach the membrane vesicles, in particular exosome-forming vesicles.

The term "secretion" as used in the context of the invention, designates the process by which membrane vesicles, also termed "exosomes", are secreted, i.e. released into the extracellular space, from one or more cell(s). This process may in particular occur when multivesicular endosomes fuse with the plasma membrane of a cell, thereby releasing the membrane vesicles they contain outside the cell.

As illustrated in the examples below, a test that can be used to demonstrate the addressing properties and secretion properties of a chimeric polypeptide as defined in the present application consists of verifying that said chimeric polypeptide and/or its degradation products are indeed associated with membrane vesicles (in particular exosomes) when said polypeptide is expressed in the appropriate eukaryotic cells.

An "appropriate" eukaryotic cell is advantageously a eukaryotic cell comprising internal secretion vesicles, which can be cultured, which is capable of exocytosis, which is genetically modifiable and preferably has internal vesicles that can be secreted under the effect of an external stimulation. In particular, it is a mammalian cell and more particularly a cell of human origin or a cell with a non-human mammalian origin. It may also be a primary culture or immortalized line. Such "appropriate" eukaryotic cells in particular include eukaryotic cells that are naturally capable of producing exosomes, in particular mastocytes, T and B lymphocytes and dendritic cells (for example Langerhans cells) or cells derived from these cell types, as well as eukaryotic cells or eukaryotic cell lines modified by genetic engineering so as to render them capable of secreting exosomes.

The term "lipid bilayer" designates the basic structure of the plasma membrane and any biological membrane, i.e. any assembly of amphiphilic lipids in a double sheet (or double layer) separating a cell or a vesicle from its environment and delimiting the cytoplasm of a cell or a vesicle, or delimiting the organites inside the cytoplasm. This term thus encompasses any membrane of the cell, i.e. both the plasma membrane and the membranes of the various intracellular compartments, in particular those of the endoplasmic reticulum, those of the Golgi apparatus, or that of the membrane vesicles, for example that of the exosomes or endosomes.

The term "cytoplasmic domain" (CD) as used in the present application means a particular cytoplasmic domain that is capable of being addressed to membrane vesicles, in particular to exosome-forming vesicles, or to cellular compartment(s) involved in the formation of the membrane vesicles, and in particular exosome-forming vesicles in eukaryotic cells; this domain may then be secreted into the extracellular space in association with the exosomes, when it is expressed in appropriate eukaryotic cells. Thus, when it is integrated into a chimeric polypeptide comprising a peptide or polypeptide of interest, this domain enables said chimeric polypeptide to be addressed to membrane vesicles and/or to their formation location(s) and in particular enables said chimeric polypeptide to be addressed to the membrane of membrane vesicles, such that said polypeptide can be secreted in association with the membrane vesicles (in particular exosomes) by a cell, in particular an appropriate eukaryotic cell.

A "mutated derivative" of a domain in the context of the present application refers to any polypeptide or peptide that is modified with respect to the original or reference domain, provided that this mutated derivative conserves the function normally associated with this domain: this function is, for example, the capacity for addressing to membrane vesicles (and in particular to the exosomes) normally attached to the reference CD domain, the function of anchoring to a lipid bilayer normally attached to the infra-membrane targeting domain and, for the additional chimeric peptides, the function of insertion into and anchoring in a lipid bilayer normally involving a membrane domain and in particular the capacity to pass in its entirety through and be anchored in a lipid bilayer normally involving a transmembrane domain. Such a mutated derivative may thus, for example, correspond to a fragment composed of contiguous residues of said original domain or reference domain (this derivative being obtained in particular by deletion and optional substitution of one or more residue(s) into the original sequence) or, in contrast, to a polypeptide with a larger size than the original or reference domain, in particular a polypeptide comprising the original or reference domain (this derivative being obtained by insertion of one or more residue(s) into the original sequence).

In accordance with a particular embodiment, the "mutated derivative" differs from the original or reference sequence by substitution of at least one residue, preferably one, two, three, four, five or even more than five residue(s), which may or may not be consecutive, into the original domain sequence, these substitutions possibly being conservative, semi-conservative or non-conservative, and/or by deletion of at least one residue, preferably one, two, three, four, five or even more than five residue(s), which may or may not be consecutive, and/or by insertion of at least one residue, preferably one, two, three, four, five or even more than five residues, which may or may not be consecutive, into the original domain sequence.

The sequence for this "mutated derivative" may have at least 60% or 70%, in particular at least 80%, 90% or 95% similarity or identity with the original domain from which it is derived, with reference to the complete sequence of the original domain. The term "percentage identity" as used in the present application means the number of identical residues compared with the total number of residues of the peptide or polypeptide being studied. The "percentage similarity" defines the number of identical or chemically similar residues compared with the total number of residues of the peptide or polypeptide being studied. The percentage identity or similarity is determined by aligning the two sequences to be compared and using the Needleman and Wunsch algorithm, which is used to produce a global alignment between two sequences. The percentage similarity or identity is then calculated on the basis of the whole length of these two sequences.

In accordance with a particular embodiment, the CD domain or its mutated derivative comprises two or three motifs YxxL, in which x represents any residue. The motif or one of the motifs YxxL present in the CD domain may, for example, be the motif YINL (SEQ ID NO. 91) or YSHL (SEQ ID NO. 97).

In accordance with a particular embodiment, the CD domain or its mutated derivative comprises a motif DYxxL, in which x represents any residue. An example that is illustrated in the experimental section and that may be cited is the motif DYINL (SEQ ID NO. 93).

Alternatively or in a complementary manner, the CD domain comprises at least one motif equivalent to a motif YxxL or to a motif DYxxL, for example a motif YxxF or DYxxF respectively, in which x represents any residue. As an example, the receptor for transferrin, which is a cell protein, comprises a domain YxxF.

The description of the present application, made with reference to the domain YxxL in general or as illustrated by the particular sequences, is also valid for the domains DYxxL or DYxxF, defined in general terms or having specific sequences derived from the given examples of motifs.

In a preferred embodiment, the CD domain or its mutated derivative further comprises two, three or four motif(s) PxxP, in which x represents any residue, at least one of these motifs PxxP being the motif PSAP (SEQ ID NO. 88) or PTAP (SEQ ID NO. 89). In a particular embodiment of the invention, the motif PxxP of the CD domain or of its mutated derivative is PSAP or PTAP (more preferably PSAP) and the motif YxxL is YINL or YSHL.

In a particular embodiment, the motif YxxL of the CD domain (for example the motif YINL or YSHL), or where one of the motifs is YxxL, is localized in the C-terminal position with respect to the motif PxxP (for example the motif PSAP).

In a particular embodiment, the motif YxxL of the CD domain (for example the motif YINL or YSHL) is localized in the N-terminal position with respect to the motif PxxP (for example the motif PSAP).

Proteins having a CD domain comprising at least one motif YxxL in particular include cellular proteins and viral proteins. These viral proteins are in particular the proteins of enveloped viruses, in particular the TM glycoproteins of enveloped viruses and in particular of retroviruses.

In accordance with a particular embodiment, the CD domain is that of a TM protein of bovine leukemia virus (BLV). This retrovirus, which forms part of the Oncovirinae (it is an oncovirus), induces, in cattle, proliferation of B cells that may cause leukemia.

The CD domain of the TM protein of BLV is composed of 58 residues, and has the sequence SEQ ID NO. 6. The CD domain of the chimeric polypeptide of the invention or its imitated derivative thus corresponds either to the domain with sequence SEQ ID NO. 6, or to a mutated derivative of the domain with sequence SEQ ID NO. 6.

In a particular embodiment of the invention, the mutated derivative of the CD domain is a fragment of native CD domain essentially constituted by a sequence of amino acids extending from the motif PSAP (or PTAP) to a motif YxxL (for example YINL or YSHL) that, in a particular embodiment, follows it at the C-terminal portion. If necessary, one or more amino acid residues naturally present in the CD domain, between these two motifs, is (are) substituted or deleted.

In accordance with a particular embodiment, the CD domain of the chimeric polypeptide of the invention or its mutated derivative, in particular the mutated derivative of the CD domain, is deprived of the sequence KCLTSRLLKLLRQ. Thus, the mutated derivative of the CD domain may differ from the original CD domain in that its sequence is deprived of the sequence KCLTSRLLKLLRQ.

Further, or alternatively, the sequence of the mutated derivative of the CD domain may have at least 60% or 70%, in particular at least 80%, 90% or 95% similarity or identity with the sequence of the original CD domain deprived of the concatenation KCLTSRLLKLLRQ.

It may also be preferable for the CD domain or its mutated derivative, and in particular its mutated derivative, to be deprived of the sequence PC and/or of the sequence CP. In accordance with a particular embodiment, said CD domain or its mutated derivative, in particular its mutated derivative, is in particular deprived of the sequence PCP. Thus, if the original CD domain contains a sequence PCP, its mutated derivative may in particular be obtained by deleting the cysteine residue of said sequence PCP from the sequence for the original CD domain, or by substituting it with another residue, preferably a non-palmitylable residue, for example an alanine residue.

In accordance with a particular embodiment, the CD domain or its derivative is deprived of both the sequence PCP and the concatenation KCLTSRLLKLLRQ.

By way of example, the mutated derivative of the CD domain of the TM protein of BLV may comprise or consist of the sequence SEQ ID NO. 8, which corresponds to the sequence SEQ ID NO. 6 from which the 13 N-terminal residues have been deleted.

Again by way of example, the sequence of the mutated derivative of the TM protein of BLV may differ from the sequence of the CD domain of the TM protein of BLV by substitution of at least one residue, preferably one, two, three, four, five, or even more than five residue(s), which may or may not be consecutive, and/or by deletion and/or insertion of at least one residue, preferably one, two, three, four, five, or even more than five residue(s), which may or may not be consecutive, in the sequence for said domain corresponding to the sequence SEQ ID NO. 8.

Again by way of example, the sequence for the mutated derivative of the CD domain of the TM protein of BLV (CD domain with sequence SEQ ID NO. 6) may have at least 60% or 70%, in particular at least 80%, 90% or 95% similarity or identity with the sequence SEQ ID NO. 8. Preferably, the sequence for said mutated derivative in particular conserves the motif YINL, YSHL (or, if appropriate, DYINL) and the motif PSAP of the sequence SEQ ID NO. 8.

The sequence of the mutated derivative of the CD domain with sequence SEQ ID NO. 6 is preferably deprived of the motif PC (proline-cysteine) and CP (cysteine-proline) and, more preferably, deprived of the motif PCP (proline-cysteine proline). As an example, it may comprise or consist of the sequence SEQ ID NO. 10 or SEQ ID NO. 12.

In accordance with a particular embodiment, the CD domain or its mutated derivative, in particular the mutated derivative of the CD domain with sequence SEQ ID NO. 6, comprises or consists of a sequence selected from the following sequences:

```
PxxPxxxxPxxPxSxYxxLxPxxPExYxxLxPxxPDYxxL;

PxxPx_nPxxPx_nSxYxxLx_nPxxPEx_nYxxLx_nPxxPDYxxL;

PxxPxxxxPxxPxSxYxxLxPxxPExYxxLxPxxPDYxxLxxxx;
and

PxxPx_nPxxPx_nSxYxxLx_nPxxPEx_nYxxLx_nPxxPDYxxLxxxx;
``` in which x and $x_n$ respectively represent any residue and one or more of any residue(s), and in which at least one of the motifs PxxP is the motif PSAP or PTAP.

In accordance with a particular embodiment, the CD domain or its mutated derivative, in particular the mutated derivative of the CD domain with sequence SEQ ID NO. 6, comprises or consists of a sequence selected from the following sequences:

```
PxxPxxxxxxxxxxxxYxxL;

PxxPxxxxxxxxxxxxDYxxL;

PxxPxxYxxxxxxxxxxYxxL;

PxxPxxYxxxxxxxxxDYxxL;

PxxPExYxxLxPxxPDYxxL;

PxxPx_nYxxL;

PxxPx_nDYxxL;

PxxPx_nYx_nYxxL;

PxxPx_nYx_nDYxxL;

PxxPEx_nYxxLx_nPxxPDYxxL;

PxxPxxxxPxxPxxxxYxxLxPxxPExYxxLxPxxPDYxxL;

PxxPx_nPxxPx_nYxxLx_nPxxPEX_nYxxLx_nPxxPDYxxL;

PxxPxxxxPxxPxxxxYxxLxPxxPExYxxLxPxxPDYxxLxxxx;
and

PxxPx_nPxxPx_nYxxLx_nPxxPEX_nYxxLx_nPxxPDYxxLxxxx.
``` in which x and $x_n$ respectively represent any residue and one or more of any residue(s), at least one of the motifs PxxP being the motif PSAP or PTAP.

In particular, n is greater than or equal to 1 and less than 50. In particular, n may have any value between 1 and 20.

By way of example, the motif PxxP which, in a particular embodiment, is located at the N-terminal position in the sequences indicated above, may be the motif PSAP or PTAP.

Alternatively or in a complementary manner, the motif YxxL which, in a particular embodiment, is in the C-terminal position in the sequences indicated above, may be the motif YINL or YSHL, for example.

In a particular embodiment of the invention, when the CD domain or its mutated derivative comprises one of the above sequences, the consecutive amino acid residues added upstream or downstream of this sequence form neither a motif PxxP nor a motif YxxL, YxxF, DYxxL or DYxxF.

In accordance with a particular embodiment, said mutated derivative of the CD domain with sequence SEQ ID NO. 6 comprises 6 to 100 residues, in particular 20 to 80, 30 to 70 or 40 to 60, for example 40, 41, 42, 43, 44, 45, 46, 47, 48, 49 or 50 residues.

By way of example, the sequence of the mutated derivative of the CD domain may comprise or consist of the sequence SEQ ID NO. 30, SEQ ID NO. 42, SEQ ID NO. 44 or SEQ ID NO. 95 or have at least 60% or 70%, in particular at least 80%, 90% or 95% similarity or identity with the sequence SEQ ID NO. 30, SEQ ID NO. 42, SEQ ID NO. 44 or SEQ ID NO. 95 with reference respectively to the complete sequence SEQ ID NO, 30, SEQ ID NO. 42, SEQ ID NO. 44 or SEQ ID NO. 95.

The term "peptide or polypeptide of interest" as used in the present application means a concatenation of a plurality of (at least two) successive residues, forming the structure of a peptide or of a polypeptide. A "peptide" designates a chain of 2 to 20 successive residues (in particular 2, 3, 4, 5, 6, 7, 8, 9, 10, 11, 12, 13, 14, 15, 16, 17, 18, 19 or 20 residues), in particular a chain of 5 to 10, 10 to 15 or 15 to 20 successive residues. A "polypeptide", which also designates a protein or a fragment of a protein, is a concatenation of more than 20 (at least 21) successive residues, in particular a chain of 21 to 1000 successive residues, preferably 21 to 500, 21 to 250 or 21 to 150 successive residues, for example 21 to 50, 50 to 100 or 100 to 150 successive residues. Said peptide or polypeptide of interest may in particular comprise or consist of one or more domains of a soluble, membrane, transmembrane and/or multimeric protein.

In accordance with a particular embodiment, the "peptide or polypeptide of interest", in particular the peptide or polypeptide of interest present in the chimeric polypeptide of the invention, comprises or consists of one or more domain(s) of a cytosolic protein or of a nuclear protein, or one or more fragment(s) of this (these) domain(s).

The term "fragment" of a domain as used in the present application means a portion composed of at least 6 contiguous residues of said domain, and in particular a portion having at least 50%, preferably at least 60%, 70%, 80%, or at least 90%, or even 100% identity with the complete sequence for said domain. Whatever it is, a fragment has a smaller size than the protein from which it derives.

In accordance with a particular embodiment, said peptide or polypeptide of interest is antigenic, i.e. it is capable of eliciting an immune response directed against said peptide or polypeptide of interest. Said peptide or polypeptide of interest may in particular comprise or consist of one or more epitope(s) of a protein.

In accordance with a particular embodiment, said peptide or polypeptide of interest originates from a pathogenic organism, for example a virus, a bacterium or a parasite, or from a pathogenic agent, for example a tumor cell, a toxin, etc. Any cytoplasmic or nuclear peptide component of such an organism or pathogenic agent may be used, whether or not it is a structure protein. It may in particular be an antigen of a pathogen, and in particular a viral or bacterial antigen or an antigen originating from a parasite.

Said peptide or polypeptide of interest may also originate from a cytoplasmic antigen, and in particular from a tumoral cytoplasmic antigen, or from the cytosolic portion of a transmembrane protein. It may alternatively be an enzyme or a portion of an enzyme or a mutated derivative of an enzyme, or a toxin protein, or a portion of a toxin protein, or a compound selected for its capacity to act specifically on a cell (said compound could have a deleterious effect or, in contrast, a beneficial effect on a target cell). It may also be a protein (for example a G protein) or a protein fragment, capable of specifically fixing a nucleic acid, for example the capsid protein of the MS2 phage. It may also be a peptide or polypeptide capable of binding a particular nucleic acid.

Depending on the type of peptide or polypeptide of interest that is selected, the invention could be used in vivo, in particular for a medical application, especially for immunization, in particular vaccination.

By way of example, in two chimeric polypeptides of the invention described in the examples, the polypeptide of interest is a mutated derivative of the protein hAGT. Said mutated derivative is the SNAP protein, which is commercially available (Covalys, NEB). In accordance with a particular embodiment, a chimeric polypeptide as defined in the present application further comprises at least one binding molecule (or linker). The term "linker" designates any element that can link two successive domains. Its length and nature may vary.

In accordance with a particular embodiment, at least two successive domains of the polypeptide of the invention are bonded covalently, for example via peptide bonds. Thus, in accordance with a particular embodiment, said linker is a polypeptide or a peptide. This polypeptide linker may consist of a sequence of 2 to 50 residues, preferably 2 to 30 residues, for example 2 to 5, 5 to 10, 10 to 20 or 20 to 30 successive residues.

In accordance with a particular embodiment, the nucleotide sequence coding for said linker comprises or consists of a restriction site. The term "restriction site", means a particular nucleotide sequence recognized by a type II restriction enzyme as a cleavage site in the DNA molecule. Thus, this linker may, for example, be the linker with sequence SR, or AS, or PAGSGAP (SEQ ID NO. 106), coded for respectively by the nucleotide sequences TCTAGA, or GCTAGC, or CCTGCAGGAAGCGGCGCGCCC (SEQ ID NO. 107) which respectively comprise the restriction enzyme sites XbaI, Nhe I and Sbf I-Asc I.

In a preferred embodiment, the peptide or polypeptide of interest is in its native conformation in the chimeric polypeptides described in the present application and in particular in the chimeric polypeptide of the invention.

In accordance with a particular embodiment, a chimeric polypeptide as defined in the application is multimeric and in particular is in the form of a dimer or of a trimer. This may in particular be the case when the peptide or the polypeptide of interest originates from a protein that dimerizes or trimerizes in its native form.

In accordance with a particular embodiment, a chimeric polypeptide as defined in the application further comprises a sequence tag that enables it to be purified. As an example, said sequence tag may comprise or consist of a plurality of consecutively linked histidine residues, in particular a sequence of 6 consecutive histidine residues.

In accordance with a particular embodiment, a chimeric polypeptide as defined in the application comprises a tag or reporter protein, which may for example be an enzyme, and which is intended to label the polypeptide, for example by associating it with a fluorophore, or any other tag or substrate that can bind the tags (for example biotin). Such a protein may, for example, be the SNAP protein or a mutated derivative of the SNAP protein, which conserves the tagging properties normally attached to the SNAP protein.

In accordance with a particular embodiment, a chimeric polypeptide as defined in the application comprises the protein hAGT, which has the GenBank accession number M29971.1, or a derivative of or mutation of the protein hAGT (Keppler et al, 2002) contained in the plasmid pSNAPm (NEB, USA).

In accordance with a particular embodiment, the chimeric polypeptide further comprises a tag for detecting the chimeric polypeptide by ELISA or Western Blot. Preferably, said tag is an epitope recognized by a specific monoclonal antibody, for example a myc epitope.

In a particular embodiment of the invention, in the chimeric polypeptides described in the present application and in particular in the chimeric polypeptide of the invention, the peptide or polypeptide of interest is advantageously in its native conformation (in particular in the form of a multimer, for example in the form of a dimer or trimer) when it is associated with exosomes.

The present invention also concerns the use of a chimeric polypeptide of the invention as defined in the present application, to address (in vivo or in vitro) a peptide or polypeptide of interest that it comprises to membrane vesicles, in particular to exosome-forming vesicles, and/or to cellular compartment(s) involved in the formation of the membrane vesicles, and in particular exosome-forming vesicles, and thus to enable secretion, by appropriate eukaryotic cells, of said peptide or polypeptide of interest in combination with said membrane vesicles.

In a particular aspect of the invention, the chimeric polypeptide of the invention may be used in association with a chimeric polypeptide, hereinafter referred to as an "additional chimeric polypeptide".

In accordance with a particular embodiment of the invention, the additional chimeric polypeptide comprises or consists of the following domains:
  a peptide or a polypeptide of interest;
  a transmembrane domain; and
  a cytoplasmic domain (CD) or a mutated derivative of said CD domain, said CD domain and its mutated derivative being as defined in the present application;
these domains being positioned in succession in the following order, from the N-terminal end towards the C-terminal end: peptide or polypeptide of interest-transmembrane domain-CD domain or its mutated derivative; or CD domain or its mutated derivative-transmembrane domain-peptide or polypeptide of interest.

The additional chimeric polypeptide necessarily comprises at least one membrane domain (the transmembrane domain), but it may comprise a plurality of them; since the peptide or polypeptide of interest may comprise zero, one or more membrane domain(s), in particular transmembrane (see below), the additional chimeric polypeptide comprises one or more membrane domains (in particular transmembrane(s)). When said chimeric polypeptide comprises just one membrane domain (the transmembrane domain), it may or may not be derived from the same entity, in particular from the same protein as the peptide or polypeptide of interest of said polypeptide.

The CD domain or the mutated derivative of the additional chimeric polypeptide may be identical to or different from the CD domain or the mutated derivative of the CD domain of the chimeric polypeptide of the invention.

In the present application, a "membrane domain", designates any domain that is capable of interacting with a lipid bilayer and in particular capable of anchoring—and thus of anchoring a polypeptide comprising it—in a lipid bilayer and in particular in a vesicular or cellular membrane and in the membrane of an exosome. In a particular embodiment, this membrane domain is capable of binding on the one hand to a first domain (for example a peptide or a polypeptide of interest) and on the other hand to a second domain (for example a cytoplasmic domain). It may, for example, comprise 10 to 50 residues, preferably 15 to 40 residues and more preferably 20 to 30 residues. In accordance with a particular embodiment, said membrane domain is a transmembrane domain, i.e. a membrane domain passing completely through the lipid bilayer of a vesicular or cellular membrane. A transmembrane domain is generally arranged as a hydrophobic α helix; multi-pass transmembrane proteins may contain a plurality, in particular 2, 3, 4, 5, 6, 7, 8, 9 or 10, or even 20 or more than 20 hydrophobic α helixes. It may also be arranged as a β sheet. One or more transmembrane domains may also adopt a β-barrel transmembrane structure, generally composed of 8 to 22 β strands.

The term "membrane protein" means any polypeptide chain comprising one or more membrane domain(s) as defined above.

Like the chimeric polypeptide of the invention, the additional chimeric polypeptide is capable of being secreted in combination with membrane vesicles, in particular with exosomes, when it is expressed in appropriate eukaryotic cells.

Because of its membrane domain(s), in particular because of its transmembrane domain(s), the additional chimeric polypeptide or a degradation product of said polypeptide can anchor itself in the membrane of a membrane vesicle (in particular an exosome) by inserting itself in the lipid bilayer of this membrane. A degradation product of said chimeric polypeptide may also be anchored in the membrane of a membrane vesicle via the membrane (in particular transmembrane) domain of a MHC molecule (class I or II) with which said degradation product of said chimeric polypeptide is associated.

In an additional chimeric polypeptide thus anchored in the membrane of a membrane vesicle (in particular an exosome), the peptide or a polypeptide of interest may be exposed (entirely or in part) to the outside of said membrane vesicle and/or included (entirely or in part) in the membrane of said membrane vesicle (this is the case when said polypeptide or peptide of interest comprises one or more membrane domains) and/or included (entirely or in part) in the cytosolic fraction of said membrane vesicle.

In accordance with a particular embodiment of the invention, when the CD domain and a transmembrane domain of said additional chimeric polypeptide are derived from the same protein, then at least the CD domain, its mutated derivative or the transmembrane domain derived from the same protein as the CD domain is a derivative mutated by substitution and/or deletion of one or more residue(s) in the sequence of the original domain.

The transmembrane domain may be derived from one or more transmembrane protein(s), which pass one or more times, in particular 2, 3, 4, 5, 6, 7, 8, 9 or 10 times, or even 20 times, or more, through a vesicular or cellular membrane. Said membrane or transmembrane proteins may in particular be selected from: human proteins, proteins from a non-human animal, proteins from a pathogenic organism or a pathogenic agent, in particular viral proteins, bacterial proteins or proteins expressed by a parasite or a tumor cell.

The or at least one of the transmembrane domain(s) of the additional chimeric polypeptide may in particular be that of one and the same transmembrane protein or be a mutated derivative of the transmembrane domain of a membrane protein. Said mutated derivative may, for example, be obtained by replacing a portion of the sequence for the reference domain by a sequence derived from the transmembrane domain of another transmembrane protein.

In accordance with a particular embodiment of the invention, when the CD domain of the additional chimeric polypeptide or its mutated derivative comprises or consists of the CD domain of the TM protein of BLV, with sequence SEQ ID NO. 6, the membrane domain(s) of said additional chimeric polypeptide is(are) deprived of the transmembrane domain of the TM protein of BLV, which has the sequence SEQ ID NO. 4. A transmembrane domain of the additional chimeric polypeptide may, in contrast, correspond to a mutated derivative of the domain with sequence SEQ ID NO. 4, said mutated derivative not comprising the sequence SEQ ID NO. 4. Such a mutated derivative may be obtained by deletion and possible substitution of one or more residue(s) in the sequence SEQ ID NO. 4, as illustrated in the examples.

In accordance with a particular embodiment, when one of the transmembrane domain(s) and the CD domain derive from the same protein, in particular when they derive from the TM protein of BLV, a mutated derivative of the CD domain deprived of the sequence PCP (the residue C of the sequence PCP being replaced by a residue A, for example), and/or deprived of the sequence KCLTSRLLKLLRQ, is used as the domain (iii).

In accordance with a particular embodiment, when one of the membrane domains of the additional chimeric polypeptide comprises or consists of the transmembrane domain of the TM protein of BLV, with sequence SEQ ID NO. 4, the CD domain or its mutated derivative is deprived of the CD domain of the TM protein of BLV, with sequence SEQ ID No. 6. The CD domain or its mutated derivative may, in contrast, correspond to or comprise a mutated derivative of the domain with sequence SEQ ID NO. 6. As illustrated in the examples, such a mutated derivative may be obtained, for example, by deleting the residues situated in the N-terminal portion of the sequence SEQ ID NO. 6, in particular by deleting the sequence KCLTSRLLKLLRQ and/or by deleting the sequence PCP in the sequence SEQ ID NO. 6, or by substituting, for example, the cysteine residue of the sequence PCP with another residue, preferably by a non-palmitylable residue, for example an alanine residue.

The peptide or polypeptide of interest present in this additional chimeric polypeptide may be as defined in the application for the chimeric polypeptide of the invention. Alternatively or cumulatively, said peptide or polypeptide of interest of the additional chimeric polypeptide may also comprise or consist of one or more domain(s) of an extracellular protein or of a surface protein or one or more fragment(s) of one or more of this (these) domain(s).

In accordance with a particular embodiment, the peptide or the polypeptide of interest present in this additional chimeric polypeptide comprises or consists of one or more domain(s) of an extracellular or surface protein or one or more fragment(s) of one or more of these domain(s) and, if appropriate, of:
  one or more membrane domain(s) of a membrane protein, in particular of a transmembrane protein or one or more fragment(s) of this (these) domain(s), and/or
  one or more cytoplasmic domain(s) of a membrane protein, in particular of a transmembrane protein, or one or more fragment(s) of this (these) domain(s).

In accordance with a particular embodiment of the invention, the peptide or polypeptide of interest of the additional chimeric polypeptide is a receptor, for example a receptor with multiple membrane domains and in particular a CXCR4 or GPR receptor, or any other peptide or polypeptide that can be used to target a target cell or a particular type of target cell (for example tumor cells or cells with a metabolic or functional disorder).

In accordance with a particular embodiment of the invention, the peptide or polypeptide of interest of this additional chimeric polypeptide comprises or consists of one or more ectodomain(s) and/or one or more membrane domain(s) and/or one or more cytoplasmic domains(s) of a membrane protein, in particular of a transmembrane protein, or one or more fragment(s) of one or more of this (these) domain(s).

In accordance with a particular embodiment of the invention, said peptide or polypeptide of interest of this additional chimeric polypeptide originates from a pathogenic organism, for example a virus, a bacterium or a parasite, or from a pathogenic agent, for example a tumor cell, a toxin etc., or from a tumoral antigen, from a cytoplasmic antigen, from a ligand receptor, in particular from a receptor with multiple membrane domains, for example a receptor with seven transmembrane domains, from a cytokine receptor or from a ligand receptor, in particular from a cytokine or a fragment thereof. Any peptide component from an organism or a pathogenic agent may be used, whether or not it is a structure protein. It may in particular be a pathogenic antigen, in particular a viral or bacterial antigen or an antigen originating from a parasite.

Said peptide or polypeptide of interest of this additional chimeric polypeptide may also originate from a tumoral antigen, from a cytoplasmic antigen, from a transmembrane protein, in particular from an integrin or from a co-receptor or from a protein involved in interactions (in particular the proteins ICAM, CD4, CD8), from a ligand receptor, in particular from a receptor with a single membrane domain, for example a cytokine receptor (in particular the receptors from the HER family responding to the EGF, for example the receptor EGF-R1), in particular from a receptor with multiple membrane domains, for example a receptor with seven transmembrane domains (in particular the receptor CXCR4 of HIV or a receptor for gamma amino butyric acid (GABA)), or from a ligand receptor, in particular from a cytokine or a fragment thereof.

Depending on the type of peptide or polypeptide of interest present in this additional chimeric polypeptide, the invention could be used in vitro, for example to screen molecules interacting with said peptide or polypeptide of interest.

In accordance with a particular embodiment, said peptide or polypeptide of interest originates from a protein present on the surface of a virus, for example a protein responsible for binding of a viral particle to a receptor located on a target cell and/or responsible for fusion of the viral envelope or of the plasma membrane of an infected cell with the plasma membrane of a target cell, or a fragment of such a protein.

By way of example, it is possible to use, as domain (i), an envelope protein of an enveloped virus or a fragment of this protein. This enveloped virus may in particular be selected from the following families:

the Poxyiridae, in particular those of the genus *Orthopoxvirus*, which in particular comprises the smallpox virus and the vaccinia virus;
the Herpesviridae, in particular those of the genus *Herpesvirus*, which in particular comprises *Herpesvirus* types 1 and 2, chicken pox virus, Epstein Barr virus, Cytomegalovirus, and *Herpesvirus* types 6, 7, 8;
the Hepadnaviridae, which in particular comprise hepatitis B virus;
the Orthomyxoviridae, in particular those of the genus virus influenza A, B or C, which in particular comprises the H5N1 bird flu virus;
the Paramyxoviridae, in particular those of the genus *Paramyxovirus*, which in particular comprises the parainfluenzae viruses and the mumps virus, those of the genus *Morbillivirus*, which in particular comprises the measles virus, and those of the genus *Pneumovirus*, which in particular comprises the respiratory syncytial virus;
the Rhabdoviridae, in particular those of the genus *Lyssavirus*, which in particular comprises the rabies virus;
the Filoviridae, which in particular comprise the Marburg virus and the Ebola virus;
the Togaviridae, in particular those of the genus *Flavivirus*, which in particular comprises the yellow fever virus and the hepatitis C virus (HCV), those of the genus Alphavirus and those of the genus *Rubivirus*, which in particular comprises the rubella virus;
the Coronaviridae, in particular those of the genus *Coronavirus*, which in particular comprises viruses responsible for respiratory and digestive infections such as severe acute respiratory syndrome (SARS);
the Arenaviridae, in particular those of the genus *Arenavirus*, which in particular comprises the Lassa virus;
the Bunyaviridae, in particular those of the genus *Bunyavirus, Hantavirus, Phlebovirus*; and
the Retroviridae, in particular those of the genus *Lentivirus* and in particular human immunodeficiency virus (HIV).

Again by way of example, the peptide or polypeptide of interest may originate from an envelope protein of an influenza virus, in particular hemagglutinin (HA) from an influenza virus, and more particularly the HA protein of the H5N1 bird flu virus. It may be the ectodomain of this protein or a fragment of this ectodomain or a fragment comprising or consisting of one or more epitope(s) of this ectodomain.

Other antigenic polypeptides of these viruses may of course be used, such as the GAG protein or a fragment of the GAG polyprotein of HIV, the protein or a fragment of the capsid of poliovirus or of a papillomavirus.

Again by way of example, the peptide or polypeptide of interest may originate from a protein of the outer envelope of one of these viruses. It may originate from an envelope protein of a *coronavirus*, in particular from the Spike (S) protein of a *coronavirus*, and more particularly the Spike protein of a severe acute respiratory syndrome *coronavirus* (SARS-CoV). This peptide or polypeptide of interest may in particular comprise or consist of the ectodomain of this protein or a fragment comprising or consisting of one or more epitope(s) of this ectodomain.

In a particular embodiment, the peptide or polypeptide of interest of the additional chimeric polypeptide has the capacity to recognize a protein present at the surface of target cells, for example dendritic cells, lymphocytes, tumor cells, etc.

Addressing the additional chimeric polypeptide to the formation location(s) of membrane vesicles and in particular to the formation location(s) of exosomes may in particular require that said additional chimeric polypeptide should comprise a signal peptide for importation into the endoplasmic reticulum, so that said additional chimeric polypeptide can be inserted into a vesicular or cellular membrane (the anchoring function in the membrane being ensured by the transmembrane domain). Thus, in accordance with a particular embodiment, in contrast to the chimeric polypeptide of the invention, the additional chimeric polypeptide may comprise one (or more) signal peptide(s) for importation into the endoplasmic reticulum.

The term "signal peptide for importation into the endoplasmic reticulum", means a small continuous polypeptide sequence of approximately 5 to approximately 60 residues, in particular 15 to 60 residues and more particularly 15 to 30 residues, which enables a protein comprising it to pass through the membrane of the endoplasmic reticulum, passage of the protein possibly being complete or partial; halting of the passage of the protein depends on the presence of another additional signal (or other signals). Since signal peptides for a given destination are interchangeable from one protein to another, any signal peptide that can enable addressing of a protein to the endoplasmic reticulum may be used in the context of the present invention.

By way of example, the signal peptide used for importation into the endoplasmic reticulum may be a 27 residue peptide with sequence SEQ ID NO. 2. Again by way of example, the signal peptide of a membrane protein such as the proteins CD4, CD8 and hemagglutinin (HA), the signal peptide of a cytokine receptor such as IL1R1, EGFR1 (HER1), HER2, HER3 or HER4, or again the signal peptide of a secreted protein, for example, that of a cytokine, may be used. Thus, a signal peptide may be used that is selected from: that of the human CD4 protein (peptide with sequence SEQ ID NO. 49) or Mouse CD4 (peptide with sequence SEQ ID NO. 50), that of the protein mouse CD8 alpha (peptide with sequence SEQ ID NO. 51), bovine CD8 alpha (peptide with sequence SEQ ID NO. 52), human CD8 alpha (peptide with sequence SEQ ID NO. 53), or rat CD8 alpha (peptide with sequence SEQ ID NO. 54), that of the human IL1R1 receptors (peptide with sequence SEQ ID NO, 55), human EGFR1 (HER1) (peptide with sequence SEQ ID NO. 56), human HER2 (peptide with sequence SEQ ID NO. 57), human HER3 (peptide with sequence SEQ ID NO, 58) or human HER4 (peptide with sequence SEQ ID NO. 59), or that of the cytokines mouse IL-2 (peptide with sequence SEQ ID NO. 60), mouse IL-6 (peptide with sequence SEQ ID NO. 61), human IL-7 (peptide with sequence SEQ ID NO. 62), mouse IL-10 (peptide with sequence SEQ ID NO. 63), or human MIP-1-alpha chemokine (peptide with sequence SEQ ID NO. 64), that of the hemagglutinin of Influenza B virus (peptide with sequence SEQ ID NO. 65), that of the hemagglutinin of the viruses Influenza A H1N1 (peptide with sequence SEQ ID NO. 66), Influenza A H2N2 (peptide with sequence SEQ ID NO. 67), Influenza A H3N2 (peptide with sequence SEQ ID NO. 68), Influenza A H4N6 (peptide with sequence SEQ ID NO. 69), Influenza A H5N1 (peptide with sequence SEQ ID NO. 70), Influenza A H6N5 (peptide with sequence SEQ ID NO. 71), Influenza A H7N7 (peptide with sequence SEQ ID NO. 72), Influenza A H8N4 (peptide with sequence SEQ ID NO. 73), Influenza A H9N2 (peptide with sequence SEQ ID NO. 74), Influenza A H10N7 (peptide with sequence SEQ ID NO. 75), Influenza A H11N6 (peptide with sequence SEQ ID NO. 76), Influenza A H12N5 (peptide with sequence SEQ ID NO, 77), or Influenza A H13N6 (peptide with sequence SEQ ID NO. 78).

In accordance with another particular embodiment, said signal peptide for importation into the endoplasmic reticulum may form part of the peptide or polypeptide of interest of the additional chimeric polypeptide. This is the case, for example, when said peptide or polypeptide of interest is a membrane protein or a cytokine.

Independently or in combination with the above embodiment, said signal peptide for importation into the endoplasmic reticulum may form part of one of the membrane domains (in particular a transmembrane domain) of the additional chimeric polypeptide. This may, for example, be the case when the transmembrane domain or one of the membrane domains of said polypeptide is derived from a receptor with seven transmembrane domains.

Alternatively, in accordance with another embodiment, said signal peptide for importation does not form part of any of the three principal domains (namely the domains: peptide or polypeptide of interest; transmembrane domain; CD domain or its mutated derivative), and as a consequence is added into the additional chimeric polypeptide in addition to these three domains. It may then be placed at different locations in the linear sequence of said polypeptide, but is generally at one end of said polypeptide and is preferably at the N-terminal position in said polypeptide.

If a second signal peptide for importation into the endoplasmic reticulum is added to the additional chimeric polypeptide, it can if appropriate be used to enhance membrane targeting.

In a mature form, in particular when it is anchored in the membrane of a membrane vesicle, for example an exosome, the additional chimeric polypeptide generally does not comprise or no longer comprises a N- or C-terminal peptide for importation into the endoplasmic reticulum; after it has fulfilled its function, the N- or C-terminal signal peptide may be separated from the polypeptide by proteolytic cleavage, for example in the endoplasmic reticulum or in the Golgi.

The present invention also provides a membrane vesicle, and more precisely an exosome, which comprises a chimeric polypeptide of the invention, and/or one or more degradation product(s) of said chimeric polypeptide of the invention, this (these) degradation product(s) if appropriate being associated with a molecule of the major histocompatibility complex (MHC) type I and/or type II.

The chimeric polypeptide of the invention and/or its degradation product(s) is(are) anchored in the membrane of said membrane vesicle via the infra-membrane targeting domain or via the membrane domain of the MHC molecule (class I or II) to which it (they) is(are) associated. In accordance with a particular embodiment, a degradation product comprises or consists of a fragment of the peptide or polypeptide of interest, in particular a fragment comprising or consisting of one or more epitope(s) of said peptide or polypeptide of interest. In a particular embodiment, the membrane vesicle of the invention, and more precisely the exosome of the invention, comprises, in addition to the chimeric polypeptide of the invention and/or any degradation product(s), one or more additional chimeric polypeptide(s) described in the application, and/or one or more degradation product(s) of this (these) additional chimeric polypeptide(s), the degradation product(s) of the additional chimeric polypeptide(s) if appropriate being associated with a molecule of the major histocompatibility complex (MHC) type I and/or type II.

Alternatively, the vesicle of the invention which comprises a chimeric polypeptide of the invention may be used in combination with a membrane vesicle (in particular an exosome), hereinafter termed the "additional membrane vesicle" (and in particular "additional exosome"), which comprises one or more additional chimeric polypeptide(s), and/or one or more degradation product(s) of this (these) additional chimeric polypeptide(s) described in the application, this (these) degradation product(s) if necessary being associated with a molecule of the major histocompatibility complex (MHC) type I and/or type II.

By way of example, the membrane vesicle of the invention, and more precisely the exosome of the invention, may comprise:

on the one hand, a chimeric polypeptide of the invention (and/or any degradation product(s)) in which the peptide or polypeptide of interest is a cytosolic protein, for example an antigen, a G protein, an enzyme (for example a cytosolic enzyme which is defective in the target cell(s)), a toxin or any other cytosolic peptide or polypeptide that may have a deleterious or, in contrast, a beneficial effect for a target cell, or a peptide or polypeptide capable of binding a particular nucleic acid, said chimeric polypeptide of the invention optionally being tagged, for example by a first fluorophore;

on the other hand, an additional chimeric polypeptide, (and/or its degradation product(s) if any) in which the peptide or polypeptide of interest is, for example, a receptor (for example a receptor with multiple membrane domains and in particular a CXCR4 or GPR receptor) or any other peptide or polypeptide that can be used to target a target cell or a particular type of target cells (for example tumor cells or cells with a metabolic or functional disorder), said additional chimeric polypeptide preferably being tagged, for example by a second fluorophore (distinct from the first fluorophore).

Such a vesicle of the invention may have many applications; in particular, it may be used to modify the content of target cells. When it is administered to a cell, to a population of cells or to a human or non-human host, this vesicle can be internalized by certain cells (for example dendritic cells or tumor cells) targeted via the peptide or polypeptide of interest present in the additional chimeric polypeptide (or via any degradation product(s)) of this vesicle. By internalizing said vesicle, the target cells internalize the peptide or polypeptide of interest of the chimeric polypeptide of the invention present in this vesicle; depending on the nature of said peptide or polypeptide of interest, this may have various applications—in particular, it can be used to:

treat the target cells (by adding an enzyme, for example);

in contrast, destroy the target cells (for example tumor cells); or carry out a diagnostic, for example by detecting a nucleic acid bound to the peptide or polypeptide of interest of the chimeric polypeptide of the invention;

induce an immune response, for example directed against a cytosolic antigen present in the chimeric polypeptide of the invention;

carry out screening of proteins and/or analyze any interactions between proteins (for example by detecting any energy transfers between the two fluorophores used).

The membrane vesicle of the invention, whether or not it comprises an additional chimeric polypeptide, may in particular be used to produce in vivo or in vitro monoclonal or polyclonal antibodies, vaccinating or non-vaccinating, directed against said peptide or polypeptide of interest or their fragment. Such antibodies may in particular be used in diagnostics or for the study of protein interactions, in particular to carry out high throughput screening of molecules such as drugs or cytokines capable of interacting with the peptide or the polypeptide of interest or their fragment.

Further, the membrane vesicle of the invention, whether or not it also comprises an additional chimeric polypeptide, may be used in vivo, for immunization, to elicit or promote, in a host (human or non-human), a humoral and/or cellular response against a tumor, or against the virus, bacterium or parasite from which the peptide or the polypeptide of interest derives. The immune response elicited or promoted by the membrane vesicle of the invention, in particular by an exosome of the invention, may, depending on the nature of the polypeptides associated with the exosomes, be a tolerogenic or defense response. A tolerogenic response may, for example, enable the host to combat asthma or tolerate a graft.

In a membrane vesicle comprising an additional chimeric polypeptide, (and/or its degradation product(s) if any), the peptide or the polypeptide of interest occurring in said additional chimeric polypeptide(s) or a fragment of said peptide or the polypeptide of interest is exposed, in part or in its entirety, at the surface, on the outside of the membrane vesicle. As a consequence, a vesicle of the invention also comprising an additional chimeric polypeptide may in particular be used to produce or select or target, in vivo or in vitro, prokaryotic or eukaryotic cells or viruses (for example phages) or ribosomes interacting directly or indirectly with said peptide or polypeptide of interest or their fragment. In a preferred embodiment, said peptide or polypeptide of interest of the additional chimeric polypeptide, or the fragment of said peptide or polypeptide of interest, is exposed (in part or in its entirety) in its native conformation at the surface of the membrane vesicle.

In accordance with a particular embodiment, the peptide or the polypeptide of interest of the additional chimeric polypeptide or the fragment of said peptide or polypeptide of interest is included in part or in its entirety in the membrane of the membrane vesicle of the invention, and/or included in part or in its entirety in the cytosolic fraction of said membrane vesicle.

A composition, in particular a therapeutic composition (for example pharmaceutical) or an immunogenic composition, the active principle of which comprises one or more chimeric polypeptide(s) of the invention or one or more membrane vesicle(s) of the invention, in particular one or more exosome(s) of the invention, also form part of the invention.

In accordance with a particular embodiment, said composition further comprises:

one or more additional chimeric polypeptide(s); or one or more additional membrane vesicle(s) (in particular one or more additional exosome(s)).

Alternatively, said composition may be used (in particular administered to a human or non-human host) in conjunction with another composition, in particular another therapeutic or immunogenic composition, which comprises one or more additional chimeric polypeptide(s) and one or more additional membrane vesicle(s).

In accordance with a particular embodiment, said composition(s) further comprises (comprise) one or more vehicle(s), diluent(s) and/or adjuvant(s) or one of their combinations. In the case of administration by injection, a formulation in an aqueous, non-aqueous or isotonic solution may be selected.

In the present application, the term "vehicle", designates any support (i.e. anything that can transport at least one active principle) that does not alter the efficacy of the biological activity of the active substances of the invention. Many vehicles are known in the art. The vehicles used may, for example, be water, saline solution, serum albumin, Ringer's solution, polyethylene glycol, solvents that are miscible with water, sugars, binding agents, excipients, pigments, vegetable or mineral oils, polymers that are soluble in water, surfactants, thickening or gelling agents, cosmetic agents, solubilizing agents, stabilizing agents, preservatives, alkalinizing or acidifying agents, or one of their combinations.

In the present application, the term "diluent" means a diluting agent and includes soluble diluents and insoluble diluents. In general, an insoluble diluent is used when the active principle is soluble and a soluble diluent is used when the active principle is insoluble. An "insoluble" active principle may be completely insoluble in an aqueous medium or have a limited solubility (i.e. a solubility of less than 10 mg/mL in 250 mL of water at a pH of 1.0 to 7.5) in an aqueous medium. Examples of insoluble diluents include microcrystalline cellulose, silicified microcrystalline cellulose, hydroxymethylcellulose, dicalcium phosphate, calcium carbonate, calcium sulfate, magnesium carbonate, tricalcium phosphate, etc. Examples of soluble diluents include mannitol, glucose, sorbitol, maltose, dextrates, dextrins, dextrose, etc.

The term "adjuvant" as used in the present application designates a product that, added to the contents of an immunogenic composition, in particular to a vaccine, increases the intensity of the immune reaction induced in the host (human or non-human) to whom said composition is administered. An adjuvant may in particular increase the quantity of specific antibodies that said mammal is capable of producing after administration of said composition, thereby increasing the efficacy of the immunization. Adjuvants are especially useful when the antigen used alone produces an immune reaction that is too weak to procure good protection, when the quantity of antigen to be administered to a host is to be reduced, or in order to facilitate certain modes of administration of said composition, for example in the case of administration to the mucous membranes. Particular examples of adjuvants that can be used in the context of the invention are saponins, aluminum phosphate (alum), peptidoglycans, carbohydrates, peptides, for example muramyl dipeptide (N-acetylmuramyl-L-alanyl-D-isoglutamine, MDP), oil/water emulsions, polysaccharides, cytokines, hormones, limpet hemocyanin, adjuvants from the non-methylated CpG dinucleotide family, adjuvants from the poly IC family, adjuvants from the monophosphoryl lipid A family and nucleic acids, in particular bacterial DNA and DNA coding for a protein having an adjuvant effect, for example a growth factor or a cytokine, more particularly GM-CSF or IL4.

In a preferred embodiment, said vehicle(s), diluent(s) and/or adjuvant(s) or combinations thereof are pharmaceutically acceptable substances or a combination of pharmaceutically acceptable substances, i.e. appropriate for administration to a host (for example a human being, a non-human mammal or a bird) for therapeutic or prophylactic purposes. Such a substance or combination of substances is thus preferably non-toxic to the host to which it is administered.

The present invention also provides a polynucleotide characterized in that it codes for a chimeric polypeptide in accordance with the universal genetic code taking the degeneracy of this code into account. The term "polynucleotide" encompasses any DNA or RNA molecule (single- or double-stranded). This polynucleotide may be naked or, alternatively, it may be inserted into a cloning or expression vector, preferably a vector suitable for expression in eukaryotic cells. Preferably, this vector is a plasmid. Said polynucleotide may in particular be assembled by PCR. It preferably comprises 2000 to 50000 nucleotides.

The term "code" does not necessarily mean that said polynucleotide only contains the coding portion. Said polynucleotide may in fact also comprise expression regulation sequences and in particular comprise a promoter, for example a eukaryotic promoter.

By way of example, said polynucleotide comprises, as the sequence coding for the CD domain of the chimeric polypeptide of the invention or for the mutated derivative of said CD domain, a sequence comprising or consisting of a sequence selected from the sequences SEQ ID NO. 5, SEQ ID NO. 7, SEQ ID NO. 9, SEQ ID NO. 11 SEQ ID NO, 47 and SEQ ID NO. 94.

In accordance with a particular embodiment, the polynucleotide of the invention further codes for an additional chimeric polypeptide as defined in the present application. Alternatively, the polynucleotide of the invention may be used in conjunction with a distinct polynucleotide, hereinafter termed the "additional polynucleotide", which codes for an additional chimeric polypeptide as defined in the present application.

In accordance with a particular embodiment, a polynucleotide coding for an additional chimeric polypeptide comprises a sequence coding for a signal for importation into the endoplasmic reticulum. As an example, this sequence may be the sequence SEQ ID NO. 1 or a sequence coding for a peptide with sequence SEQ ID NO. 49 to SEQ ID NO. 78. As indicated above, the signal peptide coded by this sequence, when it is in the N- or C-terminal position in the polypeptide coded by said polypeptide, may be cleaved during a step for maturation of the chimeric polypeptide, which generally takes place in the endoplasmic reticulum or in the Golgi.

Like the additional polynucleotide, the polynucleotide of the invention may be placed under the control of regulation, cloning or expression elements.

Thus, in accordance with a particular embodiment, said polynucleotide(s) is(are) inserted into a cloning or expression vector, preferably an expression vector and more preferably a vector suitable for expression in eukaryotic cells. Said vector is preferably a plasmid. The chimeric polynucleotide of the invention and the additional chimeric polynucleotide may be inserted into the same vector or into two distinct vectors.

Said polynucleotides are in general placed under the control of a eukaryotic promoter, preferably a strong eukaryotic promoter such as a viral promoter, for example the promoter of a virus selected from: SV40 virus, Rous sarcoma virus, murine leukemia virus (MuLV), adult human T cell leukemia virus (HTLV-I), bovine leukemia virus (BLV), cytomegalovirus, a hybrid promoter derived from these viral promoters or a viral promoter containing modified sequences.

Said polynucleotides may further comprise a kozak sequence, in particular the nucleotide sequence ACCATGG or a derivative sequence ACCATG, in which the sequence ATG corresponds to the start codon of the coding sequence.

Furthermore, said polynucleotides may further comprise one intron.

In accordance with a particular embodiment, said polynucleotides comprise at least one nucleotide linker coding for a polypeptide linker as defined above. This nucleotide linker may in particular comprise or consist of a restriction site. The term "restriction site" means a particular nucleotide sequence recognized by a type II restriction enzyme as a cleavage site in the polynucleotide. By way of example, these nucleotide linkers may consist of the nucleotide sequences TCTAGA, or GCTAGC, or CCTGCAG-GAAGCGGCGCGCCC, which respectively comprise the restriction enzyme sites XbaI, Nhe I, and Sbf I-Asc I.

In accordance with a particular embodiment, the sequence of said polynucleotide of the invention and/or the sequence of the additional polynucleotide are optimized for use in a host (for example a eukaryotic host), in particular a human being, a non-human mammal and/or a bird.

The present invention also provides a cloning or expression vector, preferably a plasmid, characterized in that it comprises a polynucleotide insert constituted by a polynucleotide of the invention, under the control of regulation, cloning or expression elements.

This cloning or expression vector may further comprise a polynucleotide insert constituted by an additional polynucleotide, under the control of regulation, cloning or expression elements. Alternatively, this cloning or expression vector may be used in conjunction with another cloning vector, hereinafter termed an additional cloning or expression vector, which comprises a polynucleotide insert constituted by an additional polynucleotide, under the control of regulation, cloning or expression elements.

The invention also provides a cell culture selected from the group comprising bacterial cell cultures, primary cell cultures of animal eukaryotic cells and cell lines, said cell culture containing a polynucleotide of the invention, a cloning or expression vector of the invention, or a chimeric polypeptide of the invention. If appropriate, said cell culture may further comprise an additional polynucleotide, an additional cloning or expression vector, or an additional chimeric polypeptide. The present invention also provides a composition, in particular a therapeutic or immunogenic composition, comprising a nucleic acid characterized in that it comprises or consists of a polynucleotide of the invention, and a pharmaceutically acceptable support, a diluent or a vehicle.

Said composition of the invention may further comprise a nucleic acid comprising or consisting of an additional chimeric polynucleotide. Alternatively, said composition of the invention may be used (in particular administered to a human or non-human host) in combination with a composition (termed additional) comprising a nucleic acid that comprises or consists of an additional polynucleotide, and a pharmaceutically acceptable support, a diluent or a vehicle.

In accordance with a particular embodiment, said composition(s) further comprise(s) an adjuvant as defined in the present application.

In accordance with a particular embodiment, said nucleic acid(s) is(are) a DNA. Immunogenic compositions based on DNA target cells of the host to be immunized in vivo, in particular dendritic cells (especially Langerhans cells), which are excellent producers of vaccinating exosomes. Thus, said immunogenic composition can be used to induce the production, by a host's own cells immunized with said immunogenic composition, of exosomes carrying the peptide or polypeptide of interest or a fragment thereof.

In accordance with a particular embodiment, said immunogenic composition(s) is(are) a vaccine, in particular a DNA vaccine.

The present invention also provides a recombinant exosome-producing cell, in particular a cell of the immune system and more particularly a cell of the immune system selected from mastocytes, lymphocytes, in particular B and T lymphocytes, and dendritic cells, in particular Langerhans cells, characterized in that it is recombined with one or more polynucleotide(s) of the invention or a cloning or expression vector of the invention and if necessary one or more additional polynucleotide(s) or an additional cloning or expression vector, or it has absorbed a membrane vesicle of the invention and/or an additional membrane vesicle. Further, the present invention also concerns an element selected from a chimeric polypeptide of the invention, one or more membrane vesicle(s) of the invention (in particular one or more exosome(s) of the invention), a polynucleotide of the invention and a composition of the invention, for use as a drug.

Said elements may in particular be used for the prophylaxis and/or treatment of a bacterial, viral or parasitic infection, or of a tumor, or a functional or metabolic deficit, in particular an enzymatic deficit. They are in particular intended for use in immunization, in particular to elicit or promote (i.e. amplify), in vivo, in a host (human or non-human), a humoral and/or cellular response against the tumor, virus, bacterium or parasite from which the peptide or polypeptide of interest derives. They may in particular be used in vivo to elicit or amplify a specific T CD4 and/or T CD8 response directed against the peptide or the polypeptide of interest and/or to produce polyclonal and/or monoclonal antibodies directed against the peptide or the polypeptide of interest, in particular antibodies directed against a peptide or a polypeptide comprising or consisting of one or more conformational epitopes.

In a particular embodiment, these elements are used to target predetermined cells in vivo.

Said elements may in particular be used to treat target cells in a human or non-human host (for example by adding an enzyme), and/or to destroy target cells in a human or non-human host and/or to induce an immune response directed, for example, against a cytosolic antigen present in the chimeric polypeptide of the invention in a human or non-human host (for example tumor cells) and/or to carry out diagnostics (for example by detecting a nucleic acid bound to the peptide or polypeptide of interest of the chimeric polypeptide of the invention).

Further, said elements may be used in vitro, to screen proteins and/or analyze any interactions between proteins (for example by detecting any energy transfers between two fluorophores that are employed).

The present invention also concerns the use of one of these elements for the manufacture of a drug intended for prophylaxis and/or treatment of a functional or metabolic deficit, in particular an enzymatic deficit, or of a tumor or an infection by a pathogenic organism or by a pathogenic agent, in particular a bacterial, viral or parasitic infection, and/or to elicit or amplify an immune response as described above, for example. Following administration of a composition of the invention the active principle of which is a polynucleotide of the invention (and, if necessary, an additional polynucleotide) or one or more membrane vesicle(s) of the invention (and, if necessary, one or more additional membrane vesicle(s)), to a host (human or non-human), the exosome-producing cells of that host, in particular the dendritic cells, will produce exosomes comprising a chimeric polypeptide and/or a degradation product of this latter, this degradation product being able to associate naturally with a molecule of the major histocompatibility complex. These membrane vesicles will be able to elicit or promote an immune response directed against the peptide or the polypeptide of interest.

A "host" in the context of the present application designates a human or a non-human animal.

The term "non-human animal" as used in the present application includes any non-human mammal, especially a rodent (in particular a mouse, a rat, a hamster or a rabbit), a monkey, a camelid, a cat, a dog, a horse, a mule, a cow, a sheep, a pig, and also includes a bird, in particular a chicken.

The expression "infection" as used in the present application means that said host (human or non-human) has been exposed to a pathogenic organism or a pathogenic agent, in particular to an enveloped virus as defined in the present application. In particular, such an infection is capable of developing to produce the clinical signs of disease induced by or accompanying said infection. The term "infection" thus also encompasses any clinical sign, symptom or disease appearing in a host (human or non-human) following exposure to a pathogenic organism or a pathogenic agent. For example, a "viral infection" or a "bacterial infection" in the context of the present application includes both the earliest phases of viral, bacterial or parasitic contamination, the intermediate phases and the latest phases of contamination, as well as the various diseases that are a consequence of contamination of a host by a virus, by bacteria or by a parasite; it also includes the presence of all or a portion of the genome of a pathogenic organism.

The term "prophylaxis" designates any degree of retardation in the time at which clinical signs or symptoms of infection appear or at which a tumor appears or any other pathology appears, in particular a functional or metabolic deficit (for example an enzymatic deficit), as well as any degree of inhibition of the severity of the clinical signs or symptoms of the infection or of the tumor including, but without limitation, total prevention of the infection or cancer. This requires that the chimeric polypeptides described in the application (in particular the chimeric polypeptide of the invention), the membrane vesicles described in the application (in particular membrane vesicles of the invention) or the compositions described in the application (in particular the compositions of the invention) are administered to the host susceptible to exposure to a pathogenic organism or a pathogenic agent and/or susceptible of developing a tumor or any other pathologies, in particular a functional or metabolic deficit, before the appearance of any clinical signs or symptoms of the disease. Prophylactic administration may be carried out before said host is exposed to the organism or to the pathogenic agent responsible for the infection, or at the time of exposure. Such prophylactic administration acts to prevent and/or reduce the severity of any subsequent infection. "Prophylaxis" in the context of the present application also encompasses total prevention of an infection or a cancer or any other pathology.

The term "treatment", means the therapeutic effect produced in a host by the chimeric polypeptides described in the application (in particular the chimeric polypeptide of the invention), the polynucleotides described in the application (in particular the polynucleotide of the invention), the membrane vesicles described in the application (in particular the membrane vesicles of the invention), or one of the compositions described in the application (in particular the compositions of the invention), when they are administered to said host at the time of exposure to a pathogenic organism or agent, after exposure or after the appearance of clinical signs or symptoms of the infection or after the appearance of a tumor. When the active substances of the invention are administered to a host after contamination by a virus, they may be administered during the primo-infection phase, during the asymptomatic phase or after the appearance of clinical signs or symptoms of the disease.

The term "treatment" includes any curative effect obtained by means of an active substance of the invention, as well as improvement in the clinical signs or symptoms observed in the host (human or non-human), as well as an improvement in the condition of the host. Thus, the term "treatment" in particular encompasses slowing, reduction, interruption as well as stopping a viral, bacterial or parasitic infection or the growth of tumors or any other diseases and/or the deleterious effects of infection or the appearance of a tumor or any other pathologies; a treatment does not necessarily demand the complete elimination of all clinical signs of infection or of the tumor and/or all symptoms of the disease, nor the complete elimination of virus, bacteria, parasites or tumor cells, or functionally deficient cells.

The active substances of the invention may thus be administered to a host who risks exposure to a pathogenic organism or agent and of developing an infection or a tumor (prophylaxis), or after exposure of the host to a pathogenic organism or agent, in particular after manifestation of the first clinical signs or symptoms of disease, for example after the specific proteins or antibodies of a virus, of bacteria, of parasites or of a tumor have been detected in the blood of the host (treatment).

The invention also provides a method for preventing and/or treating a viral, bacterial or parasitic infection or a tumor or any other pathologies, said method comprising at least one step for in vivo administration, to a host requiring it, of a chimeric polypeptide, of one or more membrane vesicle(s) of the invention (in particular one or more exosome(s) of the invention), of a polynucleotide of the invention or of an immunogenic composition of the invention. In particular, said treatment method is appropriate for and intended to elicit or promote, in vivo, in said host, a humoral and/or cellular response against the tumor, virus, bacterium or parasite from which the peptide or polypeptide of interest derives.

The terms "administration" and "administer" as used in the present application include any administration, irrespective of the selected administration pathway.

The administration routes and posologies depend on a variety of parameters, for example the condition of the host, the type of infection and the severity of the infection to be treated or the size of the tumor.

The chimeric polypeptide, like the one or more membrane vesicle(s) of the invention (in particular one or more exosome(s) of the invention), the polynucleotide of the invention or a composition of the invention are capable of being administered to a human or non-human host in the dry, solid form (in particular a tablet, powder, gelule, pill, granule, suppository, polymer capsule or compressed tablet, and more precisely a rapid release tablet, a gastroresistant tablet or a slow release tablet), in the gel form or in the form of a solution or a liquid suspension (in particular a syrup, injectable, infusible or potable solution, nebulizers, microvesicles, liposomes) or in the form of a patch. These compounds may also be in the form of dry doses (powder, lyophilisate, etc.) to be reconstituted upon use, using an appropriate diluent. Further, they may be packaged for administration in the form of a single dose (monodose) or a multiple dose (multidose).

The active substances of the invention may be formulated for enteral, parenteral (intravenous, intramuscular or subcutaneous), transcutaneous (or transdermal or percutaneous), cutaneous, oral, mucosal, in particular buccal-mucosal, nasal, ophthalmic, otological (into the ear), vaginal, rectal, or intragastric, intracardiac, intraperitoneal, intrapulmonary or intratracheal administration.

In order to increase the beneficial effects of the compositions of the invention (in particular the immunogenic compositions of the invention), it may be possible to carry out administration in the form of several successive administrations, repeated one or more times, after a particular time interval. They may also be administered with a second therapeutic agent, in particular an antiviral, antibacterial, antiparasitic or anti-tumoral agent.

In the context of use for vaccination, it may also be preferable to immunize a host, initially with an immunogenic composition based on a polynucleotide of the invention, in particular with a DNA vaccine of the invention, then secondly with membrane vesicles of the invention, an immunogenic composition based on said vesicles or an immunogenic composition the active principle of which is a chimeric polypeptide of the invention or one or more fragment(s) thereof (said chimeric polypeptide or its fragment(s) possibly being obtained by purification or by chemical synthesis).

Alternatively, it may also be preferable to immunize a host, initially with the membrane vesicles of the invention or an immunogenic composition based on said vesicles, then secondly with an immunogenic composition based on a polynucleotide of the invention, in particular with a DNA vaccine of the invention.

The immunogenic compositions based on a polynucleotide of the invention and in particular the DNA vaccines of the invention are preferably administered to a host intramuscularly or sub-cutaneously, using either a needle and a syringe or a needleless injector, in particular a compressed air gun that can propel gold, tungsten or platinum microbeads loaded with DNA into the cells of a host ("biolistic" gun or gene gun), for example the "Helios® Gene Gun System" from BioRad.

The quantity of active principle administered to a human or non-human host is a therapeutically effective quantity, i.e. an active, sufficient, quantity in posologies and for periods of time that are necessary to obtain a significant effect and in particular to provide a significant benefit to the host in the context of administration for the purposes of prophylaxis or for treatment as defined in the present application. A therapeutically effective quantity is also a quantity for which the beneficial effects outweigh any toxic or deleterious effect of the active principle or principals. Such a quantity may correspond to a quantity sufficient to inhibit viral replication, bacterial proliferation or the growth of a tumor in a significant manner or to cause any existing infection caused by the pathogenic agent or organism to disappear, reduce or improve. The therapeutically effective quantity varies as a function of factors such as the state of infection, age, sex or weight of the host. Posological regimes may be adjusted to obtain an optimum therapeutic effect. The present invention also concerns a method for obtaining membrane vesicles in vivo, in particular exosomes, characterized in that it comprises a step for administration of a chimeric polypeptide of the invention (and if appropriate an additional chimeric polypeptide), one or more membrane vesicle(s) of the invention, in particular one or more exosome(s) of the invention (and if appropriate one or more additional membrane vesicle(s)), a polynucleotide of the invention (and if appropriate an additional polynucleotide), or a composition of the invention (and if appropriate an additional composition), to a host (human or non-human). This method may in particular be carried out in the context of a method for the prophylaxis and/or treatment of a tumor or of an infection by a pathogenic organism or by a pathogenic agent, in particular a bacterial, viral or parasitic infection.

The present invention also concerns a method for the in vitro production of membrane vesicles and in particular exosomes comprising a peptide or a polypeptide of interest and/or a degradation product of this peptide or a polypeptide of interest, this degradation product possibly, if appropriate, being associated with a molecule of the major histocompatibility complex. Said method comprises the following steps:

a) introducing, into an exosome-producing cell, one or more polynucleotide(s) of the invention, which code(s) for a polypeptide comprising said peptide or polypeptide of interest, or bringing an exosome-producing cell into contact with one or more membrane vesicle(s) of the invention, which comprise(s) a polypeptide comprising said peptide or polypeptide of interest and/or a degradation product of this polypeptide, or with a composition based on such vesicles;

b) culturing said exosome-producing cell;

c) recovering membrane vesicles and in particular exosomes produced by said exosome-producing cell.

In accordance with a particular embodiment, the exosome-producing cell is a cell of the HEK293 line, or a derivative line, or a cell of the immune system. In particular, the cell of the immune system may be selected from mastocytes, lymphocytes, in particular T and B lymphocytes, and dendritic cells. The cell of the immune system is preferably a dendritic cell, for example a Langerhans cell.

In accordance with a particular embodiment, step a) consists of bringing one or more membrane vesicle(s) of the invention, in particular one or more exosome(s) of the invention, into contact with a dendritic cell.

In accordance with a particular embodiment, said method further comprises an intermediate step between steps a) and b), during which the cell is selected and/or stimulated to induce and/or enhance secretion of the exosomes or to obtain exosomes having defined qualities, in particular to induce a specificity into the composition of the exosomes in certain cellular proteins, for example the protein ICAM.

In accordance with a particular embodiment, the introduction of one or more polynucleotide(s) of the invention into an exosome-producing cell in step a) is accomplished by transfection or by transduction.

In accordance with a particular embodiment, step c) is accomplished by purifying the membrane vesicles and in particular the exosomes from a culture supernatant of the exosome-producing cell by differential centrifuging, by ultrafiltration, by adsorption onto a support, or by any other method.

The membrane vesicles and in particular the exosomes obtained by this method also form part of the invention.

The present invention also concerns the use of one or more membrane vesicle(s) of the invention (and, if appropriate, one or more additional membrane vesicle(s)), or of a composition based on membrane vesicle(s) of the invention (and, if appropriate, an additional composition), to produce antibodies directed against the peptide or polypeptide of interest, these antibodies being intended for use in diagnostics or in research. The present invention also provides a method for the preparation of a polyclonal serum directed against one or more antigenic peptide(s) or polypeptide(s) of interest expressed at the surface of membrane vesicles, in particular exosomes, said method comprising the following steps:

a) administering to a non-human animal, if appropriate repeatedly, membrane vesicles of the invention, an immunogenic composition of the invention or a polynucleotide of the invention, associated or not associated with an adjuvant; and b) recovering antibodies that are formed, which are capable of recognizing the antigenic peptide(s) or polypeptide(s) of interest.

In accordance with a particular embodiment, step a) is followed by a step for sacrificing the non-human animal.

The present invention also provides two methods for the preparation of monoclonal antibodies directed against one or more antigenic peptide(s) or polypeptide(s) expressed at the surface of or in membrane vesicles, in particular exosomes. The first method comprises the following steps:

a) fusing, with myeloma cells, spleen cells obtained from a host (human or non-human), for example a Balb/c mouse, to which membrane vesicles of the invention, an immunogenic composition of the invention or a polynucleotide of the invention have been administered, if appropriate in association with an adjuvant and if appropriate by repeated administration;

b) culturing and selecting hybridomas under conditions enabling the production of antibody;

c) recovering monoclonal antibodies directed against the antigenic peptide(s) or polypeptide(s) of interest.

The second method for preparing monoclonal antibodies comprises the following steps:

a) immortalizing antibody-producing cells, for example lymphocytes or lymphoblasts, from hematopoietic cells, more particularly from blood cells, obtained from a host (human or non-human), for example a Balb/c mouse, to which membrane vesicles of the invention, an immunogenic composition of the invention or a polynucleotide of the invention have been administered, if appropriate in association with an adjuvant and if appropriate by repeated administration;

b) culturing and selecting immortalized cells under conditions enabling the production of antibody;

c) recovering monoclonal antibodies directed against the antigenic peptide(s) or polypeptide(s) of interest.

In particular, the invention can be used to produce cytosolic antibodies.

Immortalizing antibody-producing cells in step a) may in particular be accomplished by infecting these cells with an immortalizing virus. This immortalizing virus may be a herpes virus, for example the Epstein-Barr virus. This immortalization may also be accomplished by modification of the genome of the antibody-producing cells with an immortalizing component. This immortalizing component may be a viral component, for example from a herpes virus, or a cellular gene, for example the gene for telomerase.

The non-human animal to which the membrane vesicles, an immunogenic composition or a polynucleotide of the invention have been administered in the context of a method for preparing a polyclonal serum or methods for preparing monoclonal antibody may in particular be a rodent (in particular a mouse, for example a Balb/c mouse, a rat, a hamster or a rabbit), a bird, in particular a chicken, or a mule.

In accordance with a particular embodiment of the two methods for the preparation of monoclonal antibodies of the invention, the spleen cells or the antibody-producing cells of step a) are obtained from a non-human host after a step for sacrificing said non-human animal.

If necessary, the monoclonal or polyclonal antibodies produced by the methods for the preparation of antibodies of the invention may be "humanized", i.e. modified by genetic engineering so as to replace the maximum number of constant fragments Fc of the original species by human fragments.

The present invention also concerns the use of a chimeric polypeptide of the invention (and, if appropriate, of an additional chimeric polypeptide), of one or more membrane vesicle(s) of the invention (and, if appropriate, of one or more additional membrane vesicle(s)), or of a composition of the invention (and if appropriate of an additional composition), for the detection (in particular in vitro) of specific partners that are capable of interacting with said peptide or a polypeptide of interest or with a fragment of said peptide or a polypeptide of interest. The present application also provides a method for in vitro screening of molecules or a method for selecting cells producing molecules interacting with a peptide or a polypeptide of interest or with a fragment of said peptide or a polypeptide of interest, said method comprising:

a) bringing membrane vesicles of the invention into contact with one or more molecules capable of interacting with said peptide or polypeptide of interest present in the additional chimeric polypeptide;

b) detecting any interaction between said peptide or polypeptide of interest or a fragment of said peptide or polypeptide of interest and said molecule or molecules.

The interactions between said peptide or polypeptide of interest and any partner may be demonstrated in vitro using any technique that can provide evidence of protein interactions, in particular between a protein and its ligand, for example by using co-immunoprecipitation experiments, for example ELISA, for example by flow cytofluorometry, for example by PAGE-SDS electrophoresis or by <<Western" type transfer (Western Blot), as well as using any high throughput screening technique that can highlight protein interactions, in particular between a protein and its ligand, for example techniques measuring modifications in inositol phosphates, or in cAMP, or in calcium, or energy transfers (for example the FRET or BRET technique) between molecules or between two domains of molecules.

In accordance with a particular embodiment, the membrane vesicles used in step a) of the screening method of the invention are such that at least one peptide or polypeptide of interest or at least one of their fragments is exposed, in part or in its entirety, on the outside of said membrane vesicle. Said peptide or polypeptide of interest may in particular be a receptor with multiple transmembrane domains, for example the receptor CXCR4, or a receptor comprising a single transmembrane domain, for example the CD4 or EGF-R1 receptor.

Finally, the present invention also provides a kit comprising a polynucleotide of the invention and instructions for use and, if appropriate, an additional polynucleotide.

Other characteristics and advantages of the present invention will become apparent from the following examples and figures.

DESCRIPTION OF THE DRAWINGS

FIG. 6: Checking identity of DNAs after enzymatic digestion.—Differentiation between mutants of CD8-CD™. A: differentiation of pX2 mutants AAC and pX2 CCA. B: mutual differentiation of mutants X2.

BLV antibody was used diluted to 1/200. The secondary anti-rabbit IgG antibody coupled to peroxidase was used diluted to 1/2000. B. The sizes of the bands observed corresponded to the expected sizes and are noted on the right hand side.

Figure 30:
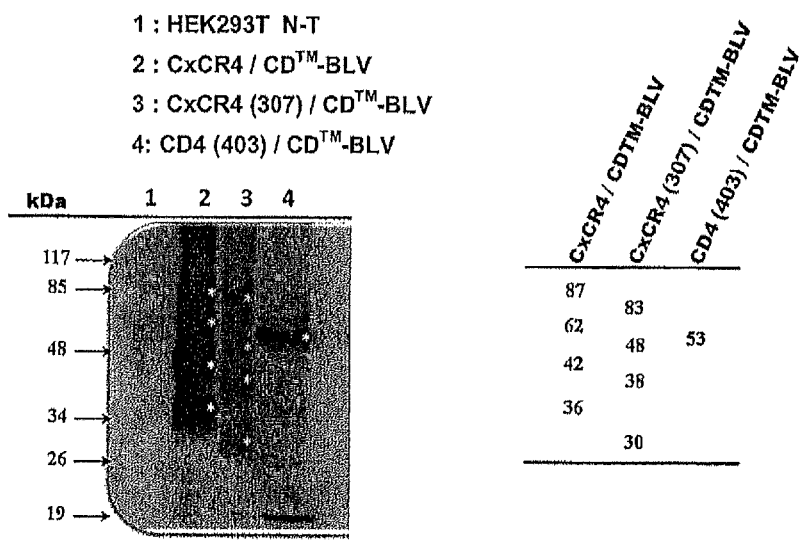

FIG. 30: A. Western Blot analysis of anti-CD™-BLV carried out on the exosomal protein extracts produced by HEK293T cells not transfected (N-T) or transfected with the pLPCX expression vectors containing the three constructs coding for the three chimeric proteins. The primary rabbit anti-CD™-BLV antibody was used diluted to 1/200. The secondary anti-rabbit IgG antibody coupled to peroxidase was used diluted to 1/2000. B. The sizes of the bands observed corresponded to the expected sizes and are noted on the right hand side.

Figure 31:
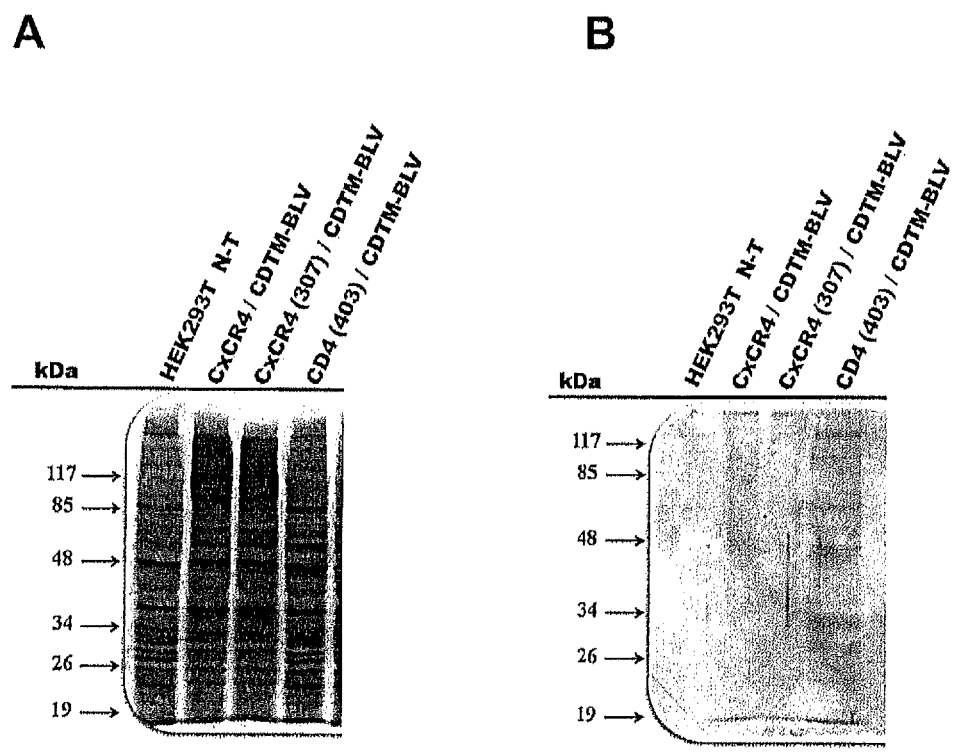

FIG. 31: Coomassie Blue staining of protein fingerprints of various cellular (A) and exosomal (B) extracts.

FIG. 32: Sequence of the Src-SNAP-DCTM gene annotated for the restriction sites bordering the 3 fused DNA fragments and sequence of the SSC protein coded by this gene (SEQ ID NOs. 121 and 122).

FIG. 33: Sequence of the D-SNAP-DCTM gene annotated for the restriction sites bordering the 3 fused DNA fragments and sequence of the DSC protein coded by this gene (SEQ ID NOs. 123 and 124).

Figure 34:
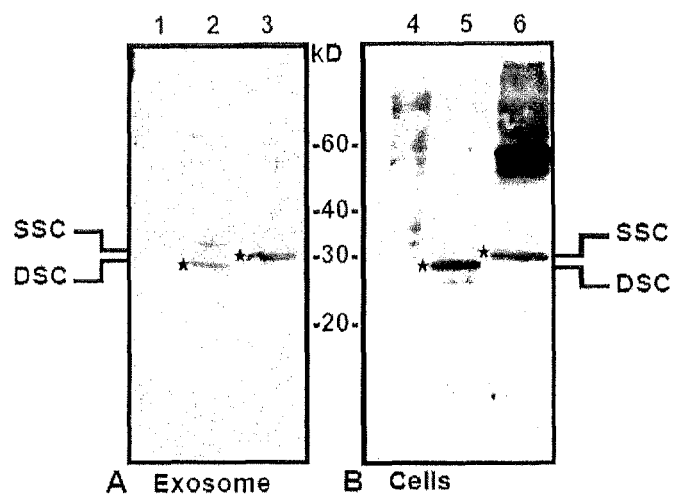

FIG. 34: Demonstration of targeting in the exosomes of the SSC and DSC proteins. HEK 293 cells ($5 \times 10^5$ cells) were transfected in the presence of 2 µL of JetPrime (PolyPlus transfection) with 1 µg of eukaryotic DNA expression vector (pcDNA 3.1) containing the chimeric genes Src-SNAP-CDTM (tracks 3 and 6), or D-SNAP-CDTM (tracks 2 and 5) or deprived of these genes (tracks 1 and 4). The proteins of exosomes (A) secreted in the medium and the cells were separated by gel electrophoresis (PAGE-SDS) and transferred onto Immobilon membrane (Millipore). The Western Blots were revealed using a rabbit anti-CDTM serum and a secondary anti-rabbit IgG antibody tagged with peroxidase: A) analysis of 2 µg of exosomes, B) analysis of 20 µg of cell extract.

EXAMPLES

Example 1

Materials and Methods

I. Preparations of Plasmid DNAs:
A. Transformation of Bacteria:
Competent DH5α bacteria (200 µL) are transformed by thermal shock with 12.5 ng of each of the 13 DNAs studied coding for the wild type or mutant CD™ of BLV virus, as well as by a plasmid deprived of the insert (pLPCX) acting as a negative control.

The bacteria are then spread onto a LB/Agar medium containing 50 µg/mL of ampicillin, a 37° C. for a period of 16 h. They are then stored at 4° C.

B. Pre-Culture and Culture of Bacteria:
One colony of each type of bacteria is then pre-cultured in 3 mL of LB medium containing 100 µg/mL of ampicillin, at 37° C. with agitation, for a period of approximately 8 h.

Each pre-culture, diluted to 1/200, serve to inoculate two flasks each containing 250 mL of LB/Amp (100 µg/mL). Incubation is carried out at 37° C., with agitation, for a period of 12 to 16 h.

C. STET Maxipreparation:
The cultures obtained are centrifuged (GR 412, Jouan) for 20 min at a speed of 3600 rpm and at a temperature of 4° C. The pellets are taken up in 25 mL of STET buffer (Sucrose 8%, Triton X100 5%, Tris HCl pH 8, 50 mM, EDTA 50 mM) to which 500 µL of lysozyme (10 mg/mL; Sigma) and 250 µL, of RNase (2 mg/mL; Sigma) have been added. The tubes are then incubated for 10 min at 100° C. then centrifuged at 16000 rpm for a period of 30 min. The supernatants obtained are incubated for 45 min at 65° C. in the presence of 1 mg/mL of proteinase K (Amresco). The supernatants are removed and the DNA is precipitated with 0.15 volume of sodium acetate (AcNa) 3M, pH 6 and 0.6 volume of isopropanol. The solutions are centrifuged (Aventi 30, Beckman) at 4° C. for a period of 15 min at 15000 rpm. The pellets obtained are washed with 10 mL of ethanol before being centrifuged again using the preceding parameters. The nucleic acids obtained are dried and taken up in 2 mL of TE 1× and stored at 4° C.

The presence of super-coiled DNA is verified, for each Maxipreparation product, by electrophoresis of 0.2 µL and 1 µL of the products by electrophoresis on 0.8% agarose gel.

D. Column Purification:
The STET Maxipreparations enable the obtention of large quantities of plasmids, but the purity needs to be improved. To this end, we purified each of the 14 plasmids by passing them twice over AX100 columns (Kit Nucleobond PC 100, Macherey Nagel). After precipitation with isopropanol, the purified plasmids obtained were taken up in 500 µL of TE1X and stored at 4° C.

The presence of super-coiled DNA is then verified by agarose gel electrophoresis (0.8%) for each eluate obtained as well as for the fraction not retained on the columns (FT=flow-through).

The concentration of DNA in the solutions obtained is evaluated by spectrophotometry, at a wavelength of 260 nm.

E. Taking Aliquots and Precipitation with EtOH:
Aliquots of 50 or 100 µg of each DNA type were placed in tubes then precipitation is carried out with ethanol (EtOH) and NaCl, in a laminar flow hood, in order to sterilize the plasmids. The pellets obtained are taken up into 200 µL of TE1X per 100 µg of plasmids, i.e. a concentration of 500 ng/µL. The presence of DNA in the aliquots is verified using 0.8% agarose gel electrophoresis.

F. Spectrophotometric Assays of Aliquots Obtained:
The aliquots are assayed by spectrophotometry at a wavelength of 260 nm. The samples are diluted to 1/50 and were assayed in a final volume of 500 µL.

G. Enzymatic Digestions
The identity of each plasmid is checked by digesting 20 ng of each of them with restriction enzymes (New England Biolabs): the Hind III/Not I pair, Xba I, Aat II, Pac I, Sfo I. The plasmids are differentiated according to the number of bands obtained and their molecular weight, after agarose gel electrophoresis (0.8%) of each digestion product.

II. Analysis of the Expression of Chimeras
A. Cell Culture:
The HEK293 cells (Human Embryonic Kidney cells) are cultivated in a DMEM medium (Dulbecco's modified Eagle's medium), supplemented with 10% fetal calf serum (FCS) and 20 µg/mL of gentamicin, at 37° C. in 5% $CO_2$.

B. Transfection:
For the transfections, $5 \times 10^5$ cells are seeded in 2 mL of medium per 9.6 $cm^2$ well (6-well plates). After incubation overnight at 37° C. in 5% $CO_2$, the medium is replaced with complete DMEM without antibiotics.

The cells are then transfected by a polyplex formed by complexing, in a NaCl (0.15 M) buffer, 6 µL of Jet PEI (Qbiogen) and 3 µg of each nucleic acid to be tested; a plasmid expressing LacZ acts as the positive control for the transfection. After 24 h of incubation at 37° C. in 5% CO$_2$, the medium is eliminated and replaced by complete DMEM with 20 μg/mL of gentamicin. Optimum expression of plasmids is obtained 48 h after the onset of transfection.

In certain cases, in order to analyze the importance of vesicular transport in degradation and targeting of CD™, we used vesicular transport inhibitors, namely bafilomycin and Ly 294002. 32 h after transfection, each inhibitor is added to the culture medium in a concentration of 0.5 μM for the bafilomycin and 10 μM for Ly 294002.

C. Protein Extraction:

48 h after transfection, the cells are lysed with 0.5% THE-NP40 buffer to which 0.1 mM of PMSF had been added. After clarification by centrifuging (14000 rpm, 15 min, 4° C.; Eppendorf 5417R), the lysates are assayed by spectrophotometry (at 595 nm) using Bradford's technique.

For each sample, 200 μg of proteins were removed and made up with lysis buffer to a final volume of 30 μL to which 10 μL of sample buffer 4× had been added (CB 4×: NaOH 200 mM, EDTA 20 mM, SDS 2%, bromocresol green 0.05%, glycerol 10%).

D. Preparation of Exosomes:

Before lysing the cells, the culture media are recovered and pre-centrifuged at 10000 rpm for 20 min at a temperature of 4° C. (Aventi 30, Beckman). The supernatants obtained are then ultracentrifuged (Optima LE-80K, Ti 50 rotor, Beckman) at 100000 g for a period of 2 h at a temperature of 4° C. The pellets obtained are taken up in 100 μL of CB 1×.

We have also analyzed the exosomes by sucrose density gradient sedimentation. The pellets obtained after ultracentrifuging of the culture media are then taken up in 100 μL of a 0.25 M sucrose solution.

The vesicles are then deposited on a sucrose gradient prepared with 8 layers (of 1.2 mL) with different densities (in molarities): 0.5/0.75/1/1.25/1.5/1.75/2/2.5. The tubes are then centrifuged (Optima LE-80K, SW 41 rotor, Beckman) at 39000 rpm for a period of 16 h, at a temperature of 4° C.

After centrifuging, the gradient is removed in 700 μL fractions. The proteins are then precipitated by adding the same volume of 30% TCA. The tubes are stored for 2 h at 4° C. then centrifuged (Eppendorf, 5417R) at a temperature of 4° C. for a period of 20 min at 13000 rpm. The pellets are taken up in 500 μL of acetone then centrifuged again as before.

The pellets obtained are taken up in 80 μL of CB1X then analyzed by migration on acrylamide-SDS gel and Western Blot.

E. Western Blot and Immunoprecipitation:

The protein samples obtained are analyzed by Western Blot: after migration and separation on acrylamide gel (12.5%), the proteins are transferred onto hydrophobic PVDF membrane (Immobillon-P, Millipore).

The presence of mutants of the TM protein is revealed by immunotagging with the aid of the following antibodies:
  Primary antibody: anti-rabbit CD™ BLV antiserum (Dilution 1/200).
  Secondary antibody: anti-rabbit IgG tagged with peroxidase (Dilution 1/5000; Jackson Immuno Research, JIR)

The presence of receptors for transferrin is revealed by immunotagging using the following antibodies:
  Primary antibody: mouse anti-human TFr IgG (Dilution 1/200; Zymed)
  Secondary antibody: anti-mouse IgG (Dilution 1/5000; JIR)

In order to selectively increase the concentration of the protein being studied, we also carried out immunoprecipitations on the protein lysates prior to gel migration. After normalizing the quantities of proteins, the lysate is adsorbed onto sepharose 6B in order to eliminate non-specific reactions and the immunoprecipitation is carried out with the protein sepharose 6A in the presence of 2.5 μg of the following antibodies:
  Primary antibodies:
    mouse anti-mouse CD8 IgG (19/178) (JIR)
    rat anti-mouse CD8 IgG (53/672) (JIR)
  Secondary antibodies:
    anti-mouse IgG (JIR)
    anti-rat IgG (JIR)

The pellets obtained are then taken up in 70 μL of CB 1.5×.

III. Localization by Immunofluorescence

A. Preparation of Slides.

Coverslip type slides are sterilized with absolute EtOH in a laminar flow hood then placed in 1.9 cm$^2$ wells (24-well plates) before being coated with poly-L-Lysine (25 μg/mL, Sigma) for a period of 1 h at 37° C. After washing with PBS, the slides are stored at 4° C. in 1 mL of PBS.

B. Cell Culture and Transfection.

HEK293 cells are cultivated and transfected using the method described in the section "Analyses of chimeric expression". 24 h after transfection, the cells are taken up in 35 mL of complete DMEM, then distributed into 1.9 cm$^2$ wells (24-well plates) containing the pre-sterilized slides coated with 1 mL of cellular dilution per well. The cells that are thus placed under culture are incubated for 24 h at 37° C., in 5% CO$_2$.

C. Fixing and Permeabilizing.

The cells are then fixed for 30 min with a solution of formaldehyde (4%) then permeabilized with Triton X-100 (0.2% final). After 3×10 min rinses with PBS, the slides are stored with 1 mL of PBS, at 4° C.

D. Tags for Immunofluorescence.

The various antibodies available meant that we could test several tags for localization by immunofluorescence:

CD8 Tags:

N° 1: mouse IgG/anti-mouse CD8 (19/178) (JIR)+anti-mouse IgG FITC (JIR)

N° 2: mouse ascites/anti-mouse CD8 (19/178) (JIR)+Anti-mouse IgG FITC (JIR)

N° 3: rat IgG/anti-mouse CD8 (53/672) (JIR)+anti-rat IgG FITC (JIR)

N° 4: rat IgG (53/6.7)/anti-mouse CD8 FITC (Pharmingen)

Tags for Intra-Cellular Compartments:

N° 5: mouse IgG/anti-human CD63 (Lamp3) (Zymed)+anti-mouse IgG Cy3 (Sigma)

N° 6: mouse IgG/anti-human Lamp1+anti-mouse IgG Cy3 (Sigma)

N° 7: mouse IgG/anti-human Tf2 (Zymed)+anti-mouse IgG Cy3 (Sigma)

N° 8: rabbit IgG/anti-caveolin (BD)+anti-rabbit IgG TRITC (JIR)

Results

Knowledge regarding the exosome formation process is partial. Similarly, the functions associated with the cytoplasmic domain of Env are not well characterized. The present study is based on the hypothesis that the bovine leukemia virus (BLV) model is a good tool for studying the phenomena of exosome formation and the formation of viral particles and the cytoplasmic domain of the TM protein (CD™) of BLV is a potentially interesting tool in the development of vaccination by "exosome display".

In order to evaluate this potential and in order to characterize the functions responsible for targeting the TM protein of BLV, and more particularly the role of palmitylated or non-palmitylated cysteine residues, we developed a number of vectors that enabled expression in eukaryotic cells of chimeric transmembrane proteins comprising the ectodomain of the mouse CD8 protein and the CD™ domain (CD8-CD™ chimeric proteins). Wild type CD8CD™ chimeras as well as mutated CD8-CD™ chimeras were expressed.

The mouse CD8 ectodomain in a human cell is a neutral element that does not interfere with the cellular receptors. The chimeras used thus guarantee us the absence of interactions between the ectodomain of the proteins and the cellular structures.

In consequence, these chimeras can be used to specifically study the cytoplasmic and transmembrane domains of the TM protein, avoiding the phenomena caused by the ectodomain of the TM protein and by the SU protein with which it is associated.

Figure 1:
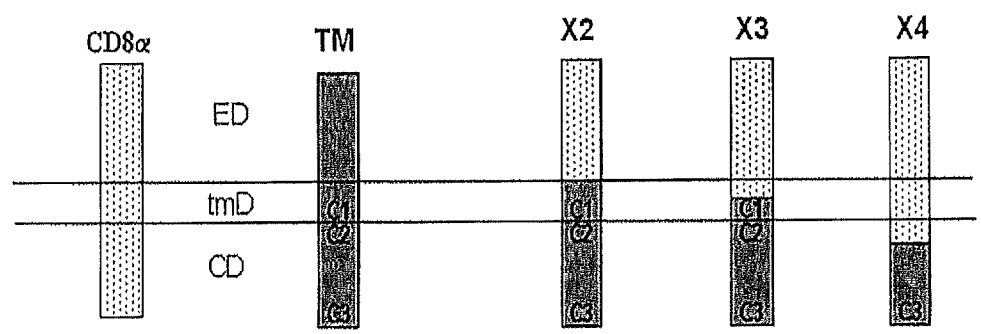
FIG. 1: Representation of the various types of CD8-CD™ constructs studied. Construct X2 (sequence SEQ ID NO. 79 and SEQ ID NO. 80): the ectodomain (ED) of CD8 is fused with the transmembrane (tmD) and cytoplasmic (CD) domains of the TM protein of BLV. This construct conserves the two palmitylation sites Cys 1 and Cys 2 as well as the non-palmitylable cysteine residue regulator (Cys 3) of the TM protein of BLV. Construct X3 (sequence SEQ ID NO. 81 and SEQ ID NO. 82): ED and a portion of tmD of CD8 are fused with a tmD portion of BLV and the whole of CD™ BLV. The first 15 residues of the BLV tmD have thus been amputated. This construct conserves the two palmitylation sites (the cysteine residues in positions 153 and 158) as well as the non-palmitylable cysteine residue regulator (the cysteine residue in the C-terminal position; Cys 3) of the TM protein of BLV. Construct X4 (sequence SEQ ID NO. 83 to SEQ ID NO. 86): The major portion of CD™ BLV is conserved. In this construct, the transmembrane domain of mouse alpha CD8 is linked by a linker with sequence "RSR" to the CD domain of the TM protein of BLV. This construct only comprises the non-palmitylable cysteine residue regulator (Cys 3) of the TM protein of BLV.
Figure 2:
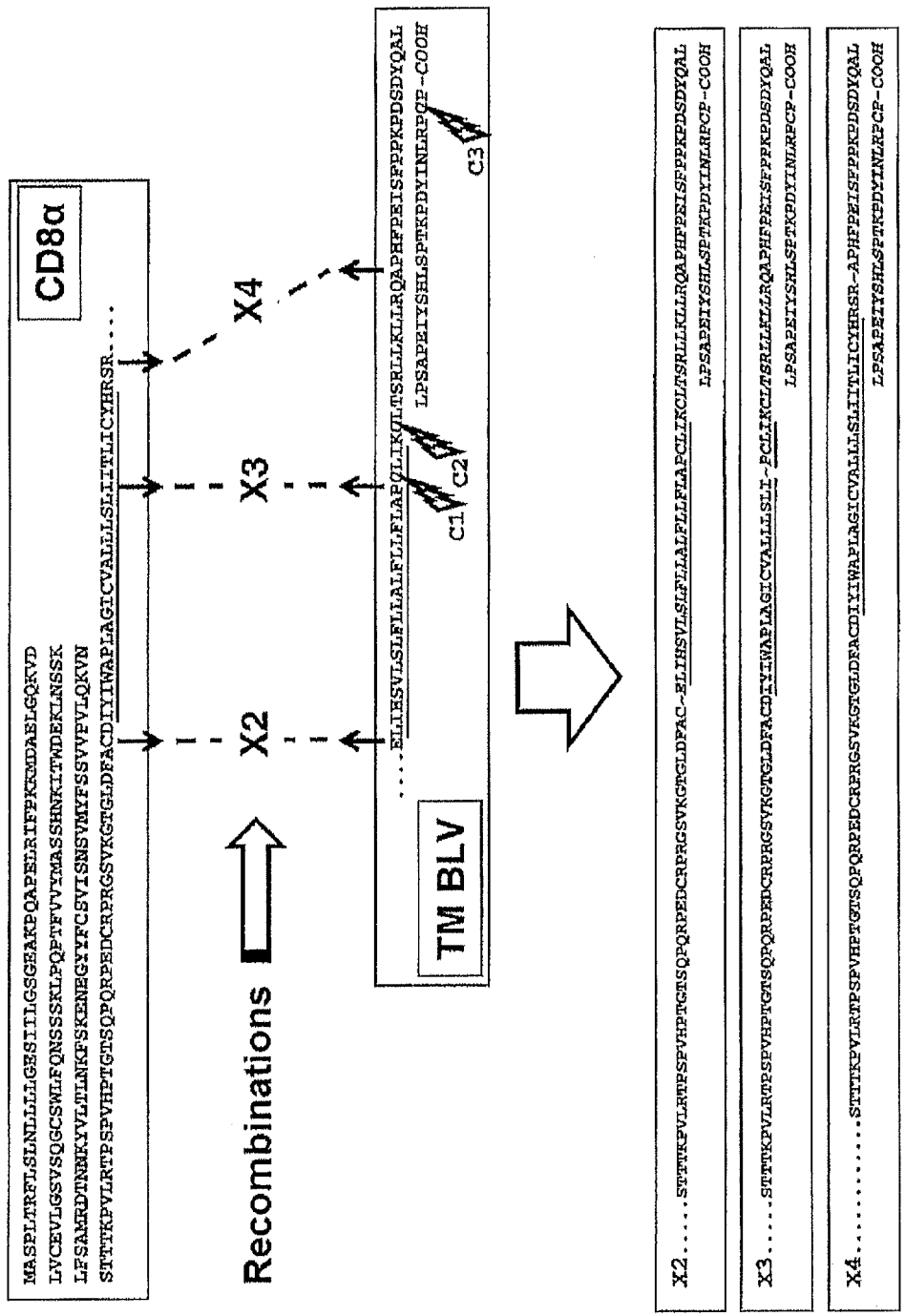
FIG. 2: Overview of the sequences for the chimeric proteins obtained from the mouse CD8 alpha protein and from the TM protein of BLV. The residues that are underlined correspond to residues of the transmembrane helices of the CD8 alpha and TM proteins. The three cysteine residues of the TM protein of BLV that have undergone a mutation (substitution with an alanine residue) are indicated by C1, C2 and C3. The chimeric proteins created correspond to the constructs X2 (sequence SEQ ID NO. 79 and SEQ ID NO. 80), X3 (sequence SEQ ID NO. 81 and SEQ ID NO. 82) and X4 (sequence SEQ ID N0.83 to SEQ ID NO. 86).

Three types of constructs were used (see FIGS. 1 and 2). From these constructs, we developed different pLPCX expression vectors enabling the expression of wild type or mutated CD8-CD™ in the cysteine residues 1, 2 and 3 (abbreviated to: CCC). The cysteine residues are thus replaced or not replaced by alanine residues that cannot be palmitylated.

The wild type or mutated CD8-CD™ proteins studied were:
1: pX2 CCC (wild type phenotype)
2: pX2 ACC
3: pX2 CAC
4: pX2 AAC
5: pX2 CCA
6: pX2 ACA
7: pX2 CAA
8: pX2 AAA
9: pX3 CCC (wild type phenotype)
10: pX3 CAC
11: pX4-C (wild type phenotype)
12: pX4-A
13: pX4 stp (pX4 stp is composed only of ED, tmD and small portion of the CD™ of CD8).

By means of targeting of the TM protein, these constructs enabled us to study the following: the consequences of mutation of the cysteine residues, the importance of the integrity of the transmembrane domain of the TM protein, and the importance of the cytoplasmic domain of the TM protein (CD™).

I. Preparation of Plasmid DNAs:

Firstly, we produced large quantities of each of our 13 DNAs as well as an insert-free vector (pLPCX) acting as a negative control. After culture of bacteria transformed by our various plasmids, the DNAs obtained were purified successively using the STET method then on a column. The identity of the plasmids obtained was then checked by enzymatic digestion.

Figure 3:
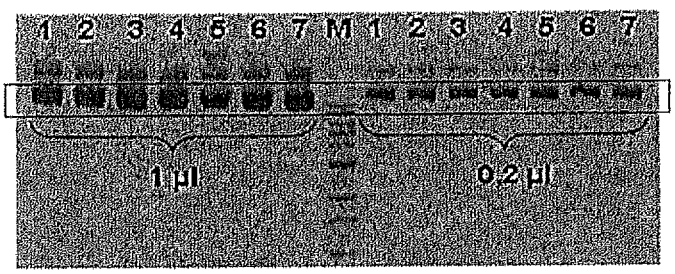
FIG. 3: Preparations of DNAs by the STET method. The numbers 1 to 7 correspond to the samples numbers of the STET products. "M" represents the size marker. The bands corresponding to super-coiled plasmid DNA are in a box.

A. Preparations of DNAs by the STET Method:

In order to verify the integrity of the plasmid DNAs and the yield of the STET preparations, we carried out a migration of 1 µL and 0.20 µL of each of them on agarose gel (0.8%; see FIG. 3). Non-degradation of DNAs was demonstrated by the presence of distinct bands of super-coiled DNA of homogeneous sizes.

Figure 4:
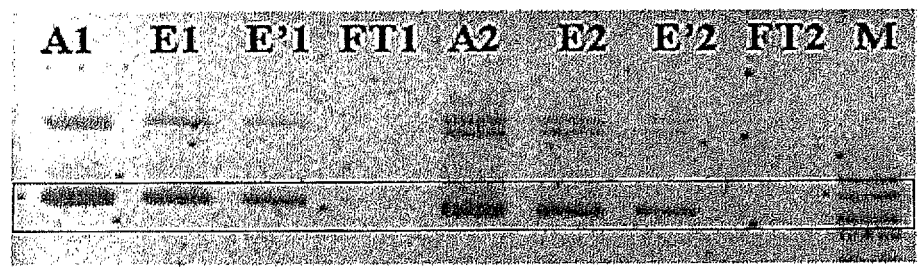
FIG. 4: Checking the presence of DNAs in the column purification products. The bands corresponding to super-coiled plasmid DNA are in a box. A: DNA obtained by the STET method and deposited on the column. E and E': Fractions retained on the column then eluted, FT: Non-retained fraction, M: Size marker.

B. Checking the Presence of DNAs in the Column Purification Products:

The DNAs obtained by the STET method are purified on columns; the fractions that were retained then eluted as well as the fractions that were not retained are then analyzed by gel electrophoresis in order to verify the integrity of the purified DNAs obtained. The gel seen in FIG. 4 shows us that super-coiled DNA is indeed present in the pure fractions eluted from the columns (E and E'), but is undetectable in the non-retained fractions (FT).

C. Spectrometric Assays of Aliquots and Adjustment of Concentrations of DNAs After Enzymatic Digestion:

The purified DNAs are then assayed using a spectrophotometer. The concentrations obtained vary, between 149 µg/mL and 584 µg/mL, as a function of the aliquots. After precipitation with EtOH, the DNAs of the aliquots are taken up in TE1X and adjusted to the same concentration.

Figure 5:
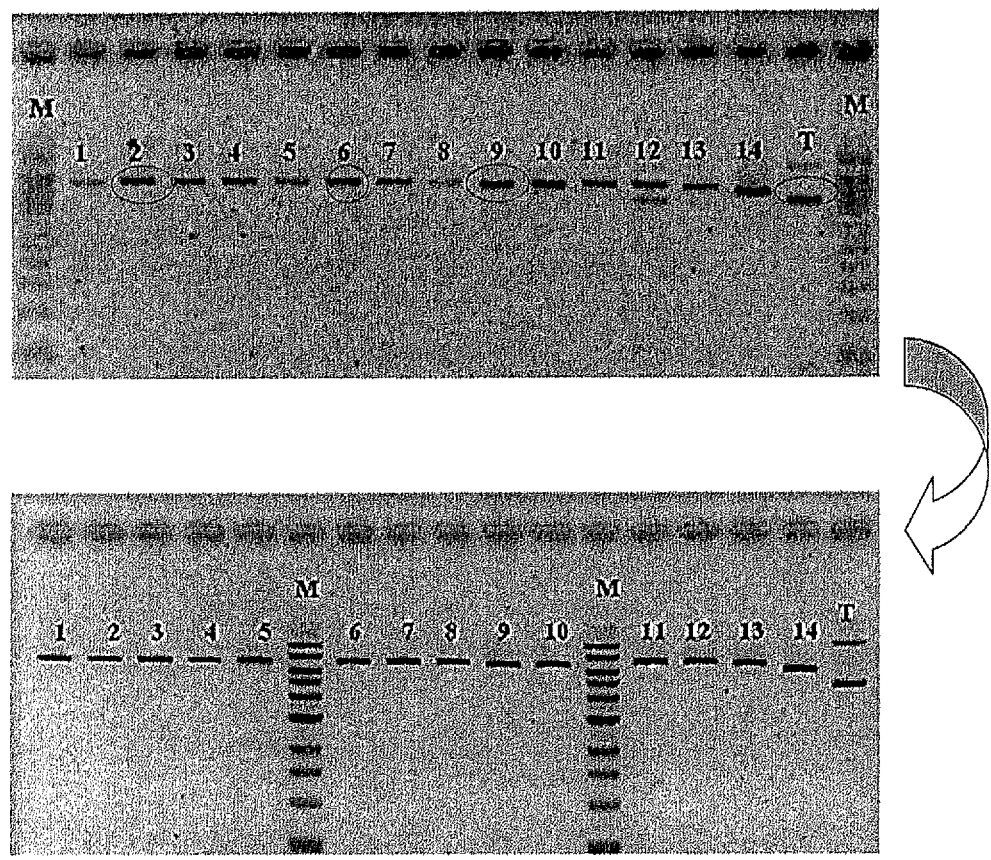
FIG. 5: Spectrometric assays of aliquots and adjustment of concentrations of DNAs after enzymatic digestion. The double arrow indicates that the concentrations have been re-adjusted.

In order to verify the DNA concentrations, we linearized the plasmids by enzymatic digestion using the Hind III/Not I pair, then we analyzed them using gel electrophoresis (see FIG. 5, upper profile). It became clear that the intensity of the bands obtained was still variable. Thus, we readjusted the concentrations as a function of the spectrometric assays and the intensity of the bands obtained after digestion (see FIG. 5, lower profile). Obtaining bands with equal intensities, in addition to ensuring the precision of the concentrations of our DNAs before being transfected into the cells, means that the electrophoreses are easier to read following enzymatic digestions when checking the identity of the plasmids.

D. Checking the Identity of the DNAs After Enzymatic Digestion.

1) General Principle:

In order to assure ourselves of the identity of the 14 DNAs prepared, they are all checked by digestion using the restriction enzymes Hind III and Not I, Xba I, Aat II, Pac I as well as Sfo I, which have to result in different combinations of profiles on gels for each of the DNAs. The agarose gel migration (0.8%) of the digestion products enables the DNAs to be differentiated as a function of the number and size of the bands obtained, as indicated in Table 1 (NB: bands with a size below a hundred base pairs are not visible on our gel electrophoresis images).

Digestion of the constructs studied means that we can assure ourselves of the identity of each plasmid. Differentiation of the large types of CD8-CD™ constructs is carried out by analyzing the number and size of the bands obtained after digestion with the enzymes Hind III/Not I and Xba I. Differentiation between the various cysteine residue mutants was carried out after digestion with the enzymes Aat II, Pac I and Sfo I. The number of bands thus obtained is greater than with the digestions by Hind III/Not I and Xba I, and the differentiation is principally made on the basis of the presence or otherwise of specific bands (in bold).

TABLE 1

| | | Theoretical number of bands obtained after digestions | | | | |
|---|---|---|---|---|---|---|
| N° | Plasmid | Hind III/Not I | Xba I | Aat II | Sfo I | Pac I |
| 1 | pX2 wt TM | 2 | 3 | 8 (i) | 4 | 0 |
| 2 | pX2 MCA | 2 | 3 | 8 (i) | 4 | 1 |

TABLE 1-continued

| N° | Plasmid | Hind III/Not I | Xba I | Aat II | Sfo I | Pac I |
|---|---|---|---|---|---|---|
| 3 | pX2 M2 | 2 | 3 | 9 ⎫ (j) | 4 ⎫ (k) | 1 |
| 4 | pX2 M14 | 2 | 3 | 9 ⎭ | 4 | 0 |
| 5 | pX2 M15 | 2 ⎫ (a) | 3 ⎫ (e) | 8 | 5 ⎫ | 0 |
| 6 | pX2 M16 | 2 | 3 | 8 | 5 | 1 |
| 7 | pX2 M17 | 2 | 3 | 9 | 5 ⎬ (l) | 1 |
| 8 | pX2 M18 | 2 ⎭ | 3 ⎭ | 9 | 5 ⎭ | 0 |
| 9 | pX3 wt TM | 2 ⎫ (b) | 2 ⎫ (f) | 8 | 4 | 0 |
| 10 | pX3 M15 | 2 ⎭ | 2 ⎭ | 9 | 4 | 1 |
| 11 | pX4 wt TM | 1 ⎫ (c) | 2 ⎫ (g) | 8 | 4 | 0 |
| 12 | pX4 M15 | 1 ⎭ | 2 ⎭ | 8 | 5 | 0 |
| 13 | pX4 Stp | 1 | (d) 2 | (h) 8 | 4 | 0 |

Expected sizes of the bands (in bp):
a): 7206/49
(b): 6868/311
(c): 7162
(d): 6937
(e): 6822/367/66
(f): 6812/367
(g): 6552/610
(h): 6552/385
(i): 4285/1055/801/498/294/186/83/53
(j): 3423/1055/862/801/294/186/83/53
(k): 4276/2538/310/131
(l): 4276/1839/699/310/131

2) Example:

In order to differentiate the pX2 mutants AAC and pX2 CCA, the gels we obtained are shown in FIG. 6A.
Interpretation:
Digestion by Hind III/Not I: a single band is obtained, at approximately 7206 bp, corresponding to the presence of constructs X2 or X4 in each of the two samples.
Digestion by XbaI: two bands are obtained at approximately 6822 (or 6812) and 367 bp, corresponding to the presence of constructs X2 or X3 in each of the two samples.

By cross-checking these two results, we are able to confirm that we are indeed in the presence of two constructs of type X2.

We then seek to discriminate the mutants X2 between themselves (see FIG. 6B):
Interpretation:
Digestion with AatII:
Sample 4: a first specific band is obtained of close to 3423 bp (red), corresponding to the presence of one of the following X2 plasmids: pX2 CAC, pX2 AAC, pX2 CAA or pX2 AAA.
Sample 5: a first specific band is obtained of close to 4285 bp (blue), corresponding to the presence of one of the following X2 plasmids: pX2 CCC, pX2 ACC, pX2 CCA or pX2 ACA.
Digestion with Sfo I:
Sample 4: a specific band is obtained of close to 2538 bp (red), corresponding to the presence of one of the following X2 plasmids: pX2 CCC, pX2 ACC, pX2 CAC, pX2 AAC. By cross-checking this result with that for the digestion with Aat II, we are then able to conclude that we were in the presence of one of the following plasmids: pX2 AAC or pX2 CAC.
Sample 5: 2 specific bands are obtained of close to 1839 bp (black) and 699 bp (green), corresponding to the presence of one of the following X2 plasmids: pX2 CCA, pX2 ACA, pX2 CAA, pX2 AAA. By cross-checking this result with that for the digestion with Aat II, we are then able to conclude that we are in the presence of one of the following plasmids: pX2 CCA or pX2 ACA.

Digestion with Pac I:
For each sample, we obtain 1 band with a low intensity, corresponding to non super-coiled DNAp as well as a high intensity band corresponding to our super-coiled DNAp (blue), demonstrating the absence of digestion by Pac I for these samples.

Samples 4 and 5 respectively correspond to pX2 mutants AAC and pX2 CCA.

This process was applied to all of the plasmids for the purposes of identification.

3) Conclusion:
During this step for preparation of DNAs, we obtained several milligrams of each of the 14 purified plasmids and their identities have all been confirmed after checking by enzymatic digestion and gel analyses. In addition, all of the DNAs had been adjusted to the same concentration.

II. Analysis of the Expression of Chimeras:

In order to evaluate expression of the DNAs, the same quantity of each of the plasmids was transfected into HEK293 cells. The proteins thus expressed are analyzed by gel migration followed by transfer onto a PVDF membrane. The membranes are then revealed using an anti-CD™ rabbit serum and secondary anti-rabbit antibody tagged with peroxidase.

Figure 7:
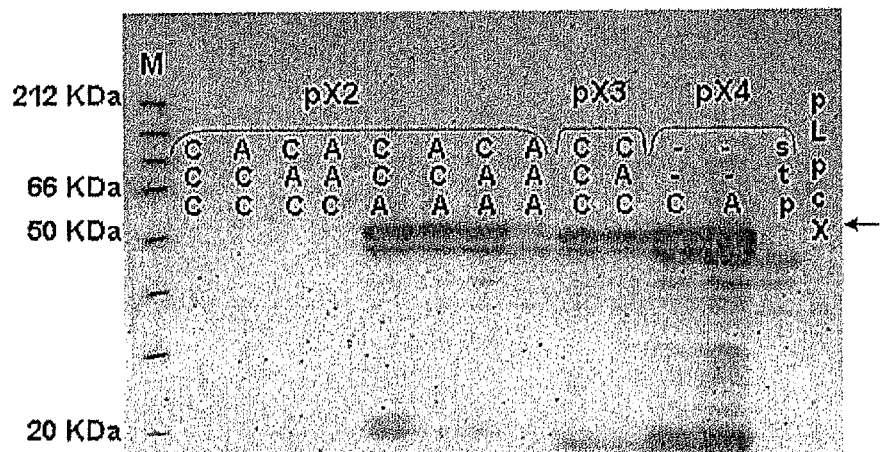
FIG. 7: Western Blot analysis of the expression of various CD8-CD™ chimeras. The chimera CD8-CD™ is indicated by an arrow.

A. Analysis of the Presence of CD8-CD™ within Cellular Lysates:

1) Analyses of Unrefined Lysates:
After 48 h of transfection, the cells are lysed and the extracts obtained are assayed using the Bradford technique. We analyzed 200 µg of unrefined proteins derived from these lysates by gel migration and Western Blot, revealed with an anti-CD™ antibody (see FIG. 7).

Various specific signals are then observable, depending on the samples:

A double band at 50 kDa (blue), corresponding to the presence of CD8-CD™. The two bands corresponded to two levels of glycosylation of CD8.

A signal at approximately 20 kDa (red) of indeterminate origin.

The samples pX2 CCC, pX2 ACC, pX2 CAC, pX2 AAC, pX4 stp and pLPCX do not have these bands.

2) Analysis of Lysates after Immunoprecipitation by Anti-CD8 Antibodies:

In order to reduce the detection threshold for CD8-CD™ in the cell lysates, we used a large quantity of extract and concentrated the chimeras by immunoprecipitation with specific monoclonal antibodies of a conformational epitope of the ectodomain of CD8.

Figure 8:
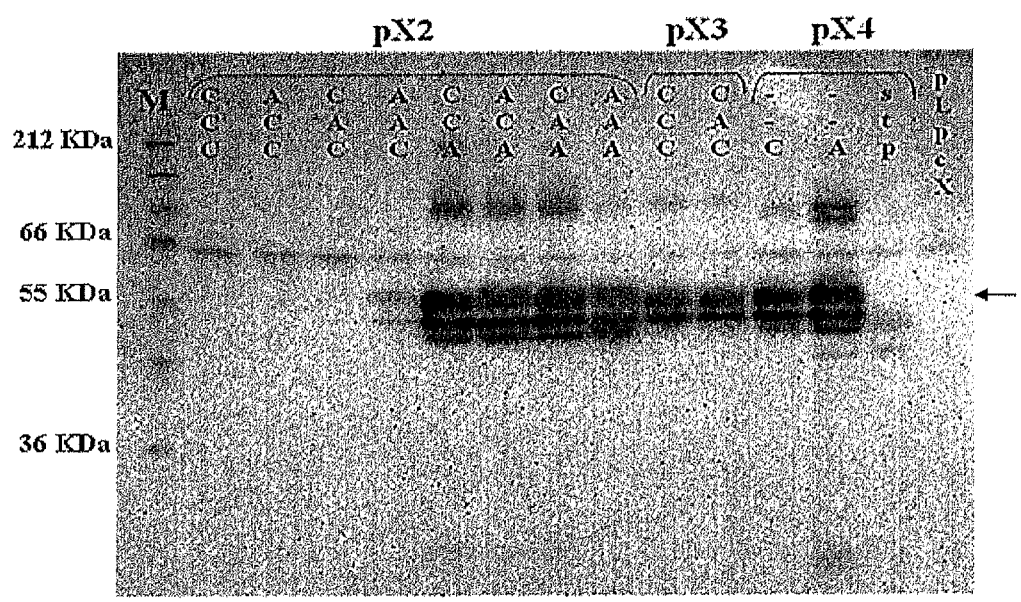
FIG. 8: Western Blot analysis of the expression of various CD8-CD™ chimeras after immunoprecipitation. The chimera CD8-CD™ is indicated by an arrow.

After 48 h of transfection, the cells are lysed and the extracts obtained are assayed using the Bradford technique. After normalization of the protein concentrations, the extracts are immunoprecipitated in the presence of anti CD8 antibodies and protein A sepharose. The products obtained are analyzed by gel migration and Western Blot and revealed with an anti-CD™ antibody (see FIG. 8). Various signals can then be observed, depending on the samples:

A double band at 55 kDa (blue), corresponding to the presence of CD8-CD™.

An unidentified signal, found for each sample, at approximately 66 kDa.

One or more signals with a molecular weight of more than 66 KDa, probably corresponding to the presence of multimerized CD8-CD™ proteins.

Here, the sample pX2 AAC exhibits a detectable signal at 50 KDa, in contrast to the analysis carried out without immunoprecipitation. In contrast, no signal could be detected for the samples pX2 CCC, pX2 ACC, pX2 CAC, pX4 stp and pLPCX.

3) Summary of the Analysis of the Expression of CD8-CD™ within Cellular Lysates:

By correlating the data obtained by Western Blot for cell lysates with the characteristics of each chimera (integrity of tmD BLV, presence of third cysteine residue and number of cysteine residues), we are able to draw up Table 2 below.

It appears that, in addition to CD™ of BLV, two factors may have an influence on the presence of CD8-CD™ chimeras. These factors are: the presence or otherwise of tmD BLV, and the presence or otherwise of the third cysteine residue (Cys 213).

B. Analysis of the Association of CD8-CD™ with Exosomes:

The various DNAs used only differed in a few nucleotides. It is thus probable that the quantities of CD8-CD™ that were synthesized are equivalent. However, it became clear, during the analysis of the expression of CD™ in cell lysates, that certain chimeras are not detectable 48 h after transfection. This absence of signal would reflect the disappearance of certain of our chimeric proteins. This disappearance could be due either to a rapid degradation of these chimeras or to their secretion in the form of exosomes.

We thus investigated to detect the presence of CD8-CD™ within exosomes.

TABLE 2

| Construct | tmD BLV | No of cysteines | Signal CD ™ BLV |
|---|---|---|---|
| pX2 CCC | Complete | 3 | Zero |
| pX2 ACC | Complete | 2 | Zero |
| pX2 CAC | Complete | 2 | Zero |

TABLE 2-continued

| Construct | tmD BLV | No of cysteines | Signal CD ™ BLV |
|---|---|---|---|
| pX2 AAC | Complete | 1 | + |
| pX2 CCA | Complete | 2 | ++++ |
| pX2 ACA | Complete | 1 | ++++ |
| pX2 CAA | Complete | 1 | ++++ |
| pX2 AAA | Complete | 0 | ++ |
| pX3 CCC | −15 aa | 3 | +++ |
| pX3 CAC | −15 aa | 2 | +++ |
| pX4--C | Absent | 1 | ++++ |
| pX4--A | Absent | 0 | +++++ |
| pX4 stp | Absent | 0 | Zero |
| pLpcX | Absent | 0 | Zero |

Figure 9:
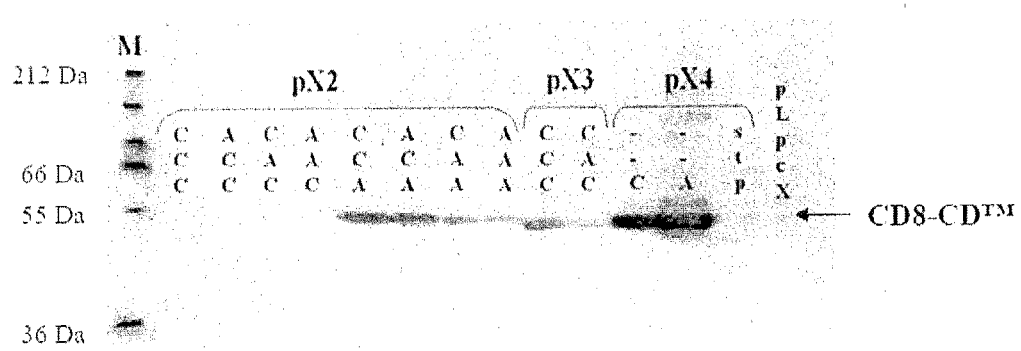
FIG. 9: Western Blot analysis of the expression of CD8-CD™ in exosomes isolated by ultracentrifuging. The signal at 55 kDa corresponds to the presence of CD8-CD™.

1) CD8-CD™ Content of Vesicles Isolated by Centrifuging:

After 48 h of transfection, the culture media are recovered and centrifuged to isolate the exosomes. The pellets obtained are then analyzed by gel migration and Western Blot and revealed with an anti-CD™ antibody (see FIG. 9).

Depending on the samples, it is possible to observe a signal at 55 kDa corresponding to the presence of CD8-CD™. This signal is not detectable for the samples pX2 CCC, pX2 ACC, pX2 CAC, pX2 AAC, pX4 stp and pLPCX.

Figure 10:
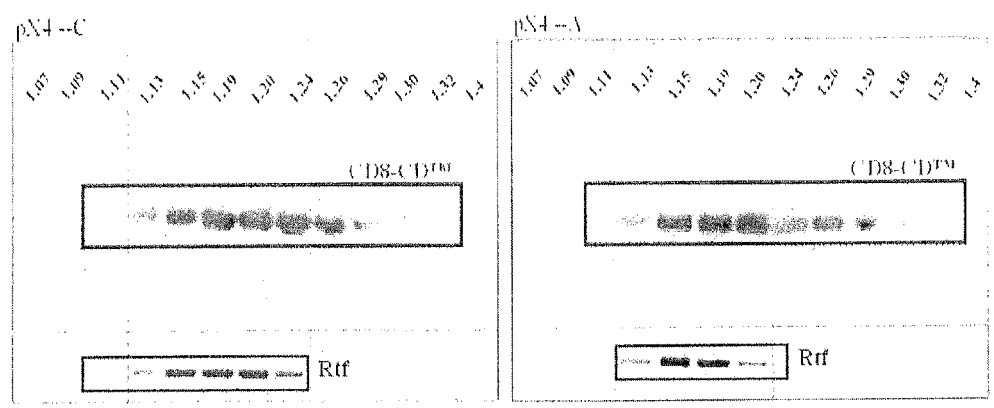
FIG. 10: Western Blot analysis of the CD8-CD™ content of vesicles isolated after sucrose density gradient sedimentation, for the mutants pX4-C and pX4-A.

2) CD8-CD™ Content after Sedimentation of Vesicles on Sucrose Density Gradient:

In order to assure ourselves that the signal obtained after ultracentrifuging of the culture media is indeed due to the presence of chimeras in the exosomes and not due to the presence of cellular debris containing CD8-CD™, we analyzed the exosome pellets obtained using the method described above by sedimentation on a sucrose density gradient. The exosomes float at a density of 1.13 to 1.20 g/mL as a function of the cells used and of the composition of the vesicles. After sedimentation by ultracentrifuging, the gradient is removed in 700 µL fractions. The proteins are precipitated using TCA and analyzed by gel migration, then Western Blot and revealed with an anti CD™ antibody and an anti-transferrin receptor antibody (RTf) which could detect the presence of cellular vesicles (endosomes or exosomes). This analysis was carried out for the mutants pX4-C and pX4-A (see FIG. 10).

In pX4-C and pX4-A, a signal is detected corresponding to CD8-CD™ in the fractions with a density of 1.13 to 1.25 g/mL. For these same densities, we were also able to detect a signal corresponding to RTf. These results reveal the presence of CD8-CD™ in the fractions containing the exosomes.

3) Summary of the Analysis of the Association of Exosomes with CD8-CD™:

The association of CD8-CD™ with the exosomes was detected for all of the mutants containing CD™ except for the pX2s with Cys 213. The mutants pX4-C and pX4-A appear to have been very effectively targeted into the exosomes. The pX3 mutants and pX2 without Cys 213 are also found in the exosomes, but in smaller proportions than for the mutants pX4-C and pX4-A.

It thus appears that as well as the presence of viral CD™, two factors may have an influence on targeting CD8-CD™ chimeras in exosomes.

These factors are:

The presence or otherwise of a transmembrane domain of BLV.

The presence or otherwise of Cys 3.

C. Influence of Inhibition of Vesicular Transport on the Expression of CD8-CD™ Chimeras:

Since the absence of detection of the chimeras pX2 CCC, pX2 ACC, pX2 CAC and pX2 AAC was not due to increased exosomal secretion, we wanted to know whether it could be due to degradation by sorting the MVB proteins to the lysosomes.

Figure 11:
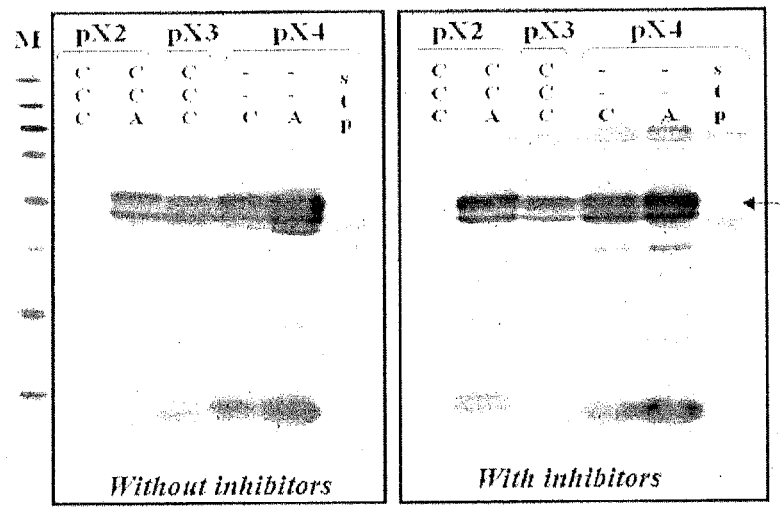
FIG. 11: Western Blot analysis of the expression of CD8-CD™ after cell lysis, showing the presence or absence of vesicular transport inhibitors. The chimera CD8-CD™ is indicated by an arrow.
Figure 12:
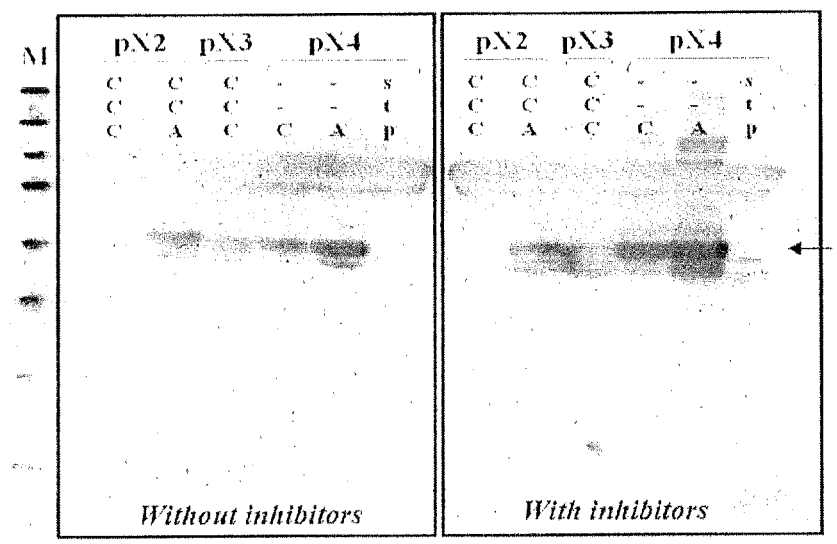
FIG. 12: Western Blot analysis of the expression of CD8-CD™ within the exosomes, depending on the presence or absence of vesicular transport inhibitors. The chimera CD8-CD™ is indicated by an arrow.
Figure 13:
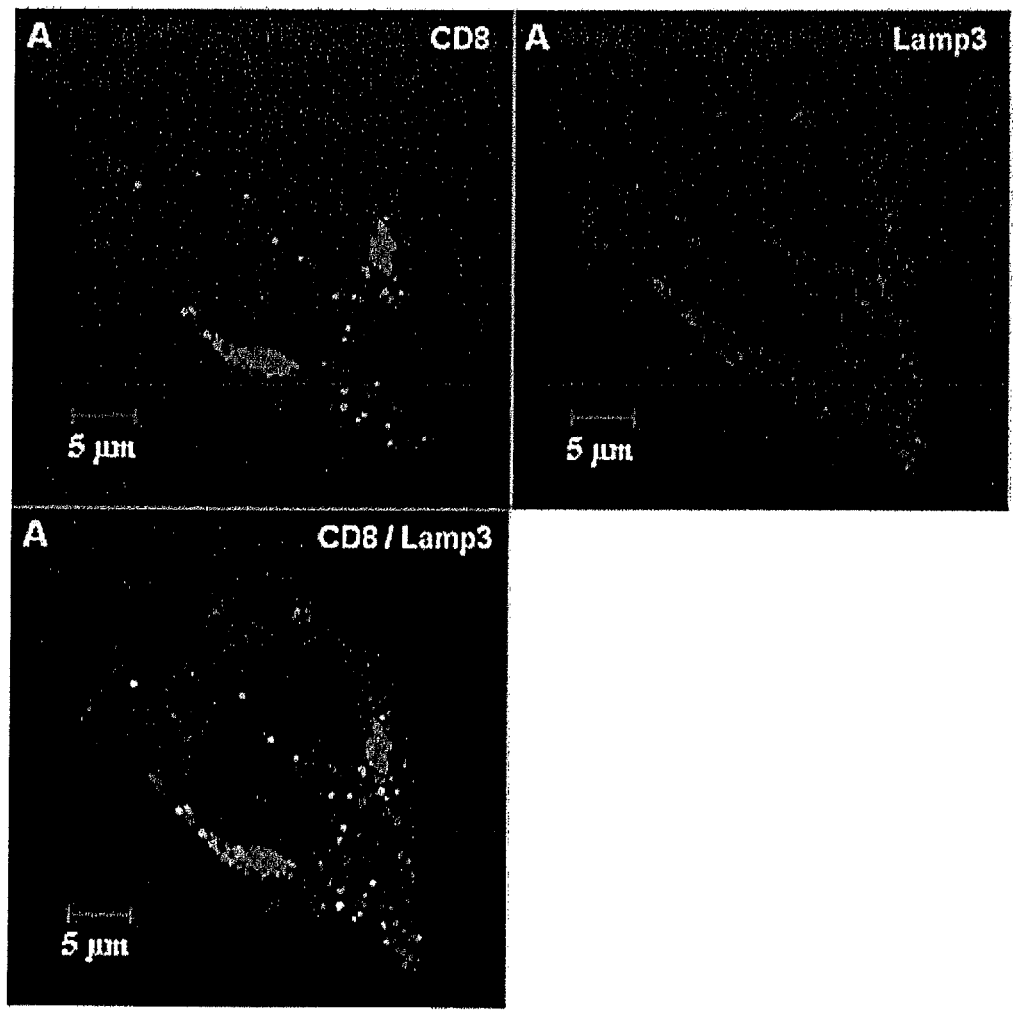
FIG. 13: Analysis, by confocal immunofluorescence imaging, of general phenotypes—Phenotype A—HEK293 cells transfected with pX2 CAC. This phenotype is found in pX2 mutants conserving Cys 3: pX2 CCC, pX2 ACC, pX2 CAC and pX2 AAC. (see Results section, "localization by immunofluorescence).
Figure 14:
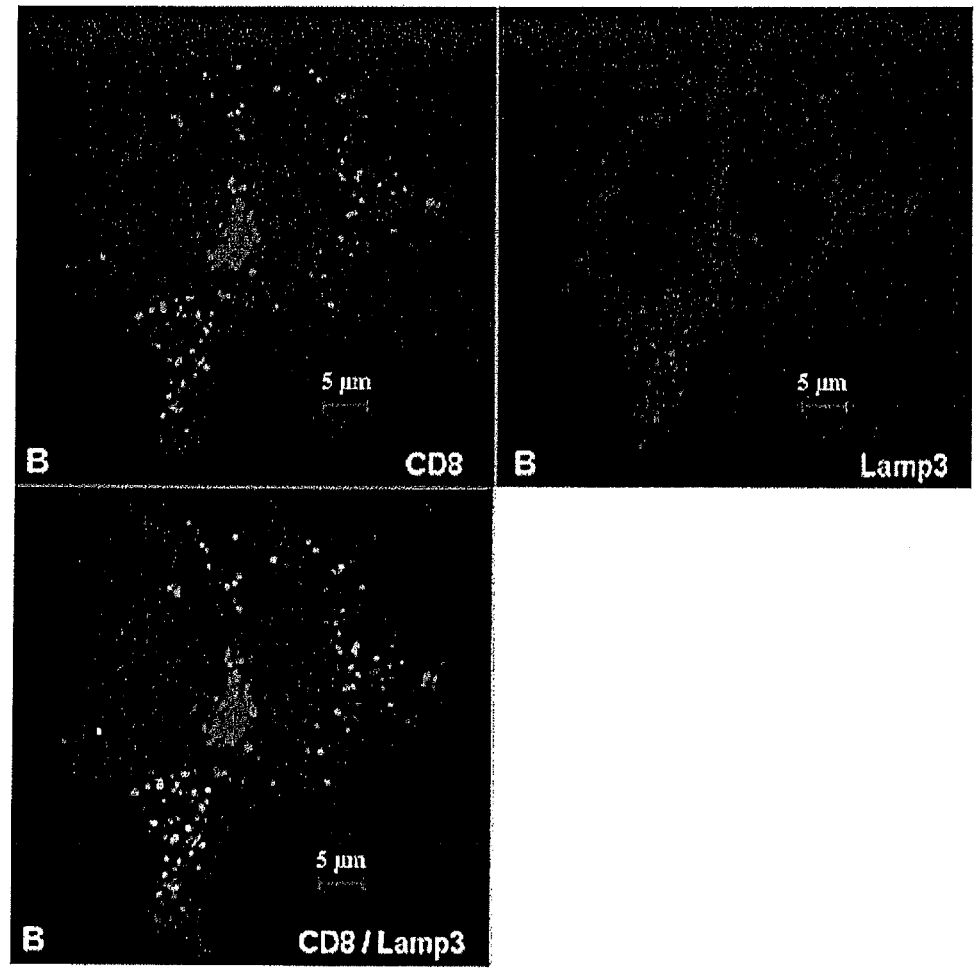
FIG. 14: Analysis, by confocal immunofluorescence imaging, of general phenotypes—Phenotype B—Cells transfected with pX2 CAA. This phenotype is found in pX2 mutants not conserving Cys 3: pX2 CCA, pX2 ACA, pX2 CAA and pX2 AAA. (See Results section, "localization by immunofluorescence).
Figure 15:
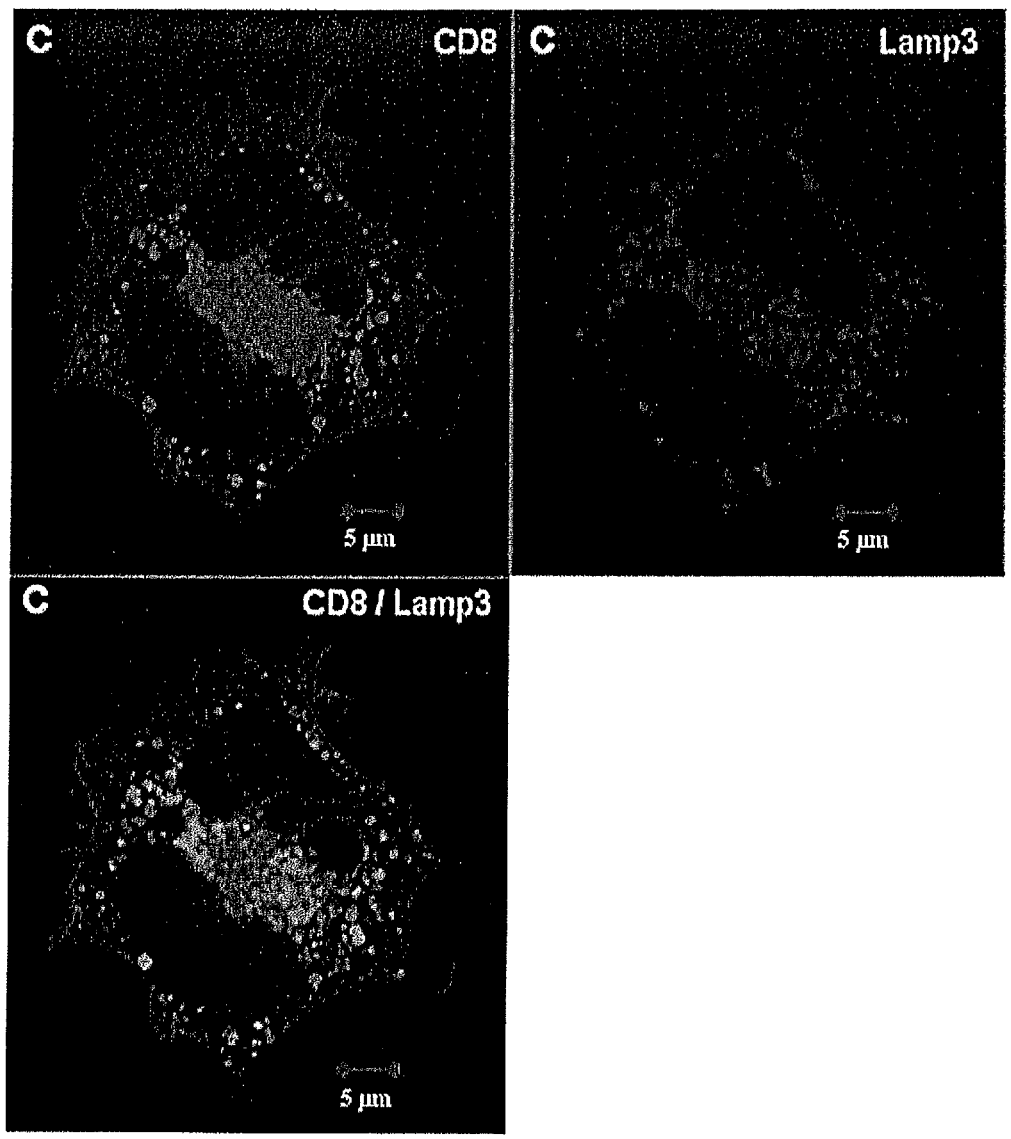
FIG. 15: Analysis, by confocal immunofluorescence imaging, of general phenotypes—Phenotype C—Cells transfected with pX3 CCC. This phenotype is found in the two pX3 mutants studied: pX3 CCC and pX3 ACC. (See Results section, "localization by immunofluorescence)
Figure 16:
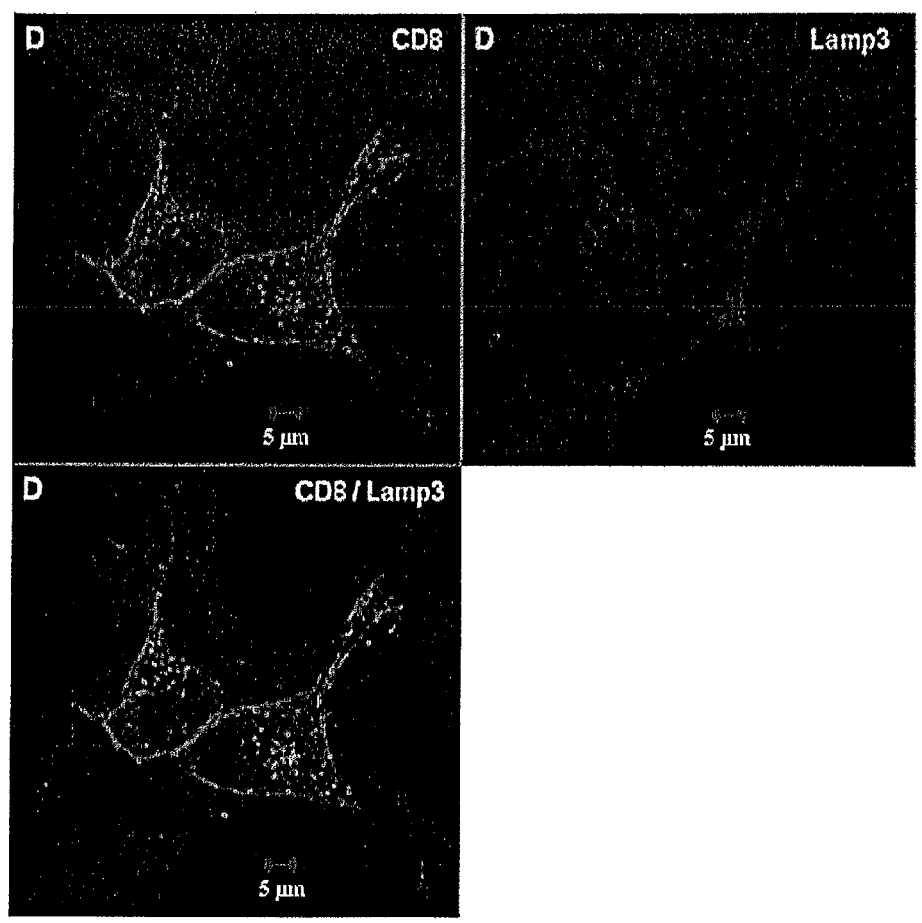
FIG. 16: Analysis, by confocal immunofluorescence imaging, of general phenotypes—Phenotype D—Cells transfected with pX4-C. This phenotype is found in the two pX4 mutants studied: pX4-C and pX4-A. (See Results section, "localization by immunofluorescence)
Figure 17:
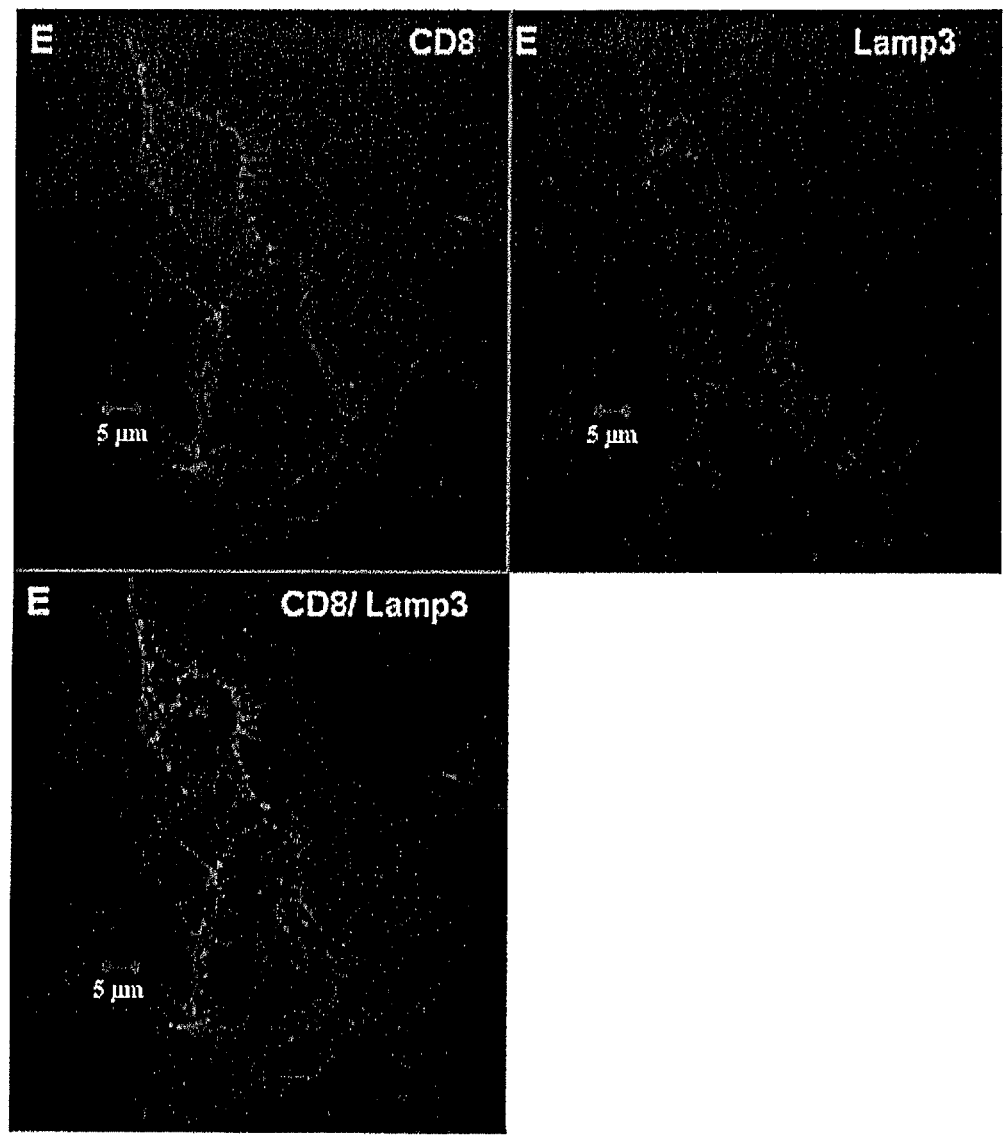
FIG. 17: Analysis, by confocal immunofluorescence imaging, of general phenotypes—Phenotype E—Cells transfected with pX4 stp. This phenotype is found only in pX4 stp. (See Results section, "localization by immunofluorescence)

To this end, we used vesicular transport inhibitors, namely bafilomycin and Ly294002. These inhibitors can block the lysosomal degradation pathway, thereby promoting the secretion of proteins by the exosomes. The inhibitors are added to the culture media 32 h after transfection: 16 h later, the cells are lysed and the culture media are recovered then centrifuged to isolate the exosomes. The samples obtained are then analyzed by gel migration and Western Blot and revealed with an anti-CD™ antibody. We thus analyzed the expression of the chimeras pX2 CCC, pX2 CCA, pX3 CCC, pX4-C, pX4-A and pX4 stp (see FIGS. 11 and 12).

It appears that, for these mutants, the Western Blot profile for the proteins obtained in the presence of inhibitors is the same as that during analysis without an inhibitor, irrespective of whether it was for the cellular lysates or for the exosomes.

The absence of the chimeras pX2 CCC, pX2 ACC, pX2 CAC and pX2 AAC is thus apparently due neither to accelerated exosomal exit nor to degradation in the lysosomes. It is probable that it is the consequence of very early degradation in the folding control system within the endoplasmic reticulum (ER) and the TGN.

III. Localization by Immunofluorescence:

In order to assess the membrane targeting of CD8-CD™ and its localization in cellular compartments, we carried out confocal immunofluorescence microscopic observations. 48 h after transfection, the cells were fixed then tagged using various antibodies.

A. Selection of Antibodies:

Initially, each type of tag (see Materials and Methods section) is tested with varying dilutions of antibodies on fixed cells expressing pX4-C or pLPCX. After observation with a conventional immunofluorescence microscope (ZEISS Axiovert 200 M), we tested the various antibodies at our disposal (see Materials and Methods section) and determined their efficacy as well as their optimal dilutions. It was observed that several anti-intra-cellular compartment antibodies produced a zero or non-specific signal.

For the confocal imagery observation, we were therefore only able to use two types of tags:

CD8-CD™ tagging:
rat IgG (53/6.7) anti-mouse CD8 FITC (Pharmingen, dilution 1/50)

Lamp3 tagging:
mouse anti-human CD63 (Lamp3) IgG (Zymed, dilution 1/50)+anti-mouse IgG Cy3 (Sigma, dilution 1/500)

B. Observations of the Distribution of CD8-CD™:

After fixing and tagging of the cells using our various antibodies, we observed the distribution of tagging from CD8-CD™ as well as its co-localization with Lamp3 with the aid of a confocal microscope (ZEISS LSM 510).

Cells expressing pLPCX (negative control) did not have a signal FITC. This control thus enabled us to assure ourselves that the FITC fluorescence observed for the other mutants was indeed derived from the presence of CD8-CD™.

Surprisingly, despite an absence of detection by Western Blot, the constructs pX2 comprising Cys 3 were visible, albeit only weakly, by immunofluorescence.

Analysis of General Phenotypes:

The HEK293 cells were transfected for a period of 48 h then fixed. The observation is carried out using a ZEISS LSM 510 confocal microscope (×63 immersion objective).

CD8: FITC (green) tag revealing the presence of chimeras containing CD8.

Lamp3: Cy3 (red) tag revealing the presence of the Lamp3 protein characteristic of late endosomes.

CD8-CD™/Lamp3: Superposition of FITC and Cy3 images. The yellow shade obtained demonstrates the co-localization of CD8-CD™ with Lamp3.

Using the observations, we were able to distinguish 5 general phenotypes (see FIGS. 13 to 17) based on appearance (vesicular, membrane or perinuclear) and the intensity of the FITC tag. The co-localization of the FITC tag with a vesicular appearance with Lamp3 does not need to be considered when determining these phenotypes as it is present in all of the mutants. In addition, this co-localization is always partial.

Analysis of Perinuclear Zones Having a Strong FITC Signal:

For all of the samples except for pX4 stp, we found that there was an approximately constant large homogeneous CD8 perinuclear signal at the periphery of the nucleus. The intensity parameters required in order to view the major portion of the FITC fluorescence present in the cells caused saturation of this zone. A signal which is saturated in this way cannot be exploited as much, and so we captured lower intensity parameters by concentrating on analysis of these zones, in particular to determine the pertinence of the co-localizations they exhibited with Lamp3.

CD8-CD™/Lamp3 [a]: Co-localization of CD8-CD™ (green) with Lamp3 (red). The intensity parameters for acquisition, while weak, caused saturation of the perinuclear signal and the appearance of yellow shades at this point, demonstrating partial co-localization between these two tags. Because of the signal saturation, it is impossible to state whether the co-localization was real or artifactual.

CD8-CD™ [d]: FITC signal from CD8-CD™. The intensity parameters were substantially reduced in order to eliminate any signal saturation phenomena. The signal FITC appeared diffuse, homogeneous and not spot-like.

CD8-CD™/Lamp3 [d]: Co-localization of CD8-CD™ (green) with Lamp3 (red). The intensity parameters were substantially reduced in order to eliminate any signal saturation phenomena. This resulted in an absence of yellow shades, demonstrating the absence of co-localization between FITC and Lamp3.

Figure 18:
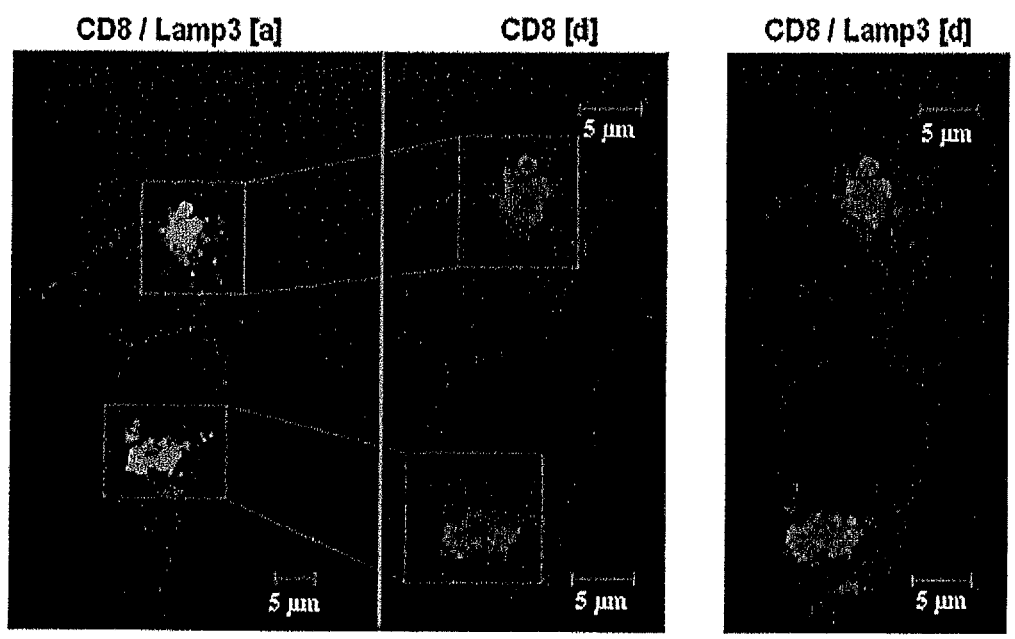
FIG. 18: Analysis, by confocal immunofluorescence imaging, of perinuclear zones exhibits a strong FITC signal. Cells transfected with pX3 CCC.

According to these acquisitions, the tag derived from Lamp3 in fact appears to be located inside this perinuclear zone but in all cases it was never co-localized with the FITC tag (see FIG. 18).

In addition, the tag from CD8-CD™ of these perinuclear zones appears to be diffuse, homogeneous and not spot-like, and appears to provide evidence for the presence of CD8-CD™ within a cellular structure. The localization and the appearance of this tag, as well as the absence of actual co-localization with Lamp3, suggest the presence of CD8-CD™ in the Golgi apparatus.

This phenotype is observed, to a greater or lesser intensity, in all of the mutants apart from pX4 stp. In mutants pX4-C and pX4-A, this phenotype was only visible in a minority of cells, in contrast to the pX2 mutants and pX3 in which it is constantly present.

TABLE 3

| Phenotype | Mutants | FITC intensity | Localisation of FITC tagging | | |
|---|---|---|---|---|---|
| | | | Vesicular | Membrane | TGN |
| A | pX2 CCC | + | +++ | − | ++ |
| | pX2 ACC | + | +++ | − | ++ |
| | pX2 CAC | + | +++ | − | ++ |
| | pX2 AAC | + | +++ | − | ++ |
| B | pX2 CCA | +++ | ++++ | − | ++ |
| | pX2 ACA | +++ | ++++ | − | ++ |
| | pX2 CAA | +++ | ++++ | − | ++ |
| | pX2 AAA | +++ | ++++ | − | ++ |
| C | pX3 CCC | ++++++ | + | +++ | +++++ |
| | pX3 CAC | ++++++ | + | +++ | +++++ |
| D | pX4--C | ++++++ | ++ | ++++ | + |
| | pX4--A | ++++++ | ++ | ++++ | + |
| E | pX4 stp | ++++ | + | +++ | − |

Thus, the specific observation of perinuclear zones strongly tagged with FITC enabled us to demonstrate the probable presence of CD8-CD™ within the TGN.

Using the data obtained, we drew up the above summary table (see Table 3).

These observations confirm that in addition to viral CD™, two factors have an influence on the stability and targeting of our chimeras.

These factors are:
The presence or otherwise of tmD BLV.
The presence or otherwise of N-terminal residues of CD™ of BLV.
The presence or otherwise of Cys 3.

Conclusion:

During our analyses, it was shown that the chimera pX4 stp, composed only of the ectodomain and tmD of CD8, accumulates in HEK293 cells and are effectively targeted to the plasma membrane.

In the same manner, the chimeras pX4-C and pX4-A accumulate and are found in the plasma membrane, but in greater proportions than for pX4 stp. These chimeras are very effectively secreted within exosomes.

For their part, pX3 chimeras are mostly present in the Golgi apparatus, in contrast to pX4 chimeras. Targeting them within the plasma membrane and in the exosomes appears to be less effective than in px4 chimeras but remains important.

The pX2 chimeras appear to be less stable and are found in the TGN but not in the plasma membrane. pX2 constructs comprising Cys 3 have very low stability in cells and are not detected in the exosomes. Substitution of the terminal Cys into this type of construct appears to contribute to a gain in stability of the chimeric proteins. In effect, the pX2 minus Cys 3 constructs are detectable in cells and in exosomes.

All of the chimeras studied have, in immunofluorescence, a vesicular tag that is partially co-localized with a tag for the late endosomes.

This study has demonstrated the importance of the presence or absence of Cys 3 in the stability and in the targeting of CD8-CD™ chimeras. It appears that an absence of this cysteine residue promotes the stability and membrane targeting of the chimeras studied as well as their presence in the exosomes. These phenomena could be independent of hyperpalmitylation associated with the absence of Cys 3. In fact, the construct pX2 AAC, which is not palmitylated, is more stable than the three pX2 mutants with Cys 3 as well as Cys 1 and/or Cys 2, which are palmitylable. However, a different implication for palmitylation in the stability and targeting of our chimeras cannot be excluded.

This study has enabled us to discover the fundamental importance of BLV tmD. The deletion of all or a portion of BLV tmD appears to substantially increase the stability of the chimeras as well as their targeting in the plasma membrane. Thus, astonishingly, the presence of BLV tmD promotes the early degradation of the chimeras. This degradation could occur at the level of the folding control system within the cell compartments, namely the ER and the TGN, since the lysosomal degradation pathway does not seem to be involved. The absence of vesicular transport inhibitor effects on the stability and exosomal targeting of the CD8-CD™ chimeras as well as their highly partial co-localization with late endosomes, even for the least stable chimeras, supports this hypothesis.

The principal attraction of our work lies in the discovery of potentially effective tools for the development of a mode of vaccination based on the "exosome display" concept. In effect, the chimeras pX4-C and especially pX4-A appear to have a molecular "motor" that can enable highly effective targeting of the peptide antigen (in this case CD8) to the exosomes. This "motor" thus appears to be located in the cytoplasmic domain of the TM protein of BLV.

Example 2

Figure 19:
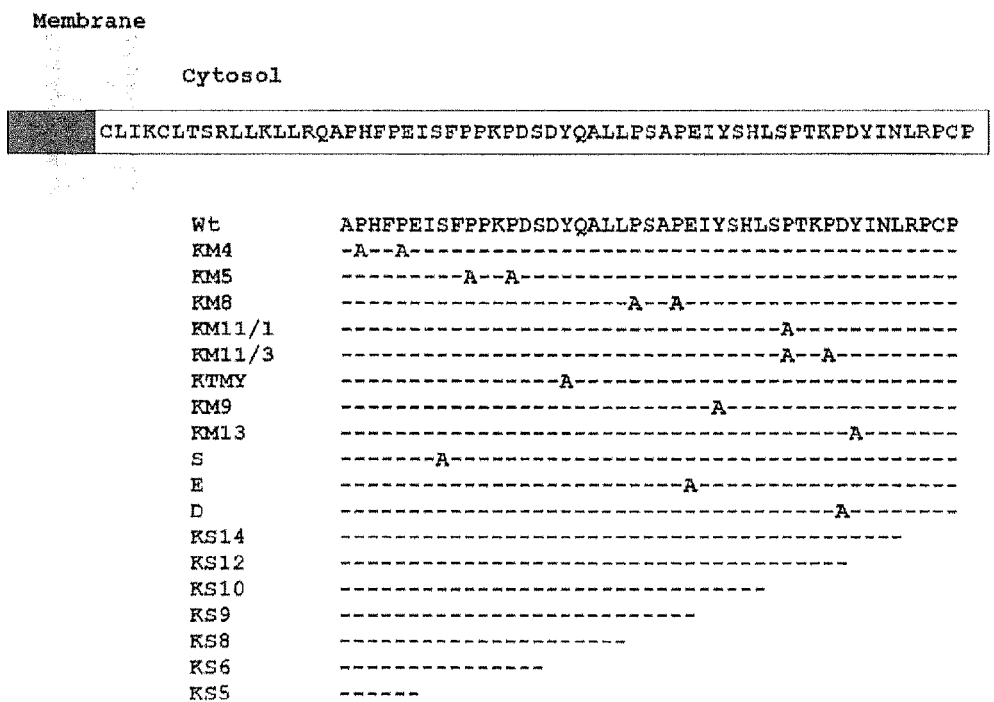
FIG. 19: Representation of panel of CD™ mutants.

Identification of Amino Acids Involved in the Exosomal Targeting of the CD™ Peptide In order to determine the exact nature of the "motor" located in the cytoplasmic domain of the TM protein of BLV before carrying out the first immunization tests, we studied the effect of 18 types of mutations in the cytoplasmic domain of the TM protein of BLV (see FIG. 19):

deletion of the 13 N-terminal residues and substitution of the 2 proline residues of the first motif PxxP (SEQ ID NO: 13 and SEQ ID NO: 14; mutation KM4);

deletion of the 13 N-terminal residues and substitution of the 2 proline residues of the second motif PxxP (SEQ ID NO: 15 and SEQ ID NO: 16; mutation KM5);

deletion of the 13 N-terminal residues and substitution of the 2 proline residues of the third motif PxxP (SEQ ID NO: 17 and SEQ ID NO: 18; mutation KM8);

deletion of the 13 N-terminal residues and substitution of the first proline residue of the fourth motif PxxP (SEQ ID NO: 19 and SEQ ID NO: 20; mutation KM11/1);

substitution of the 2 proline residues of the fourth motif PxxP (SEQ ID NO: 21 and SEQ ID NO: 22; mutation KM11/3);

deletion of the 13 N-terminal residues and substitution of the tyrosine residue of the first motif YxxL (SEQ ID NO: 23 and SEQ ID NO: 24; mutation KTMY);

deletion of the 13 N-terminal residues and substitution of the tyrosine residue of the second motif YxxL (SEQ ID NO: 25 and SEQ ID NO: 26; mutation KM9);

deletion of the 13 N-terminal residues and substitution of the tyrosine residue of the third motif YxxL (SEQ ID NO: 27 and SEQ ID NO: 28; mutation KM13);

deletion of the 13 N-terminal residues and substitution of the serine residue located before the first motif YxxL (SEQ ID NO: 29 and SEQ ID NO: 30; mutation S);

deletion of the 13 N-terminal residues and substitution of the glutamic acid residue located before the second motif YxxL (SEQ ID NO: 31 and SEQ ID NO: 32; mutation E);

deletion of the 13 N-terminal residues and substitution of the aspartic acid residue located before the third motif YxxL (SEQ ID NO: 33 and; SEQ ID NO: 34; mutation D);

sequence truncated to 6 residues—deletion of the 13 N-terminal residues and of the 39 C-terminal residues (SEQ ID NO: 35 and SEQ ID NO: 36; mutation KS5);

sequence truncated to 15 residues—deletion of the 13 N-terminal residues and of the 30 C-terminal residues (SEQ ID NO: 37 and SEQ ID NO: 38; mutation KS6);

sequence truncated to 21 residues—deletion of the 13 N-terminal residues and of the 24 C-terminal residues (SEQ ID NO: 39 and SEQ ID NO: 40; mutation KS8);

sequence truncated to 26 residues—deletion of the 13 N-terminal residues and of the 19 C-terminal residues (SEQ ID NO: 41 and SEQ ID NO: 42; mutation KS9);

sequence truncated to 31 residues—deletion of the 13 N-terminal residues and of the 14 C-terminal residues (SEQ ID NO: 43 and SEQ ID NO: 44; mutation KS10);

sequence truncated to 37 residues—deletion of the 13 N-terminal residues and of the 8 C-terminal residues (SEQ ID NO: 45 and SEQ ID NO: 46; mutation KS12);

sequence truncated to 41 residues—deletion of the 13 N-terminal residues and of the 4 C-terminal residues (SEQ ID NO: 47 and SEQ ID NO: 48; mutation KS14).

The substitution and deletion mutants were obtained by directed mutagenesis; the substituted residues were replaced by an alanine residue. Translation of the deletion mutants was halted by adding a stop codon (TGA, TAG or TAA codon).

The DNA sequences coding for the 18 mutants, as well as the wild type CD™ DNA sequence from which the 13 N-terminal residues had been deleted (SEQ D NO: 7; sequence hereinafter termed "wild type sequence") were sub-cloned downstream of a sequence coding for the ectodomain of murine CD8α. The 19 chimeric genes obtained were then cloned into a viral expression vector. The recombinant vectors thus obtained were transfected in eukaryotic cells (HEK cells) in order to analyze targeting to exosomes of the resulting chimeric proteins. 48 hours later, protein expression in the cells was examined by Western Blot. At the same time, the exosomes were purified by ultracentrifuging to enable sorting of the chimeric protein to be evaluated by FACS and Western Blot.

The results presented below demonstrate the necessity for two peptide motifs individually recognized in the literature for their interactions with proteins associated with the ESCRT machinery and the inter-membrane transfer machinery (in particular adaptins, including AP3). This is the first time that experimental evidence has been provided that these two peptide motifs play a vital synergistic role in exosomal targeting.

These results provide innovative and interesting information in terms of inter-cellular signaling using exosomes. They thus provide a well-defined tool for targeting proteins with exosomes. From an industrial viewpoint, they will facilitate the development of a new generation of vaccines and a unique tool for screening therapeutic molecules or antibody, for example.

1—Obtaining Molecular Constructs

A—Preparation of Inserts by PCR:

The three substitutional mutants S (Ser→Ala), D (Ac. Asp→Ala) and E (Ac.Glut→Ala) were obtained by directed mutagenesis by means of a double PCR using the following mutation primers:

```
S to A primer, forward:
5' CCCTAAACCCGATGCTGATTATCAGGCGTTGCTACCATCC 3'

S to A primer, reverse:
5' CGCGGATGGTAGCAACGCCTGATAATCAGCATCGGGTTTA 3'

D to A primer, forward:
5' CCACCAAGCCGGCATACATCAACCT 3'

D to A primer, reverse:
5' TCGAAGGTTGATGTATGCCGGCTTGGT 3'

E to A primer, forward:
5' GCTACCATCCGCGCCAGCGATCTAC 3'

E to A primer, reverse:
5' GTAGATCGCTGGCGCGGATGGTA 3'.
```

The PCRs were carried out using an Expand High Fidelity PCR system kit (Roche®) that has an enzyme mixture containing the thermostable Taq DNA polymerase and the thermostable Tgo DNA polymerase provided with a corrective activity (3'-5' exonuclease activity) that means that errors during polymerization can be limited and enables blunt end fragments to be obtained. Two mixtures of reagents were prepared at 4° C.:

A (25 µL): 10 ng of DNA to be amplified, 14 of dNTP 10 mM (200 µM final each), 1.5 µL of each of the two forward and reverse primers, 10 µM (300 nM final), sterile water (qsp 25 µL); and B (25 µL): 5 µL of "Expand High Fidelity" 10× buffer, with 15 mM $MgCl_2$ (1.5 mM final), 0.75 µL of "High Fidelity" enzyme mixture (2.6 U final), sterile water (qsp 25 µL).

A and B were mixed at 4° C. then the following amplification cycles were carried out:

denaturing of the double stranded DNA, 2 minutes at 94° C.;

4 cycles of denaturing (94° C., 10 seconds), hybridization (50° C., 15 seconds) and elongation (72° C., 20 seconds);

25 cycles: 10 seconds at 94° C., 15 seconds at 64° C. then 20 seconds at 72° C.;

final elongation for 7 minutes at 72° C.

The PCR product obtained was kept at 4° C.

The DNA sequences coding for the 18 mutants, as well as the wild type DNA sequences, were modified by PCR (directed mutagenesis) so that they were boxed in by particular restriction sites; the protocol indicated above was carried out using two primers having the restriction sites XbaI and NotI.

B—Cloning of PCR Products in TOPO-bluntII and Controls

Each of the 19 DNAs was ligated in a TOPO cloning vector (see FIG. 20) of the TOPO-blunt cloning kit (Invitrogen) for introduction into chemocompetent bacteria. The transformed clones were selected and all of the DNA sequences were checked by sequencing.

a) Ligation in the Plasmid and Transformation in Top10

Each of the various PCR products was integrated into a TOPO-BluntII plasmid that was already open and had blunt ends and carried the kanamycin resistance gene. The chemocompetent Top10 bacteria were transformed by these plasmids and cultured in a dish of LB/agar (100 µg/mL of kanamycin). TOPO-BluntII plasmid without insert acted as a negative control and another control (1 ng of plasmid PUC19) was used as a positive transformation control. After culture, only the bacteria transformed by a plasmid containing the insert or PUC19 (positive control) developed in the presence of the selection agent (antibiotic).

b) Screening of Good Clones and Sequencing:

From the cloning results, 2 to 10 colonies were amplified to carry out extraction of plasmid DNA. For each construct and each clone, we obtained a volume of plasmid DNA of 100 μL at approximately 150 ng/μL. The ratio of the absorption at 260 nm to the absorption at 280 nm for each purification provided a value in the range 1.8 to 2, which bore witness to the purity of the preparation (a value of less than 1.8 would have indicated protein contamination).

In order to demonstrate the presence of an insert in the plasmid, the plasmid DNAs were digested by the restriction enzyme EcoRI which boxed in the sequences of interest. These digestion products were viewed on 2% agarose gel where the presence of a fragment (approximately 300 bp) constituted proof of recombinant DNA.

Once good clones had been identified, 2 to 4 μg of plasmid DNA from each mutant was sequenced in order to verify the integrity of each sequence of interest and thus of the open reading frame. The mutations and the restriction sites added were checked at the same time.

C—Obtaining Chimeric Genes in a pKSII Cloning Vector

Each of the 19 sequences (1 wild type and 18 mutated) was placed downstream of a sequence coding for the mouse CD8a ectodomain, to give 19 constructs.

a) Preparation of a pKSII-CD8 Cloning Vector

The vector pKSII-CD8α (see FIG. 22) was digested successively with the restriction enzymes XbaI and NotI so that they could accommodate the inserts. Once the digestions had been accomplished, the plasmid was dephosphorylated, precipitated from ethanol and purified on 0.8% agarose gel.

b) Preparation of Inserts

The various inserts boxed in by the restriction sites XbaI-NotI were digested by the same restriction enzymes as the plasmid so that it could integrate them.

c) Obtaining Chimeric Plasmids by Cloning

The DNAs were inserted into the linearized pKSII-CD8α plasmid:

The digested inserts were purified on 2.5% agarose gel. They were re-inserted into the vector pKSII-CD8α using the gel ligation technique. A fragment of virgin gel served as the negative ligation control.

Having used the same restriction enzymes for the vector and the inserts, they thus had cohesive, complementary XbaI and NotI sites: the plasmid and inserts should be able to establish bonds between them. An enzyme, ligase, catalyzes the formation of a phosphodiester bond between a 3'-OH end and a 5'-phosphate end of the two nucleic acids.

Once the ligation was complete, DH5α bacteria are transformed by these plasmids carrying the ampicillin resistance gene. After culturing the various transformed bacteria at 37° C. on LB/agar (50 μg/mL of ampicillin) and comparison with the negative controls, it was observed that colonies only developed in the cells transformed by the ligation products in the presence of the CD™ insert. This suggests that the colonies obtained had indeed been transformed by a vector containing an insert between the sites XbaI and NotI.

d) Screening:

In order to confirm that chimeric plasmids had been obtained, various clones of each mutant were screened by digesting plasmid DNA using the two enzymes XhoI/NotI and after migration of the digestion products on 0.8% agarose gel. This double digestion excised the whole of the chimeric gene that had been created, i.e. with the CD8α in phase with the CD™.

For each clone and each construct (mutated or wild type pKSII-CD8α-CD™), a first band was observed at 2.9 kbp corresponding to the size of the linearized plasmid pKSII. A second band was observed at approximately 950 bp; it corresponded to the gene coding for the mutated or non-mutated CD8α-CD™ chimeras.

Figure 23:
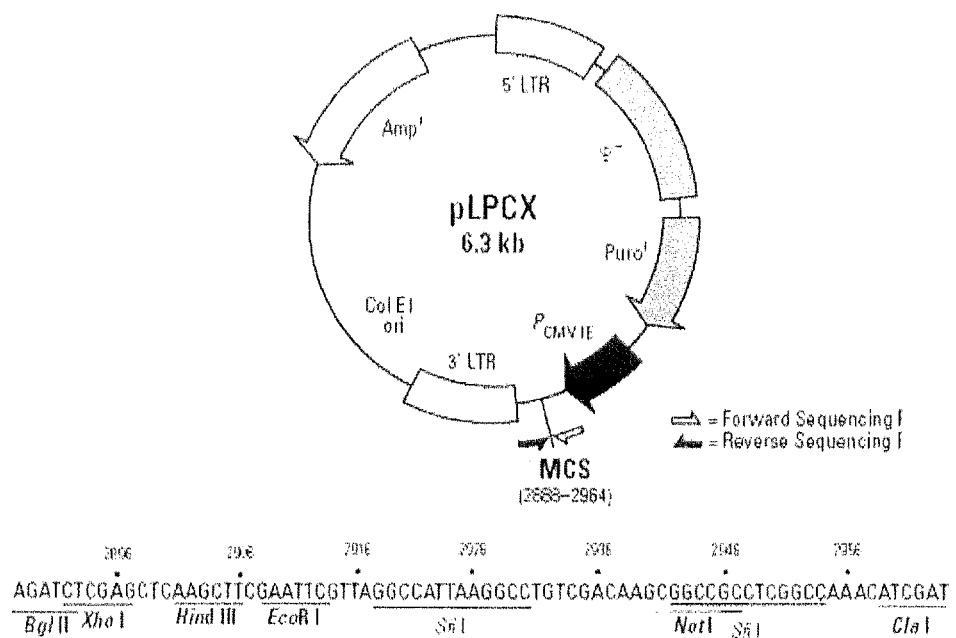
FIG. 23: Map of retroviral plasmid pLPCX used for the expression of chimeric genes. These genes were introduced into the multiple cloning site.

D—Obtaining Chimeric Genes in the Retroviral pLPCX Expression Vector:

Although the expression vector pKSII is easy to manipulate due to its size and its restriction sites, it does not enable protein expression in eukaryotic cells. Thus, we selected pLPCX (Clontech Laboratories Inc, see FIG. 23), which could introduce a gene both by transfection and by transduction using a retroviral vector.

Each chimeric gene was excised from the plasmid pKSII between the XhoI-NotI sites for purification by extraction on 2% agarose gel using the Nucleospin Extract II Kit® (Macherey-Nagel).

The pLPCX expression vector had also already been digested by the enzyme pair XhoI-NotI, dephosphorylated then precipitated with isopropanol (this step could eliminate the short DNA fragment (less than 100 bp) located between XhoI and NotI liberated during digestion).

The ligation of the chimeric genes with pLPCX was carried out using T4 DNA ligase (Biolabs) (insert/vector ratio approximately 3/1 molecule to molecule). The chemocompetent bacteria Stbl2 (MAX Efficiency® Stbl2™ Competent Cells, Invitrogen) were transformed by these ligation products. A positive control (1 ng of plasmid pUC19) and a negative control (pLPCX "ligated" without insert) were prepared at the same time. Following bacterial culture at 30° C. on gelose medium containing 50 μg/mL of ampicillin, only the bacteria transformed by the positive control or by the ligation products with inserts had developed.

Figure 24:
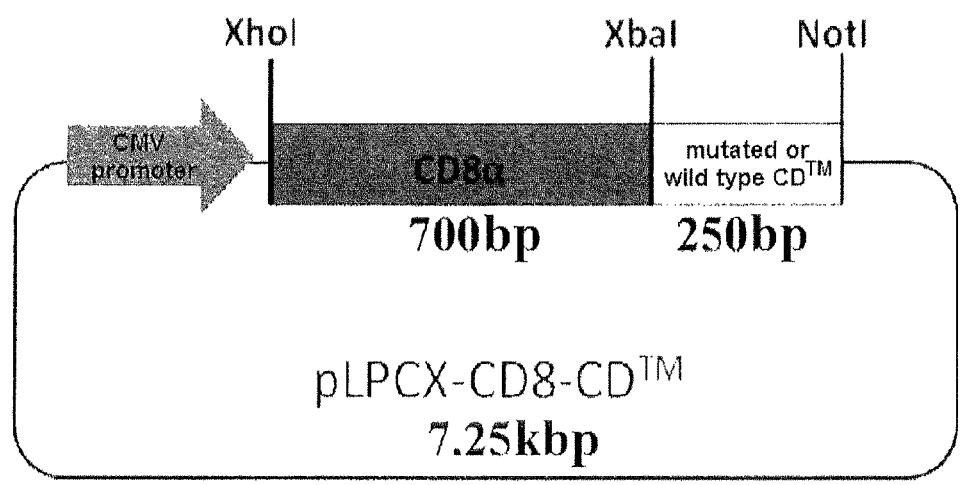
FIG. 24: Map of final chimeric constructs cloned into the retroviral pLPCX expression vector.

In order to be able to carry out the screening and to have a substantial quantity of plasmid DNA necessary for the transfections in eukaryotic cells, Midipreparations were carried out. The presence of inserts in the plasmid was verified on agarose gel 2% after digestion by XhoI then NotI. For each construct (mutated and wild type pLPCX-CD8α-CD™; see FIG. 24) a band was observed at 6.3 kbp, corresponding to linearized pLPCX and a band at 950 bp, corresponding to the excised chimeric genes.

2—Expression and Analysis of Targeting to Exosomes:

A—Transfections in HEK293T Cells:

In order to ensure transfection of the eukaryotic cells HEK 293T and to estimate the percentage of transduced cells, the cells were transfected with the plasmid containing the LacZ gene and incubated in a solution of X-Gal.

Initially by eye and then by optical microscope observation (magnification×40), we observed that more than 50% of the cells had been stained blue, which proved that the vast majority had been translated by the plasmid LacZ. The same conditions were used for transfection of our chimeric genes, and so it was probable that more than 50% of the cells had been translated by the chimeric genes.

At the same time, twenty simultaneous transfections were carried out in HEK 293T cells. They correspond to each of the plasmids and to a negative control (pLPCX-CD8 without CD™).

B—Expression of Chimeric Proteins in the Cell and Targeting to Exosomes a) Western Blot Analysis:

The cellular and exosomal lysates derived from the transfections were analyzed by migration on 10% SDS-PAGE gel followed by transfer onto a PVDF membrane (polyvinylidene difluoride, Immobilon-P, Millipore). These membranes were then revealed using a primary anti-rabbit CD™ serum followed by a secondary anti-rabbit IgG antibody coupled to peroxidase. After revealing, these antibodies were eliminated and the transfer membranes were revealed in the same manner but using an anti-rabbit CD8α serum.

Figure 25:
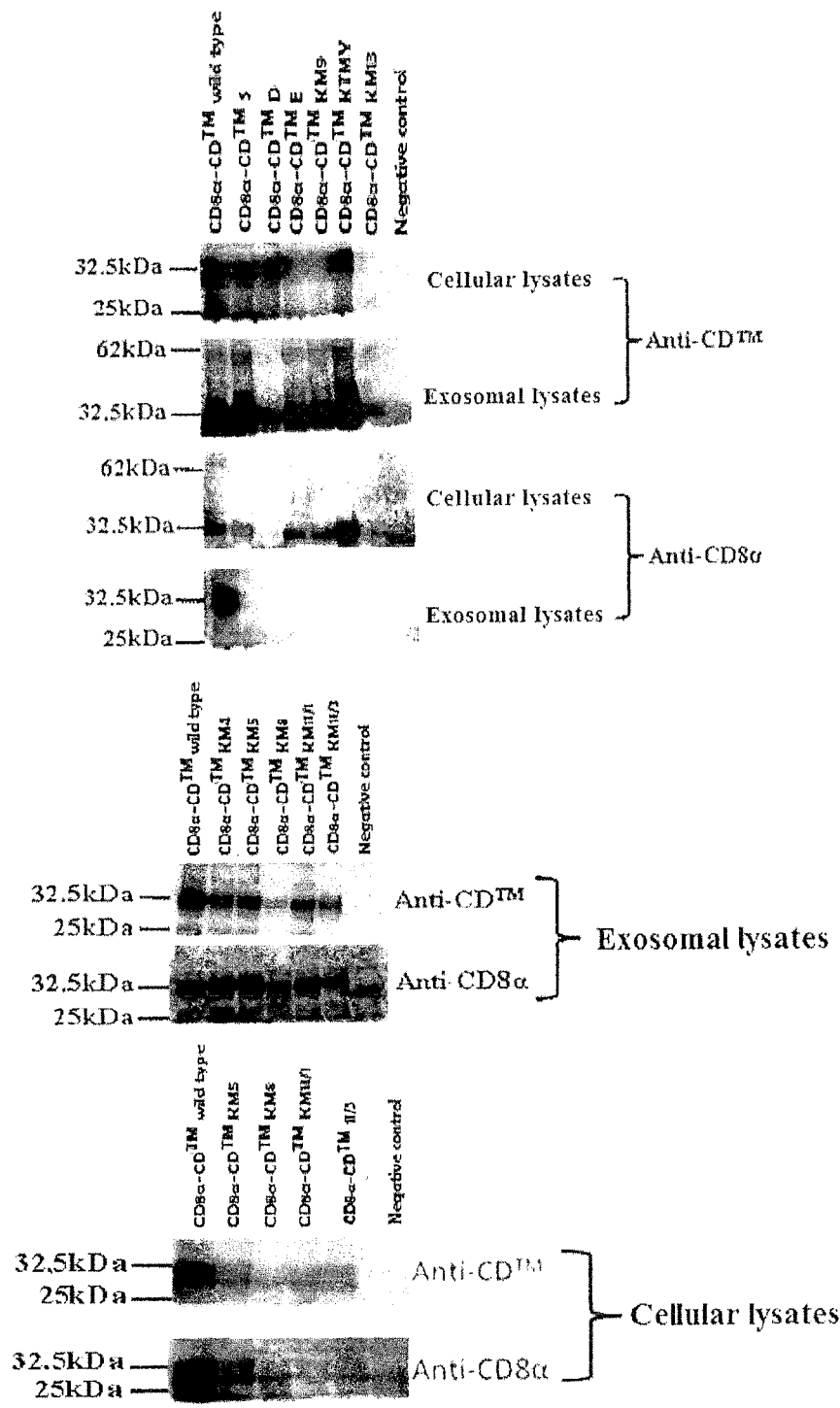
FIG. 25: Visualization of the expression and exosomal targeting of chimeric proteins. anti-CD™ and anti-CD8α Western Blot for the cellular and exosomal lysates of the set of mutant and wild type CD8α-CD™ proteins (size varying from 31 kDa to 27 kDa) as well as of the negative control (pLPCX expression vector containing the CD8α alone). The anti-CD™ and anti-CD8α rabbits' serums were diluted to $1/200^{th}$. The secondary anti-rabbit IgG antibody coupled to peroxidase was diluted to $1/5000^{th}$.
Figure 26:
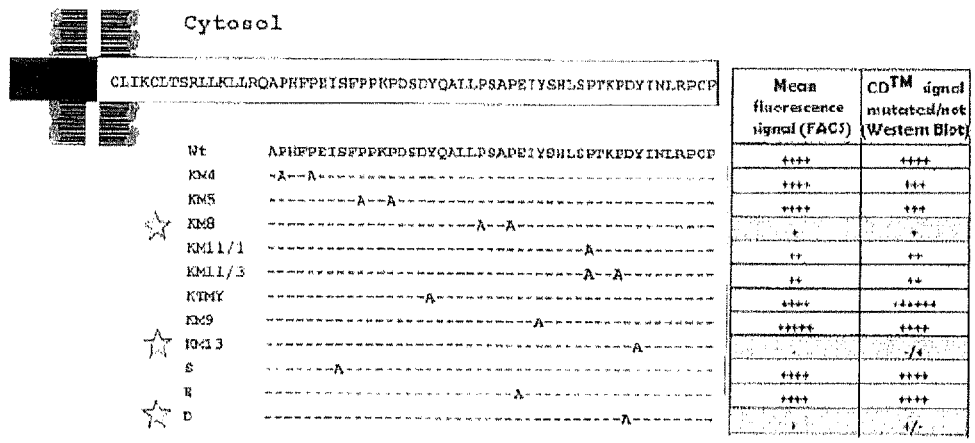
FIG. 26: Results comparing experiments for detection of CD8α associated with exosomes by flow cytofluorometry and Western Blot. Table giving the results of expression and targeting to exosomes of the various chimeric proteins that were analyzed. The mutants indicated by a star are significant for exosomal targeting. The presence of CD8α on the exosomes was recorded by flow cytofluorometry by means of a fluorescent mouse monoclonal antibody specific for a conformational epitope of the CD8α protein (antibody 53-6.7 from Pharmingen).

The results are presented in FIGS. 25 and 26.

Comparison of Levels of Expression of Chimeras in Cells and Exosomes:

It was observed that the cellular lysates revealed only low expression of the chimeric proteins. In contrast, the presence of certain chimeric proteins in the exosomes was sometimes very strong.

In addition to the degrees of expression, the major difference which should be noted between cellular proteins and exosomal proteins is the presence of 2 or 3 bands for the cells and a single band for the exosomes. This arises from the fact that the cell contains non-glycosylated forms and forms that are glycosylated to a greater or lesser extent. Only the correctly glycosylated form is found in the exosomes.

Western Blot Analysis of Exosomal Targeting of Positive (CD8α-CD™) and Negative (CD8α Alone) Controls:

With the anti-CD™ serum, a band migrating to 31 kDa was present in the exosomal lysate of the wild type CD8α-CD™ control while it was absent in the lysate from cells transfected by the negative control. This band is characteristic of the expected chimeric protein.

With the anti-CD8α serum, the CD8α negative control alone exhibited a band at approximately 27 kDa, which corresponded to the expression and exosomal targeting of CD8α deprived of CD™. As before, a band migrating to 31 kDa was present in the exosomal lysate of the wild type CD8α-CD™ control. The difference in intensity between the 31 kDa and 27 kDa bands indicates that the CD8α is indeed targeted better on exosomes when it is fused to CD™.

Western Blot Analysis of Variations in Targeting Mutated CD8α-CD™:

Only the results obtained with the anti-CD8α serum are mutually comparable. The results obtained with the anti-CD™ serum were only used to confirm the preceding results. Depending on the mutation of the sequence coding for the CD™, these results show a variation in the expression and targeting of chimeric proteins to exosomes. This is particularly clear for mutations that strongly inhibit the targeting of proteins on exosomes. The mutants concerned were the mutants KM8, KM13, D and KS8.

It can be concluded from these observations that the motif PSAP (mutant KM8) and the motif DY (at the last motif YxxL (mutants KM13 and D)) are important for exosomal targeting.

b) Quantification of Chimeric Proteins on Exosomes by FACS:

The presence of chimeric proteins was also investigated by cytofluorometric analysis (FACscan) using a fluorescent anti-CD8 monoclonal antibody.

After fixing the exosomes onto latex beads (IDC (Interfacial Dynamics Corporation) ultraclean aldehyde/sulfate Latex beads), the chimeric proteins present at the surface of the exosomes were tagged using an anti-CD8α mouse monoclonal antibody coupled to fluorescein (antibody 53-6.7 from Pharmingen) and analyzed using a cytofluorimeter (FACScan).

Figure 27:
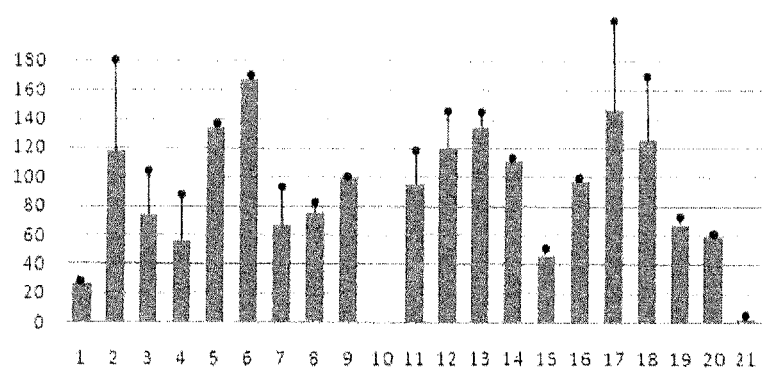
FIG. 27: Expression of CD8 at the surface of exosomes. Histogram representing the mean of measurements of the exposure of each chimeric protein at the surface of the exosomes. These measurements were carried out by flow cytofluorometry. The exposure of each chimeric protein is expressed as a percentage with respect to the exposure of the wild type CD8a-CDTM chimeric protein (construct n° 9 on the histogram=100%). The standard deviation is indicated. The chimeric proteins analyzed were: 1: negative control (pLPCX expression vector containing the CD8α alone); 2: KS5; 3: KS6; 4: KS8; 5: KS9; 6: KS10; 7: KS12; 8: KS14; 9: wild type sequence; 10: no construct; 11: KM4; 12: KM5; 13: S; 14: KTMY; 15: KM8; 16: E; 17: KM9; 18: KM11/1; 19: KM11/3; 20: D and 21: KM13. The results observed confirm the results presented in FIGS. 25 and 26.

The results obtained are particularly clear for the mutants KM8, KM13 and D, which reveal the importance of mutated amino acids for targeting chimeric proteins on exosomes (see FIGS. 26 and 27). These results confirm the impact of the motifs PSAP, D and Y (from the motif DYxxL) in targeting proteins to exosomes already revealed by the Western Blot results.

Conclusion:

During this study, we constructed chimeric genes that could express the mutated or wild type pilot peptide CD™ fused with mouse CD8α. These mutations on the amino acids or particular motifs of CD™ were intended to identify the amino acids and consensus motifs that are of importance for exosomal targeting.

The various chimeric genes were integrated into a retroviral expression vector in order to transfect the eukaryotic HEK293T cells in order to obtain expression of these chimeric proteins. The bands observed using Western Blot suggest that, like the native CD8α protein, these proteins are differently glycosylated during their passage through the Golgi apparatus. Only correctly glycosylated proteins would be found in the exosomes. These proteins underwent suitable post-translational modifications, a condition vital to expression of conformational epitopes essential to the future development of a vaccine immunity or to screening of therapeutic molecules. However, these glycosylations, which are present to a greater or lesser extent, result in multiple diffuse bands that obstructed us during comparative quantification of the proteins. To overcome this problem, the lysates had to be treated with an endoglycosylase in order to observe a single band on the gel.

These results showed that the motifs PSAP and DY (from the last YxxL) are indispensable to the expression and targeting of chimeric proteins to exosomes. These results are novel and are interesting both from a fundamental viewpoint and from the viewpoint of industrial application.

It is probable that the motif PSAP is responsible for an interaction with the Tsg101 protein of the ESCRT complex. As regards the motif DYxxL, it could be involved in the interaction with the protein ALIX of the ESCRT complex. Thus, for the first time, experimental data suggest that the ESCRT complex is involved in the formation of exosomes.

Example 3

Targeting of Receptors with Transmembrane Domains to Exosomes

Membrane receptors are major targets for the development of therapeutic molecules. In general, high throughput screening of drugs is carried out using receptors with multiple membrane domains expressed on cells under culture. In addition to the difficulties in obtaining strong expression of the receptors on the cell surface, this technique gives rise to difficulties in automation. However, this is currently the only solution since using purified recombinant receptors is for now technically unfeasible.

In this context, exosomes carrying receptors, in particular multiple domain receptors, would be simple to use and well suited to screening because of their stability and ease of manipulation.

The aim of the present study was to produce exosomes carrying receptors with single or multiple transmembrane domains, in particular the CxCR4 receptor (receptor for the chemokine SDS-1 (CXCL-12) and for HIV) and the CD4 receptor (receptor for HIV).

Three chimeric genes were synthetized. They comprised, at the 3' end, the peptide CD™-BLV with sequence SEQ ID. NO. 8, and at the 5' end, a DNA coding for the CxCR4 human receptor, for a version of the CxCR4 receptor truncated at the C-terminal portion comprising 307 amino acids (CxCR4 (307)) or for a version of the CD4 receptor truncated at the C-terminal portion comprising 403 amino acids (CD4 (403)).

The receptors CD4 and CxCR4 respectively comprise one and seven transmembrane domains.

The three chimeric genes were cloned in a retroviral pLPCX expression vector. These various plasmids were transfected in HEK293T human eukaryotic cells in order to observe the expression of the various chimeric proteins in these cells as well as their sorting to the exosomes.

The cloning and sub-cloning strategy used was similar to that described for Example 2:

The DNAs coding for the receptors CxCR4, CxCR4 (307) and CD4 (403) as well as that coding for the pilot peptide CD™ were amplified by PCR using primers comprising the sequences for restriction sites that were to be integrated at each end of the amplified fragments (the fragments CxCR4, CxCR4 (307) and CD4 (403) will be flanked at the 5' end by the site EcoRI and at the 3' end by the site XbaI, and CD™/BLV will be flanked at the 5' end by the site XbaI and at the 3' end by the site NotI).

Figure 20:
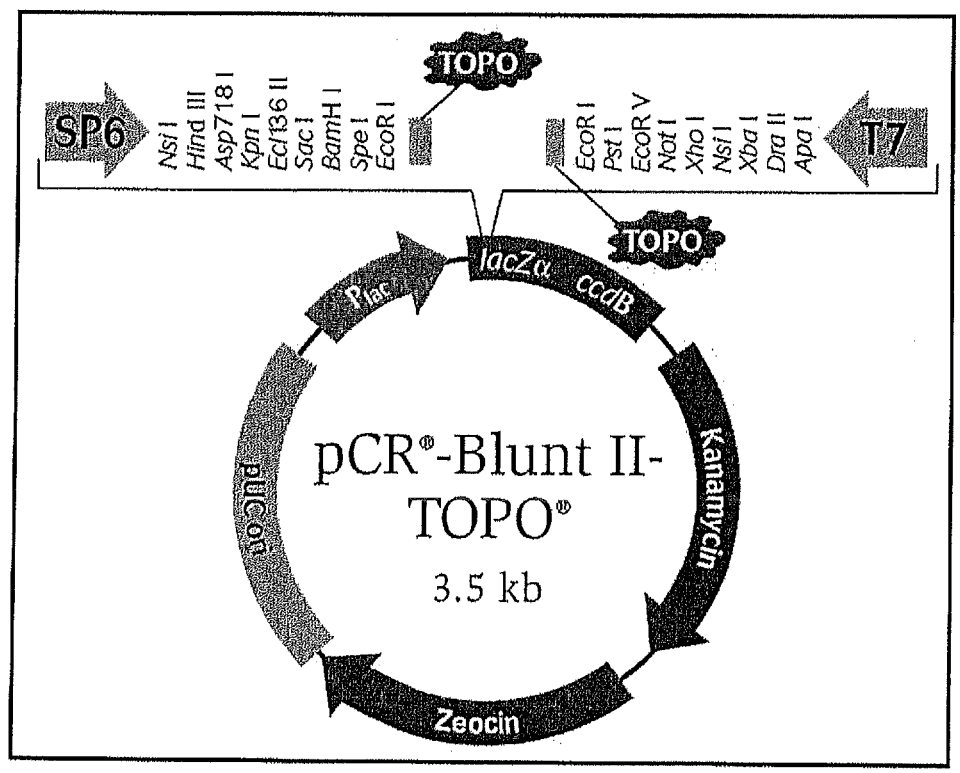
FIG. 20: Map of TOPO® (PCR-Blunt II-TOPO) plasmid used to clone the various PCR products. The TOPO vector supplied in the TOPO-blunt cloning kit (Invitrogen) was linearized and had, at each of its 3'-phosphate ends, the topoisomerase I of the vaccinia virus, which meant that the PCR products could be ligated with the linearized TOPO vector.

The inserts thus produced are cloned into TOPO amplification vectors (see FIG. 20). The plasmids obtained are then digested by restriction enzymes and analyzed on 1.5% agarose gel, then sequenced to check the integrity of their sequence.

Figure 21:
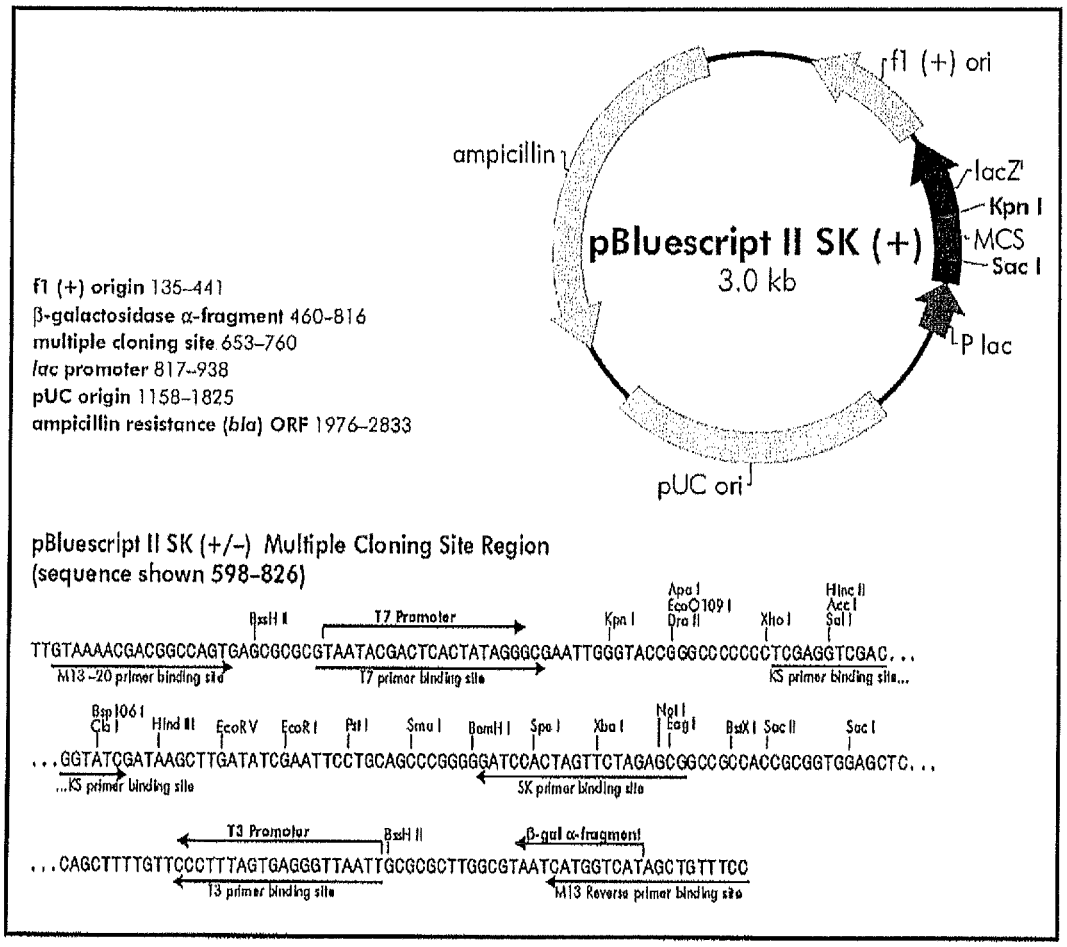
FIG. 21: pBluescript II KS (+) expression vector.

The insert CD™/BLV is then excised from the TOPO vector by enzymatic digestion using the XbaI/NotI pair then sub-cloned into the amplification vector pKS2 (see FIG. 21). The recombinant vector pKS2 as well as the recombinant TOPO vectors containing the inserts CxCR4, CxCR4 (307) and CD4 (403) are then digested with the restriction enzymes EcoRI and XbaI, in order to be able to sub-clone the fragments CxCR4, CxCR4 (307) and CD4 (403) in the amplification vector pKS2, said fragments being placed at the 5' end of the sequence coding for the peptide CD™.

Figure 22:
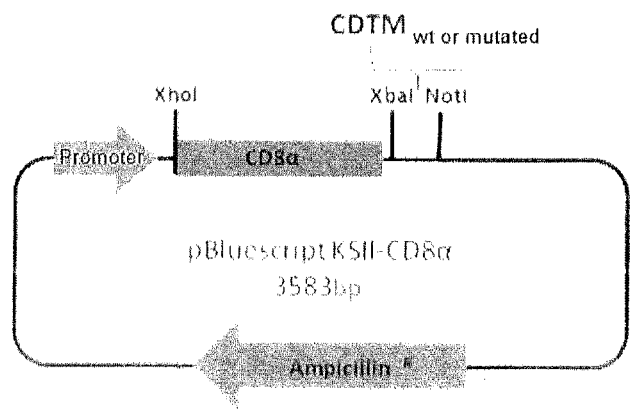
FIG. 22: Map of plasmid pKSII-CD8α.
Figure 28:
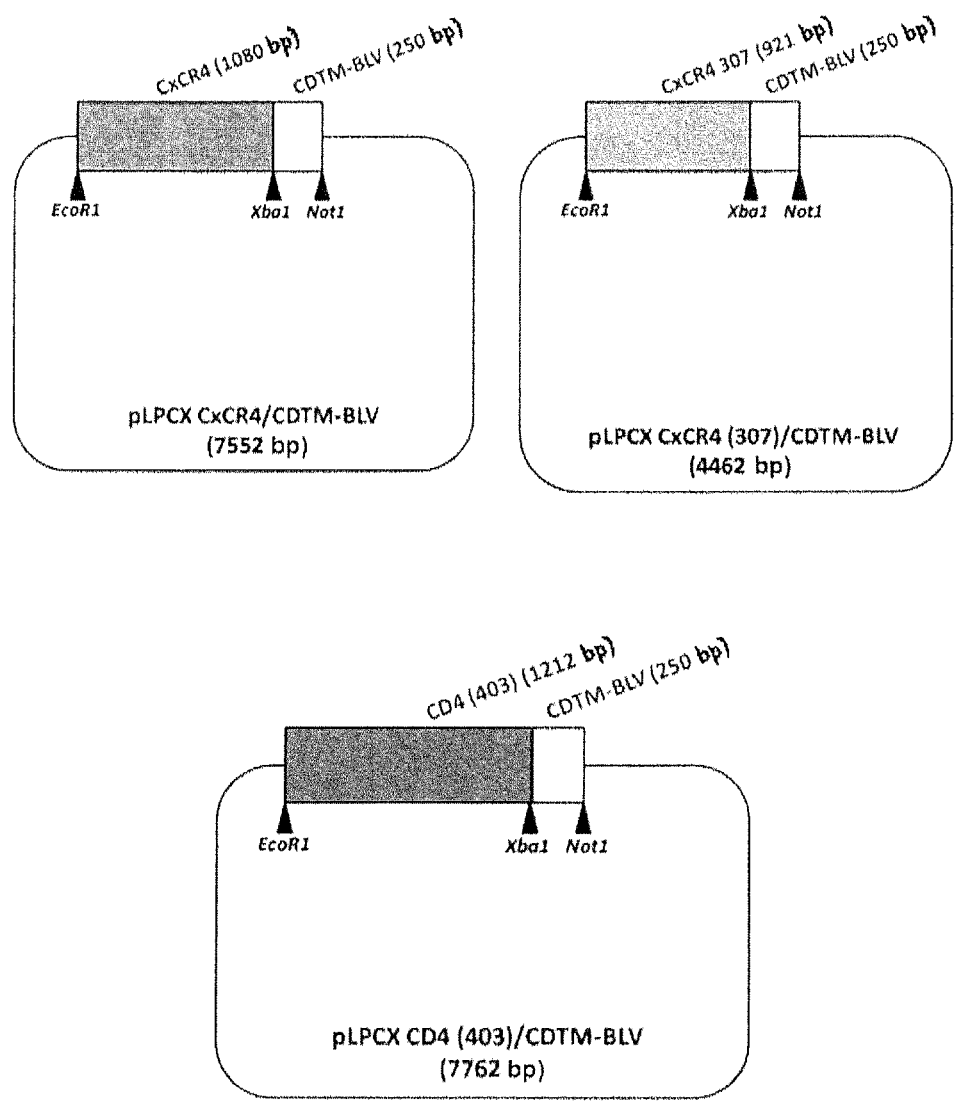
FIG. 28: Representation of different pLPCX expression plasmids obtained after cloning chimeric genes coding for proteins with single or multiple transmembrane domains.

The various constructs thus obtained were excised from the recombinant pKS2 plasmids by digestion with the enzyme pair EcoRI/NotI then sub-cloned into the retroviral pLPCX expression vector (see FIG. 22). The vectors obtained (see FIG. 28) are verified by enzymatic digestion using the EcoRI/XbaI enzyme pair.

The various pLPCX plasmids are transfected into HEK293T human eukaryotic cells in order to express the chimeric proteins CxCR4/CD™, CxCR4(307)/CD™ and CD4 (403)/CD™.

An extract of total cellular proteins (100 µg) and proteins of a suspension of exosomes produced by each of the batches of transfected cells then undergo SDS-PAGE (10%) migration in the presence or absence of β-mercaptoethanol. The proteins of interest are revealed by Western Blot using a primary anti-rabbit CD™ serum and secondary anti-rabbit IgG antibody coupled to peroxidase. Revealing of the antibodies was carried out in a dark room using an ECL solution.

Finally, the protein fingerprint of each sample is revealed by staining with Coomassie Blue.

Figure 29:
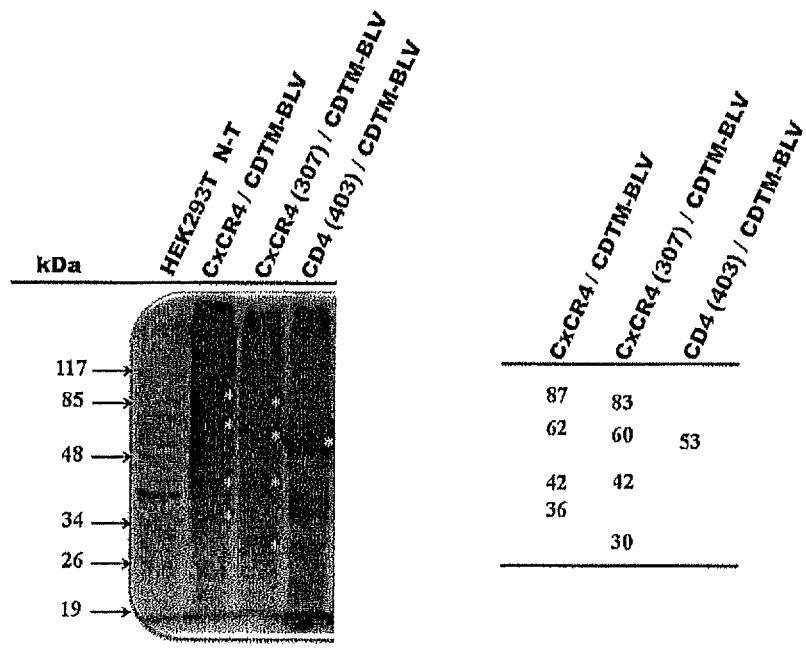
FIG. 29: A. Western Blot analysis of anti-CD™-BLV carried out on the cellular protein extracts from HEK293T cells not transfected (N-T) or transfected with the pLPCX expression vectors containing the three constructs coding for the three chimeric proteins. The primary rabbit anti-CD™-

The results are presented in FIGS. 29-31.

It will be observed that the chimeras CxCR4/CD™, CxCR4 (307)/CD™ and CD4 (403)/CD™ are expressed in the cellular protein extracts (see FIG. 29).

Several bands characterize the chimera CxCR4/CD™; 36, 42, 62 and 87 kDa. The expression of wild type CxCR4 receptor is characterized by a plurality of isoforms, in particular in HEK293T cells; 34, 40, 47, 62, 73 and 80 kDa bands may be identified (Sloane J A, et al.). The larger sizes for the bands of the chimera CxCR4/CD™ in HEK293T are due to the presence of pilot peptide (CD™ domain) in the chimera CxCR4/CD™. Similarly, the 30, 42, 60 and 83 kDa bands reveal the presence of the chimera CxCR4 (307)/CD™. The variation in size of the bands representing the various isoforms of this chimera is explained by the fact that the CxCR4 receptor is truncated. As for the chimera CD4 (403)/CD™, it is characterized by a clearly visible band at 53 kDa.

Further these chimeras were all sorted to exosomes as shown by the presence of 36, 42, 62 and 87 kDa bands (for CxCR4/CD™); 30, 38, 48, and 83 kDa bands (for CxCR4 (307)/CD™) and the 53 kDa band (for CD4 (403)/CD™) (see FIG. 30).

Using Coomassie Blue to reveal the various protein fingerprints shows that the quantities of total proteins of exosomal origin (FIG. 31B) used during these experiments are substantially smaller than the quantities of total proteins of cellular origin (FIG. 31A), while the Western Blot signal is equivalent. It will be seen that all of the proteins present in the control cellular lysate are not sorted to exosomes. The chimeras CxCR4/CD™ and CD4(403)/CD™ are addressed very strongly to the exosomes. In contrast, the chimera CD4 (403)/CD™ is practically entirely sorted to exosomes.

Conclusion

The transfection of HEK293T cells with differents pLPCX plasmids enabled the expression of the chimeras CxCR4/CD™-BLV, CxCR4(403)/CD™-BLV and CD4 (403)/CD™-BLV. The Western Blot analysis demonstrated their presence in cellular lysates.

As expected, a plurality of isoforms of the chimeras CxCR4/CD™-BLV and CxCR4 (307)/CD™-BLV are expressed in HEK293T cells transfected with the plasmids pLPCX CxCR4/CD™-BLV and pLPCX CxCR4 (307)/CD™-BLV. The chimeras CxCR4/CD™-BLV and CxCR4 (307)/CD™-BLV are effectively sorted to exosomes and it appears that these fusion proteins are shared in equal parts in the cells and the exosomes.

Further, the presence of the chimera CD4 (403)/CD™-BLV in HEK293T cells transfected with the plasmid pLPCX CD4 (403)/CD™-BLV was observed. It appears that the pilot peptide CD™-BLV promotes very substantial sorting of the chimera CD4 (403)/CD™-BLV to exosomes.

The results described above show that the pilot peptide CD™-BLV is capable of sorting both single and multiple transmembrane domain proteins to the exosomes.

It is known that it is very difficult to work on these receptors in solution as when they are not integrated into a plasma membrane, they do not retain their native structure. Current studies being carried out on these proteins often start from stable cell lines expressing the receptors of interest. However, it is restricting in terms of time and cost to collect, culture and maintain these lines, which may die at any time if they are poorly treated. For this reason, the fact of using exosomes carrying receptors with multiple transmembrane domains for their studies represents an interesting solution as exosomes have all the advantages of a cell in these studies without the disadvantages since they are not alive.

Exosomes in the membrane into which the recombinant proteins are integrated, and in particular proteins comprising multiple transmembrane domains, could be used for vaccinology and as a screening tool.

Example 4

We have discovered that a fragment of the C-terminal end of the TM protein of BLV mutated by a deletion of a peptide and by a substitution of a cysteine for an alanine displays enhanced targeting properties to the exosomes of a peptide or polypeptide of interest fused with it. The analysis of the amino acids involved in this exosomal targeting property reveals that this peptide interacted with proteins of the ESCRT budding machinery. It is known that this machinery interacts with transmembrane proteins (for example receptors) and also with cytoplasmic proteins (Hrs, virus capsid, for example) that interact with the membrane to which they bind while remaining cytosolic. We thus wished to know whether a cytosolic chimeric or nuclear protein to which two properties were added, one of binding to the internal face of membranes and the other of exosomal targeting, would be effectively sorted to exosomes. To this end, we used an internal protein of the cell involved in nucleotide metabolism, namely the SNAP protein, to demonstrate this hypothesis (Covalys, NEB).

The SNAP protein is the commercial name used by NEB (New England Biochemical, Ipswich, Mass., USA) for a mutant of the enzyme O6-alkylguanine-DNA alkyltransferase (hAGT). It is involved in the nucleotide synthesis pathway (in the repair of DNA). We used DNA from the plasmid pSNAPm from NEB as matrix DNA for PCR amplifications of the DNA fragment fused between the Src and CDTM fragments. The SNAP protein may bind a plurality of substrates (Keppler et al, 2002; Keppler et al, 2004).

Properties of interaction with cellular membranes are common to many cellular proteins, in particular proteins involved in signaling. These proteins interact with the membrane via fatty acids that they acquire post-translationally and also by the presence of basic amino acids that interact with the polar heads of certain fatty acids of the membrane (for example choline). These fatty acids are generally myristic acid, palmitic acids or geranyl-geranyl.

The prototype of these proteins is the oncogene c-Src that has a myristylable glycine in position 2 and many N-terminal lysines and arginines. It is known that, when it is fused to a cytoplasmic protein, this N-terminal fragment provides it with the property of binding to the internal face of cellular membranes. Many other protein fragments (in particular cellular or viral proteins) that bind under the membranes could act in the same way as that of the N-terminal fragment of c-Src if these fragments were fused with a cytoplasmic protein. The localization of the fused fragment must conserve the membrane fixing properties. In addition, it may be preferable (but not necessarily obligatory) for the infra-membrane target peptide to be localized in the N-terminal end of the fusion protein. As an example, myristylation of c-Src occurs only on the glycine in position 2. For other acylations, for example palmitylation, the position of the substituted amino acids is generally further inside the protein sequence.

The CD™ sequence for exosomal targeting used in the chimeric polypeptide of the invention may vary (see, for example, the many mutants of the CD™ sequence in the preceding examples), but it must contain at least the sequence PSAP (or PTAP) and YxxL to be fully effective. Localization of this CD domain in the chimeric polypeptide of the invention does not appear to be crucial for the property of targeting to exosomes. However, the optimal localization of said CD domain in the chimeric polypeptide of the invention is the C-terminal position.

In the chimeric polypeptide of the invention, the peptide or polypeptide of interest to which these two peptides (the CD domain or its mutated derivative and the infra-membrane targeting domain) are added so that it acquires exosomal targeting may have different natures:

For example, it may be the SNAP protein, as in the polypeptides SNC and DSC described hereinafter. In this case, it is possible to use the properties of this SNAP protein (as described, for example, by Keppler et al, 2002 and Keppler et al, 2004), to introduce a fluorophore or a biotin or any other molecules into a particular site in the exosome, for example to a protein termed the G protein.

Alternatively, the peptide or polypeptide of interest of the chimeric polypeptide of the invention may also be a particular enzyme. The exosome may thus be used as a vehicle that can deliver this enzyme (in particular cytosolic enzyme) to a cell (in particular a cell of a human or non-human host) or to an organ deprived of this enzymatic activity. This may in particular be used to treat patients with a disorder due to a metabolic or functional deficit.

Alternatively, the peptide or polypeptide of interest of the chimeric polypeptide of the invention may be an antigen (pathogenic, tumors or others). The exosome containing it may thus prompt an immune reaction against this antigen, which would be particularly effective since exosomes are known to be captured by immune response cells (in particular by dendritic cells).

Alternatively, the peptide or polypeptide of interest of the chimeric polypeptide of the invention may be a protein specifically binding a nucleic sequence (for example a DNA). The exosome of the invention may then bind a nucleic acid that is readily detectable by PCR, for example, enabling diagnostics to be carried out. An example of a technique for specific binding of a protein to a RNA is given in the article by Bertrand et al. (1998). The technique described by Bertrand et al. is based on the use of the capsid protein of the single strand RNA MS2 phage (Fouts et al, 1997) and of a RNA containing a plurality of copies of a 19 nucleotide sequence recognized by this protein.

I. Synthesis of a Chimeric Gene

We wished to combine the properties of infra-membrane targeting of the N-terminal fragment of the c-Src protein with the properties we discovered of interaction of the peptide CDTM15 derived from the TM protein of BLV (bovine leukemia virus) with the machinery for targeting to exosomes. We believed that we would thus facilitate the interaction of CDTM with the proteins of this machinery. Our prototype integrated a reporter protein, the SNAP protein (Covalys and NEB). This protein could be replaced by any other protein of interest. For this purpose, we created the chimeric gene Src-SNAP-CDTM (SEQ ID NOs: 121; 122) which codes for the chimeric protein SSC (for Src-SNAP-CDTM; SEQ ID NOs: 123; 124).

The synthesis of the chimeric gene coding for the SSC protein was accomplished in a plurality of steps. Firstly, a synthetic 75 nt DNA coding for the N-terminal end of the protein c-Src was obtained. Next, we carried out separate amplification of 3 DNA fragments: a) the synthetic DNA bordered by the enzyme sites EcoRI upstream and Nhe I downstream; b) the DNA coding for the SNAP protein (NEB) bordered by the sites Nhe I upstream and SbfI and AscI downstream; c) the DNA coding for a CDTM fragment with the sites SbfI and AscI upstream and NotI downstream. Finally, an amplification was carried out simultaneously using the three preceding DNA fragments, the sequences of which overlapped, as the matrix DNA; this latter amplification enabled a DNA connecting the three fragments together in the order Src-SNAP-CDTM to be produced.

1) Preparation of a Synthetic DNA

The following 5 oligonucleotides were synthesized by MWG:

```
                                        (SEQ ID NO: 108)
S1(5'GCCACCATGGGCAGCAGCAAGAGCAAGCCCAAGGAC 3'), (SEQ ID NO: 109)
S2(5'P-CCCAGCCAGCGCCGCCGCAAGTCTAGAGGCCCGGGAGGC

3'), (SEQ ID NO: 110)
AS1(5'GCCTCCCGGGCCTCTAGACTTG 3'), (SEQ ID NO: 111)
AS2(5'P-CGGCGGCGCTGGCTGGGGTCCTTGGGCTTGCTCTT3')

(SEQ ID NO: 112)
AS3(5'P-GCTGCTGCCCATGGTGGC 3').
```

DNA synthesis: 20 µL of each oligo are mixed in equimolar quantities (100 µM of S1, S2, AS1, AS2 and AS3). 11 µL of 10× ligation buffer (NEB) was added. A single cycle is carried out in the PCR apparatus: 95° C., 2 min, followed by dropping temperature on the bench to 25° C. 9 µL of 10× ligation buffer, 81 µL of H$_2$O and 1 µL of T4 DNA ligase (NEB) are added to 10 µL of mixed hybridized oligos. Ligation was carried out at 22° C., 10 min.

The synthetic DNA is then amplified by PCR in a mixture containing 10 ng of matrix DNA, the primers S1 and AS1, 4 dNTPs, the 1× buffer and 2.5 U of Pfu Turbo DNA-polymerase (Stratagene) under the conditions set by the supplier of the enzyme. After 2 min of denaturing at 95° C., 25 amplification cycles (95° C. 30 sec, 67° C. 30 sec, 72° C. 5 sec) were carried out.

2) Amplifications by PCR, individual, of each of the 3 DNA fragments constituting the Src-SNAP-CD™ gene in order to graft common sequences carrying restriction endonuclease sites to each of their ends. The nucleotide sequence of the Src fragment (coding for the infra-membrane targeting domain or domain (ii)) is SEQ ID NO: 120. The nucleotide sequence for the CD™ fragment (coding for the CD domain or domain (iii)) is SEQ ID NO: 120.

The 3 amplifications are carried out under the conditions and following the recommendations of Finnzyme, supplier of the Phusion DNA polymerase used.

a) Amplification of the Src fragment and addition of the restriction sites are carried out using the synthetic DNA obtained as above and the following primers:

```
R1Sre
                                        (SEQ ID NO: 113)
(GAATTCGCCACCATGGGCAGCAGCAAGAGCAAG)
and SrcNhe1
                                        (SEQ ID NO: 114)
(CATGCTAGCGCTGCCTCCCGGGCCTCTAGACTTTC).
``` b) Amplification of the SNAP fragment and addition of the restriction sites are carried out using the DNA from the plasmid pSNAP (NEB) and the following primers:

```
NheSNAP
                                        (SEQ ID NO: 115)
(GGAGGCAGCGCTAGCATGGACAAAGACTGCGAAATGA)
and SNAPSbfAsc
                                        (SEQ ID NO: 116)
(GCGCGCCGCTTCCTGCAGGACCCAGCCCAGGCTTG).
``` c) Amplification of the DCTM fragment and addition of the restriction sites are carried out using a DNA coding for the C-terminal end of the TM of BLV for which the C-terminal cysteine is mutated in alanine; it is carried out using the following primers:

```
SbfAscDCTM15
                                        (SEQ ID NO: 117)
(CCTGCAGGAAGCGGCGCGCCCCACTTCCCTGAAATC)
and DCTM15Not
                                        (SEQ ID NO: 118)
(GCGGCCGCTTCGAACTCGGTGCTGGCAGCAAGA).
```

3) Amplification to Obtain the DNA Src-SNAP-DCTM.

The preceding 3 DNA fragments are purified on gel. Amplification of the mixture of these 3 DNAs as a matrix is carried out in the presence of the primers R1Src and DCTM15Not (see above) under the conditions and using the recommendations of Finnzyme, supplier of the Phusion DNA polymerase used. The DNA obtained fuse the preceding 3 DNAs in phase.

II. Cloning into the Cloning Vector PCR® BluntII-TOPO®

1) Ligation of PCR Products into the Cloning Vector PCR® BluntII-TOPO®

Ligation is accomplished with the aid of a linearized plasmid vector having topoisomerase I enzymes at its ends (cf. FIG. 6), thus enabling the insert to be integrated without involving a ligase. In addition, this vector has a blunt end either side of its ends and so the insert also has to have blunt ends in order to be able to ligate. In order to select the transformants, the plasmid has an antibiotic resistance gene: kanamycin.

The following are mixed in ice: 0.3 µL of PCR product, 0.25 µL of salt solution, 0.7 µL of sterile water and 0.25 µL of TOPO vector from the TOPO Blunt cloning kit (Invitrogen), i.e. 1.54 as a final concentration. It is incubated for 5 to 30 min at ambient temperature.

2) Transformation of TOP10 Chemo-Competent Bacteria

TOP 10 chemo-competent bacteria (10 µL) are transformed by the whole of the TOPO/insert ligation mixture. There was a positive transformation control (1 ng of PUC19: plasmid carrying the ampicillin resistance gene) and a negative control (TOPO plasmid without insert). After incubation for 30 min in the ice, a thermal shock is applied to the mixture for 30 sec at 42° C. The tubes are then immediately replaced in the ice. Next, 250 µL of SOC medium (Bacto-tryptone 2%, Bacto-yeast extract 0.5%, NaCl 0.05% and glucose 0.2%) is added and carefully homogenized with it and incubated for 1 h at 37° C. in a water bath for the time for phenotype expression. Finally, 150 µL of suspensions are seeded into a dish containing LB (Luria Broth)/agar with 50 µg/mL of kanamycin and incubated for 24 h at 37° C. In the dishes, colonies developed that had acquired the kanamycin resistance gene and thus which had the cloning vector, with or without the gene of interest. The clones are spread again and counted onto a second gelose dish, incubated for 24 h at 37° C. and liquid cultures of 10 mL (LB+100 μM kanamycin) of reseeded clones are produced for 16 h at 37° C. with agitation.

3) DNA Plasmid Minipreparation

The bacterial culture is centrifuged for 15 min at 3500 rpm and at 4° C. The pellet is taken up in 250 μL of A1 re-suspension buffer (plasmid DNA Purification Nucleospin kit (Macherey-Nagel)). The bacteria are lysed for a period of 5 min at ambient temperature with 250 μL of A2 lysis buffer. Next, 300 μL of A3 neutralization buffer is added and it is important to mix well by overturning to prevent production of a diffuse pellet. The tubes are centrifuged for 10 min at 11000 rpm and at 4° C. The supernatant is passed through a column placed on a collection tube; it is centrifuged for 1 min at 11000 rpm. After washing with 500 μL of A4 washing buffer, the column is dried for 2 min at 11000 rpm. 50 μL of elution buffer is passed through and the eluate is harvested in an Eppendorf tube. The DNA obtained is assayed by spectrophotometry at 260 nm.

4) Enzymatic Digestion (EcoRI) and Sequencing

In order to verify whether the plasmid DNA obtained is indeed recombined, the plasmids are digested with a specific restriction enzyme (Biolabs®), EcoRI, which framed the insertion site. Approximately 200 ng of each plasmid is digested with 4 units of enzyme. 1 μL of NEB1 10× buffer and sterile water are added to this to obtain a final volume of 10 μL. Digestion is carried out at 37° C. for 1 h. After identifying good clones on 2% agarose gel, 1.5 μg of plasmid DNA is sent for sequencing to Eurofins MWG Operon. This enables the integrity of each sequence to be verified by checking whether the restriction sites that had been added are indeed present as well as the mutation. Several clones are obtained, their plasmid DNA was analyzed and sequenced. Two plasmids are retained: the first, Src-SNAP-CDTM, represents the expected chimeric gene; the second, D-SNAP-CDTM, corresponds to a sequence having a deletion of a portion of the Src fragment that had to be produced during the last PCR. The protein coded by the D-SNAP-CDTM DNA also contains a glycine in a myristylable position but has lost a portion of its basic amino acids which reinforce the sub membrane anchoring properties.

III. Cloning into the Expression Vector pcDNA 3.1

1) Preparation of Expression Vector

The vector pcDNA3.1 is digested by the restriction enzymes EcoR1 and NotI, then dephosphorylated and extracted with phenol/chloroform.

Precipitation with isopropanol enabled the short DNA fragment (<100 bp located between EcoR1 and NotI) released during digestion and which could have re-ligated with the plasmid to be eliminated. 0.15 times the volume of 3M sodium acetate and 0.6 times the volume of cold isopropanol are added. It was incubated for 30 min at 4° C. then centrifuged at 4° C. for 15 min at 15000 rpm. The pellet is washed with 500 μL of 70% ethanol and centrifuged again for 10 min at 15000 rpm. The pellet is vacuum dried for 15 min and taken up in 50 μL of TE.

2) Preparation of Inserts

Successive EcoR1-NotI Digestions:

2 μg of pTopo DNA plasmid containing the inserts Src-SNAP-CDTM and D-SNAP-CDTM are successively digested by the 2 restriction enzymes framing the insert, namely EcoR1 and NotI. After inactivation of the enzymes for 20 min at 65° C., the DNA is precipitated with ethanol and re-suspended in 20 μL of TE. It was then stored at −20° C.

Purification of Inserts in a Low Melting Agarose Gel (EUROBIO®):

The insert fragments are extracted on 2% low melting agarose gel and column purified using the Nucleospin kit (Nucleospin Extract II® Kit, MACHEREY-NAGEL), The final volume is 50 μL.

3) Ligation 35 ng of dephosphorylated vector is mixed with the insert in a tube in an insert/vector ratio of approximately 3/1 (molecule to molecule). The following are added: 1 μL of 10× ligase buffer, sterile water (qsp 10 μL) and 1 U of T4 DNA ligase (Biolabs®). A negative control is produced by replacing the volume of insert by the same volume of TE1X. The mixtures are incubated overnight at ambient temperature.

4) Transformation of DH5α Bacteria

This transformation is based on a thermal shock. 200 μL of DH5α bacteria is added to the ligation product; 30 min in ice; 2 min at 42° C.; 5 min in ice; addition of 800 μL of LB medium; incubation for 1 h at 37° C. with agitation; seeding 100 μL onto LB/agar/ampicillin dish (50 μg/mL) and incubation for 16 h in an oven at 37° C.

5) Verification of the Presence of the Insert and Viewing on Agarose Gel

Midipreparations and a verification by EcoRI-NotI digestion are carried out in order to select good clones and a stock of plasmid DNA is prepared for the transfection and protein expression step.

IV. Expression of Chimeric Proteins and Targeting to Exosomes

1) Cell Culture

HEK 293T eukaryotic cells (Human Embryonic Kidney) are cultivated in flasks in DMEM medium (Dulbecco's modified eagle's medium), containing 10% foetal calf serum (FCS) and gentamycin in a concentration of 20 μg/mL, at 37° C. in 5% $CO_2$.

2) Transfection $0.5 \times 10^6$ HEK 293T cells per well in 4 mL of DMEM+ 10% FCS without antibiotic are seeded into 6-well plates. After 24 h of culture at 37° C. in 5% $CO_2$, the cells were 90% confluent and are transfected by means of a complex formed between 1 μg of the plasmid of interest and 2 μL of JetPEI (PolyPlus®) in 500 μL of medium; the DNA is internalized by endocytosis. After 6 h of incubation, the medium is replaced by 10% DMEM in FCS free of exosomes contained in the serum (eliminated by ultracentrifuging at 42000 rpm for 18 h (Ti 45 rotor, Beckman). 48 h post-transfection, the supernatant is taken up to recover the exosomes produced and the cells are lysed to obtain the cellular proteins.

3) Preparation of Exosomes

Once the cellular medium has been recovered, it is centrifuged for 10 min at 1400 rpm to eliminate the cells from the culture medium. The supernatant is centrifuged for 10 min at 10000 rpm at 4° C. in order to eliminate cellular debris. The supernatant is recovered and a cushion of TNE with 20% sucrose is poured into the bottom of the tube and ultracentrifuged at 42000 rpm in a Ti50 rotor (Beckman) for 2 h at 4° C. The pellet of pure exosomes is then taken up in 100 μL of PBS.

4) Extraction of Proteins

The cells are washed with PBS at 4° C., then lysed with RIPA buffer (TNE 1×, NP40 0.5%, aprotinin 20 μg/mL, leupeptin 20 μM, sterile $H_2O$, PMSF 0.2 mM). The lysate is centrifuged for 20 min at 14 000 rpm at 4° C. and the supernatant is recovered.

The proteins of the cellular extracts and of the exosomes are dosed using Bradford's method by means of a NanoDrop spectrophotometer and a BSA calibration series (0-200 μg/mL).

5) SDS-PAGE Electrophoresis and Western Blot:

The samples (20 μg for the cellular protein extracts and 2 μg for the exosomal lysates) are separated on 10% polyacrylamide gel for 1 h30 at 60 mA then transferred onto a PVDF membrane (polyvinylidene difluoride, Immobilon-P, Millipore), which has been activated in a methanol bath, rinsed with water then with TBST (Tris Base 20 mM pH 7.4; NaCl 0.15M; Tween 0.5%), overnight at 50 mA in a cold room. The membrane is then saturated with 5% of milk powder in TBST for 1 h. Next, it is incubated overnight at 4° C. with the primary antibody: anti-rabbit CD™ serum prepared in the laboratory. The membrane is washed 3 times each for 5 min with TBST then incubated for 1 h with the secondary antibody, anti-rabbit IgG coupled to peroxidase (Jackson ImmunoResearch). It is washed again in TBST then deposited onto Whatman paper soaked in a solution of ECL (Enhanced chemiluminescence, Amersham)). Revealing is carried out with a Lumi-imager F1 camera (Roche®).

As can be seen in FIG. 34, the DSC proteins (tracks 2 and 5) and SSC CDTM proteins (tracks 3 and 6) make up approximately 30 kDA and are expressed in the cells (see FIG. 34B). The two proteins, DSC and SSC, are targeted in the exosomes (see FIG. 34A). An examination of the ratios between proteins secreted in the exosomes/proteins produced in the cells shows that targeting of the protein SSC in the exosomes is more effective than that of the protein DSC.

BIBLIOGRAPHY

Alberts B, Bray D, Lewis J, Raff M, Roberts K, Watson J D (1995). "Molecular Biology of the Cell (3rd Ed.)" Garland, N.Y.

Bertrand E, Chartrand P, Schaefer M, Shenoy S M, Singer R H, Long R M. (1998). "Localization of ASH1 mRNA particles in living yeast." Mol Cell. Vol. 2 (4), 437-445.

Cann A J, Churcher M J, Boyd M, O'Brien W, Zhao J Q, Zack J, Chen I S (1992). "The region of the envelope gene of human immunodeficiency virus type 1 responsible for determination of cell tropism." J Virol. 1992; 66(1):305-9.

Chaput N, Taïeb J, Schanz N, André F, Angevin E, Zitvogel L. (2004). "Exosomes-based immunotherapy." Cancer Immunol Immunother; 53:234-239.

Colino, J. et Snapper C. M. (2006). Journal of Immunology, 177:37576

De Gassart A, Geminard C, Hoekstra D, Vidal M. (2004). "Exosome secretion the art of reutilizing nonrecycled proteins." Traffic.; 5:896-903.

De Gassart A, Trentin B, Martin M, Hocquellet A, Bette-Bobillo P, Mamoun R, Vidal M. (2009) "Exosomal sorting of the cytoplasmic domain of bovine leukemia virus TM Env protein." Cell Biol Int. 2009 (1):36-48. Epub 2008 Oct. 22.

Delamarre L, Rosenberg A R, Pique C, Pham D, Callebaut I, Dokhelar M C. (1996). "The HTLV-I envelope glycoproteins: structure and functions." J Acquir Immune Defic Syndr Hum Retrovirol; 13 Suppl 1:S85-91.

Delcayre, A., et al. 2005, Blood Cells Mol Dis 35:158; Thery C. et al., (2002); Nature Immunology 3:1156.

Delcayre A, Le Pecq J B. (2006) "Exosomes as novel therapeutic nanodevices." Curr Op in Mol Ther.; 8:1464-1471.

Gould S J, Booth A, Hildret J E. (2003) "The Trojan exosome hypothesis," Proc Natl Acad Sci USA.; 100:10592-10597.

Herbein G, Coaquette A, Perez-Bercoff D, Pancino G. (2002) "Macrophage activation and HIV infection: can the trojan horse turn into a fortress?" Curr Mol. Med.; 2:723-738.

Hurley J H. (2006). "Membrane binding domains", Biochim Biophys Acta. 2006 August; 1761(8):805-11. Epub 2006 Mar. 24. Review.

Keppler A, Gendreizig S, Gronemeyer T, Pick H, Vogel H, Johnsson K. (2002). "A general method for the covalent labeling of fusion proteins with small molecules in vivo". Nat Biotechnol. 2003 January; 21(1):86-89, Epub 2002 Dec. 9.

Keppler A, Pick H, Arrivoli C, Vogel H, Johnsson K. (2004). "Labeling of fusion proteins with synthetic fluorophores in live cells". Proc Natl Acad Sci USA. 2004 Jul. 6; 101(27):9955-9. Epub 2004 Jun. 28.

Levine A J. (1992). "Viruses" (Scientific American Library, No. 37). W. H. Freeman/Scientific American Library Pornillos O, Garrus J, Sundquist W I. (2002). "Mechanism of enveloped RNA virus budding," Trends Cell Biol. 2; 12:569-579.

Raposo G, Moore M, Innes D, Leijenderkker R, Leigh-Brown A, Benaroch P, Geuze H. (2002). "Human macrophage accumulate HIV-1 particles in MHC II compartments." Traffic.; 3:718-729.

Resh M D. (1994). "Myristylation and palmitylation of Src family members: the fats of the matter," Cell. 1994 Feb. 11; 76(3):411-3.

Sloane J A, et al. (2005). "Marked structural and functional heterogeneity in CxCR4: Separation of HIV-1 and SDF-1alpha responses". Immunology and Cell Biology; 83:129-143.

Straub O C, Levy D. (1999). "Bovine immunodeficiency virus and analogies with human immunodeficiency virus." Leukemia; 13 Suppl 1:S106-9.

Zitvogel L, Regnault A, Lozier A, Wolfers J, Tenza D, Raposo G, Amigorena S. (1998). "Dendritic cell-derived exosomes elicit potent antitumour immune responses in vivo." Nat. Med.; 4:594-600.

SEQUENCE LISTING

```
<160> NUMBER OF SEQ ID NOS: 131

<210> SEQ ID NO 1
<211> LENGTH: 81
<212> TYPE: DNA
<213> ORGANISM: Mus musculus
<220> FEATURE:
<221> NAME/KEY: CDS
<222> LOCATION: (1)..(81)
<220> FEATURE:
```

```
<221> NAME/KEY: misc_feature
<222> LOCATION: (1)..(81)
<223> OTHER INFORMATION: Signal peptide for importation of the CD8 alpha
      protein into the endoplasmic reticulum

<400> SEQUENCE: 1 atg gcc tca ccg ttg acc cgc ttt ctg tcg ctg aac ctg ctg ctg ctg         48
Met Ala Ser Pro Leu Thr Arg Phe Leu Ser Leu Asn Leu Leu Leu Leu
1               5                   10                  15 ggt gag tcg att atc ctg ggg agt gga gaa gct                             81
Gly Glu Ser Ile Ile Leu Gly Ser Gly Glu Ala
            20                  25

<210> SEQ ID NO 2
<211> LENGTH: 27
<212> TYPE: PRT
<213> ORGANISM: Mus musculus

<400> SEQUENCE: 2

Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala
            20                  25

<210> SEQ ID NO 3
<211> LENGTH: 69
<212> TYPE: DNA
<213> ORGANISM: Bovine leukemia virus
<220> FEATURE:
<221> NAME/KEY: misc_feature
<222> LOCATION: (1)..(69)
<223> OTHER INFORMATION: Transmembrane domain of TM protein of BLV (wild
      type sequence)
<220> FEATURE:
<221> NAME/KEY: CDS
<222> LOCATION: (1)..(69)

<400> SEQUENCE: 3 ctc att cat tct gtt cta agc cta ttc cta tta gcc ctt ttt tgt ctc         48
Leu Ile His Ser Val Leu Ser Leu Phe Leu Leu Ala Leu Phe Leu Leu
1               5                   10                  15 ttc ttg gcc ccc tgc ctg ata                                             69
Phe Leu Ala Pro Cys Leu Ile
            20

<210> SEQ ID NO 4
<211> LENGTH: 23
<212> TYPE: PRT
<213> ORGANISM: Bovine leukemia virus

<400> SEQUENCE: 4

Leu Ile His Ser Val Leu Ser Leu Phe Leu Leu Ala Leu Phe Leu Leu
1               5                   10                  15

Phe Leu Ala Pro Cys Leu Ile
            20

<210> SEQ ID NO 5
<211> LENGTH: 177
<212> TYPE: DNA
<213> ORGANISM: Bovine leukemia virus
<220> FEATURE:
<221> NAME/KEY: misc_feature
<222> LOCATION: (1)..(177)
<223> OTHER INFORMATION: Wild type cytoplasmic domain (CD) of TM protein
<220> FEATURE:
<221> NAME/KEY: CDS
<222> LOCATION: (1)..(177)
```

<220> FEATURE:
<221> NAME/KEY: misc_feature
<222> LOCATION: (42)..(43)
<223> OTHER INFORMATION: n = t or a

<400> SEQUENCE: 5

```
aaa tgc ttg acc tct cgc ctt tta aaa ctc ctc cgg cag gcn ccc cac      48
Lys Cys Leu Thr Ser Arg Leu Leu Lys Leu Leu Arg Gln Ala Pro His
1               5                   10                  15 ttc cct gaa atc tcc ttc ccc cct aaa ccc gat tct gat tat cag gcc      96
Phe Pro Glu Ile Ser Phe Pro Pro Lys Pro Asp Ser Asp Tyr Gln Ala
            20                  25                  30 ttg cta cca tcc gcg cca gag atc tac tct cac ctc tcc ccc acc aaa     144
Leu Leu Pro Ser Ala Pro Glu Ile Tyr Ser His Leu Ser Pro Thr Lys
        35                  40                  45 ccc gat tac atc aac ctt cga ccc tgc ccc tag                         177
Pro Asp Tyr Ile Asn Leu Arg Pro Cys Pro
    50                  55
```

<210> SEQ ID NO 6
<211> LENGTH: 58
<212> TYPE: PRT
<213> ORGANISM: Bovine leukemia virus

<400> SEQUENCE: 6

```
Lys Cys Leu Thr Ser Arg Leu Leu Lys Leu Leu Arg Gln Ala Pro His
1               5                   10                  15

Phe Pro Glu Ile Ser Phe Pro Pro Lys Pro Asp Ser Asp Tyr Gln Ala
            20                  25                  30

Leu Leu Pro Ser Ala Pro Glu Ile Tyr Ser His Leu Ser Pro Thr Lys
        35                  40                  45

Pro Asp Tyr Ile Asn Leu Arg Pro Cys Pro
    50                  55
```

<210> SEQ ID NO 7
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(135)
<223> OTHER INFORMATION: Mutated derivative of CD of the TM protein of
      bovine leukemia virus (BLV): deletion of the 13 N-terminal
      residues
<220> FEATURE:
<221> NAME/KEY: CDS
<222> LOCATION: (1)..(135)

<400> SEQUENCE: 7

```
gca ccc cac ttc cct gaa atc tcc ttc ccc cct aaa ccc gat tct gat      48
Ala Pro His Phe Pro Glu Ile Ser Phe Pro Pro Lys Pro Asp Ser Asp
1               5                   10                  15 tat cag gcc ttg cta cca tcc gcg cca gag atc tac tct cac ctc tcc      96
Tyr Gln Ala Leu Leu Pro Ser Ala Pro Glu Ile Tyr Ser His Leu Ser
            20                  25                  30 ccc acc aaa ccc gat tac atc aac ctt cga ccc tgc ccc                 135
Pro Thr Lys Pro Asp Tyr Ile Asn Leu Arg Pro Cys Pro
        35                  40                  45
```

<210> SEQ ID NO 8
<211> LENGTH: 45
<212> TYPE: PRT
<213> ORGANISM: Artificial Sequence

```
<220> FEATURE:
<223> OTHER INFORMATION: Synthetic Construct

<400> SEQUENCE: 8

Ala Pro His Phe Pro Glu Ile Ser Phe Pro Pro Lys Pro Asp Ser Asp
1               5                   10                  15

Tyr Gln Ala Leu Leu Pro Ser Ala Pro Glu Ile Tyr Ser His Leu Ser
            20                  25                  30

Pro Thr Lys Pro Asp Tyr Ile Asn Leu Arg Pro Cys Pro
        35                  40                  45

<210> SEQ ID NO 9
<211> LENGTH: 174
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(174)
<223> OTHER INFORMATION: Mutated derivative of CD of the TM protein of
      BLV: substitution of residue C in motif PCT with a residue A
<220> FEATURE:
<221> NAME/KEY: CDS
<222> LOCATION: (1)..(174)

<400> SEQUENCE: 9 aaa tgc ttg acc tct cgc ctt tta aaa ctc ctc cgg cag gca ccc cac    48
Lys Cys Leu Thr Ser Arg Leu Leu Lys Leu Leu Arg Gln Ala Pro His
1               5                   10                  15 ttc cct gaa atc tcc ttc ccc cct aaa ccc gat tct gat tat cag gcc    96
Phe Pro Glu Ile Ser Phe Pro Pro Lys Pro Asp Ser Asp Tyr Gln Ala
            20                  25                  30 ttg cta cca tcc gcg cca gag atc tac tct cac ctc tcc ccc acc aaa   144
Leu Leu Pro Ser Ala Pro Glu Ile Tyr Ser His Leu Ser Pro Thr Lys
        35                  40                  45 ccc gat tac atc aac ctt cga ccg gcg ccc                           174
Pro Asp Tyr Ile Asn Leu Arg Pro Ala Pro
50                  55

<210> SEQ ID NO 10
<211> LENGTH: 58
<212> TYPE: PRT
<213> ORGANISM: Artificial Sequence
<220> FEATURE:
<223> OTHER INFORMATION: Synthetic Construct

<400> SEQUENCE: 10

Lys Cys Leu Thr Ser Arg Leu Leu Lys Leu Leu Arg Gln Ala Pro His
1               5                   10                  15

Phe Pro Glu Ile Ser Phe Pro Pro Lys Pro Asp Ser Asp Tyr Gln Ala
            20                  25                  30

Leu Leu Pro Ser Ala Pro Glu Ile Tyr Ser His Leu Ser Pro Thr Lys
        35                  40                  45

Pro Asp Tyr Ile Asn Leu Arg Pro Ala Pro
50                  55

<210> SEQ ID NO 11
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
```

```
<222> LOCATION: (1)..(135)
<220> FEATURE:
<221> NAME/KEY: misc_feature
<222> LOCATION: (1)..(135)
<223> OTHER INFORMATION: Mutated derivative of CD of the TM protein of
      BLV: deletion of the 13 N-terminal residues and substitution of
      residue C of motif PCP with a residue A

<400> SEQUENCE: 11 gca ccc cac ttc cct gaa atc tcc ttc ccc cct aaa ccc gat tct gat      48
Ala Pro His Phe Pro Glu Ile Ser Phe Pro Pro Lys Pro Asp Ser Asp
1               5                   10                  15 tat cag gcc ttg cta cca tcc gcg cca gag atc tac tct cac ctc tcc      96
Tyr Gln Ala Leu Leu Pro Ser Ala Pro Glu Ile Tyr Ser His Leu Ser
                20                  25                  30 ccc acc aaa ccc gat tac atc aac ctt cga ccg gcg ccc                  135
Pro Thr Lys Pro Asp Tyr Ile Asn Leu Arg Pro Ala Pro
            35                  40                  45

<210> SEQ ID NO 12
<211> LENGTH: 45
<212> TYPE: PRT
<213> ORGANISM: Artificial Sequence
<220> FEATURE:
<223> OTHER INFORMATION: Synthetic Construct

<400> SEQUENCE: 12

Ala Pro His Phe Pro Glu Ile Ser Phe Pro Pro Lys Pro Asp Ser Asp
1               5                   10                  15

Tyr Gln Ala Leu Leu Pro Ser Ala Pro Glu Ile Tyr Ser His Leu Ser
                20                  25                  30

Pro Thr Lys Pro Asp Tyr Ile Asn Leu Arg Pro Ala Pro
            35                  40                  45

<210> SEQ ID NO 13
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of CD of the TM protein of
      BLV: deletion of the 13 N-terminal residues and substitution of
      the 2 residues P of the 1st motif PxxP

<400> SEQUENCE: 13 gca gcc cac ttc gct gag ata tcc ttc ccc cct aaa ccc gat tct gat      48
Ala Ala His Phe Ala Glu Ile Ser Phe Pro Pro Lys Pro Asp Ser Asp
1               5                   10                  15 tat cag gcc ttg cta cca tcc gcg cca gag atc tac tct cac ctc tcc      96
Tyr Gln Ala Leu Leu Pro Ser Ala Pro Glu Ile Tyr Ser His Leu Ser
                20                  25                  30 ccc acc aaa ccc gat tac atc aac ctt cga ccc tgc ccc                  135
Pro Thr Lys Pro Asp Tyr Ile Asn Leu Arg Pro Cys Pro
            35                  40                  45

<210> SEQ ID NO 14
<211> LENGTH: 45
<212> TYPE: PRT
<213> ORGANISM: Artificial Sequence
<220> FEATURE:
<223> OTHER INFORMATION: Synthetic Construct
```

<400> SEQUENCE: 14

Ala Ala His Phe Ala Glu Ile Ser Phe Pro Pro Lys Pro Asp Ser Asp
1               5                   10                  15

Tyr Gln Ala Leu Leu Pro Ser Ala Pro Glu Ile Tyr Ser His Leu Ser
            20                  25                  30

Pro Thr Lys Pro Asp Tyr Ile Asn Leu Arg Pro Cys Pro
        35                  40                  45

<210> SEQ ID NO 15
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of CD of the TM protein of
      BLV: deletion of the 13 N-terminal residues and substitution of
      the 2 residues P of the 2nd motif PxxP

<400> SEQUENCE: 15 gca ccc cac ttc cct gag ata tcc ttc gcc cct aaa gcc gat tct gat       48
Ala Pro His Phe Pro Glu Ile Ser Phe Ala Pro Lys Ala Asp Ser Asp
1               5                   10                  15 tat cag gcc ttg cta cca tcc gcg cca gag atc tac tct cac ctc tcc       96
Tyr Gln Ala Leu Leu Pro Ser Ala Pro Glu Ile Tyr Ser His Leu Ser
            20                  25                  30 ccc acc aaa ccc gat tac atc aac ctt cga ccc tgc ccc                  135
Pro Thr Lys Pro Asp Tyr Ile Asn Leu Arg Pro Cys Pro
        35                  40                  45

<210> SEQ ID NO 16
<211> LENGTH: 45
<212> TYPE: PRT
<213> ORGANISM: Artificial Sequence
<220> FEATURE:
<223> OTHER INFORMATION: Synthetic Construct

<400> SEQUENCE: 16

Ala Pro His Phe Pro Glu Ile Ser Phe Ala Pro Lys Ala Asp Ser Asp
1               5                   10                  15

Tyr Gln Ala Leu Leu Pro Ser Ala Pro Glu Ile Tyr Ser His Leu Ser
            20                  25                  30

Pro Thr Lys Pro Asp Tyr Ile Asn Leu Arg Pro Cys Pro
        35                  40                  45

<210> SEQ ID NO 17
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of CD of the TM protein of
      BLV: deletion of the 13 N-terminal residues and substitution of
      the 2 proline residues of the 3rd motif PxxP

```
<400> SEQUENCE: 17 gca ccc cac ttc cct gaa atc tcc ttc ccc cct aaa ccc gat tct gat    48
Ala Pro His Phe Pro Glu Ile Ser Phe Pro Pro Lys Pro Asp Ser Asp
1               5                   10                  15 tat cag gcc ttg cta gca tcg gcg gca gag att tac tct cac ctc tcc    96
Tyr Gln Ala Leu Leu Ala Ser Ala Ala Glu Ile Tyr Ser His Leu Ser
                20                  25                  30 ccc acc aaa ccc gat tac atc aac ctt cga ccc tgc ccc               135
Pro Thr Lys Pro Asp Tyr Ile Asn Leu Arg Pro Cys Pro
        35                  40                  45

<210> SEQ ID NO 18
<211> LENGTH: 45
<212> TYPE: PRT
<213> ORGANISM: Artificial Sequence
<220> FEATURE:
<223> OTHER INFORMATION: Synthetic Construct

<400> SEQUENCE: 18

Ala Pro His Phe Pro Glu Ile Ser Phe Pro Pro Lys Pro Asp Ser Asp
1               5                   10                  15

Tyr Gln Ala Leu Leu Ala Ser Ala Ala Glu Ile Tyr Ser His Leu Ser
                20                  25                  30

Pro Thr Lys Pro Asp Tyr Ile Asn Leu Arg Pro Cys Pro
        35                  40                  45

<210> SEQ ID NO 19
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of CD of the TM protein of
      BLV: deletion of the 13 N-terminal residues and substitution of
      the 1st residue P of the 4th motif PxxP

<400> SEQUENCE: 19 gca ccc cac ttc cct gaa atc tcc ttc ccc cct aaa ccc gat tct gat    48
Ala Pro His Phe Pro Glu Ile Ser Phe Pro Pro Lys Pro Asp Ser Asp
1               5                   10                  15 tat cag gcc ttg cta cca tcc gcg cca gag ata tac tct cac ctc tcc    96
Tyr Gln Ala Leu Leu Pro Ser Ala Pro Glu Ile Tyr Ser His Leu Ser
                20                  25                  30 gcc acc aaa ccc gat tac atc aac ctt cga ccc tgc ccc               135
Ala Thr Lys Pro Asp Tyr Ile Asn Leu Arg Pro Cys Pro
        35                  40                  45

<210> SEQ ID NO 20
<211> LENGTH: 45
<212> TYPE: PRT
<213> ORGANISM: Artificial Sequence
<220> FEATURE:
<223> OTHER INFORMATION: Synthetic Construct

<400> SEQUENCE: 20

Ala Pro His Phe Pro Glu Ile Ser Phe Pro Pro Lys Pro Asp Ser Asp
1               5                   10                  15

Tyr Gln Ala Leu Leu Pro Ser Ala Pro Glu Ile Tyr Ser His Leu Ser
                20                  25                  30
```

```
Ala Thr Lys Pro Asp Tyr Ile Asn Leu Arg Pro Cys Pro
        35                  40                  45
```

<210> SEQ ID NO 21
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(135)
<223> OTHER INFORMATION: Mutated derivative of CD of the TM protein of
      BLV: deletion of the 13 N-terminal residues and substitution of
      the 2 residues P of the 4th motif PxxP
<220> FEATURE:
<221> NAME/KEY: misc_feature
<222> LOCATION: (1)..(135)
<223> OTHER INFORMATION: Mutated derivative of CD of the TM protein of
      BLV: deletion of the 13 N-terminal residues and substitution of
      the C residue of the 4th motif of the motif PCP with a residue A
      of the 4th motif PxxP
<220> FEATURE:
<221> NAME/KEY: CDS
<222> LOCATION: (1)..(135)

<400> SEQUENCE: 21

```
gca ccc cac ttc cct gaa atc tcc ttc ccc cct aaa ccc gat tct gat      48
Ala Pro His Phe Pro Glu Ile Ser Phe Pro Pro Lys Pro Asp Ser Asp
1               5                   10                  15 tat cag gcc ttg cta cca tcc gcg cca gag ata tac tct cac ctc tcc      96
Tyr Gln Ala Leu Leu Pro Ser Ala Pro Glu Ile Tyr Ser His Leu Ser
            20                  25                  30 gcc acc aaa gcc gat tac atc aac ctt cga ccc tgc ccc                  135
Ala Thr Lys Ala Asp Tyr Ile Asn Leu Arg Pro Cys Pro
        35                  40                  45
```

<210> SEQ ID NO 22
<211> LENGTH: 45
<212> TYPE: PRT
<213> ORGANISM: Artificial Sequence
<220> FEATURE:
<223> OTHER INFORMATION: Synthetic Construct

<400> SEQUENCE: 22

```
Ala Pro His Phe Pro Glu Ile Ser Phe Pro Pro Lys Pro Asp Ser Asp
1               5                   10                  15

Tyr Gln Ala Leu Leu Pro Ser Ala Pro Glu Ile Tyr Ser His Leu Ser
            20                  25                  30

Ala Thr Lys Ala Asp Tyr Ile Asn Leu Arg Pro Cys Pro
        35                  40                  45
```

<210> SEQ ID NO 23
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of CD of the TM protein of
      BLV: deletion of the 13 N-terminal residues and substitution of
      the residue Y of the 1st motif YxxL

<400> SEQUENCE: 23

```
gca ccc cac ttc cct gaa atc tcc ttc ccc cct aaa ccc gat tct gat      48
Ala Pro His Phe Pro Glu Ile Ser Phe Pro Pro Lys Pro Asp Ser Asp
1               5                   10                  15 gcg cag gca ttg cta cca tcg gcg cca gag atc tac tct cac ctc tcc      96
Ala Gln Ala Leu Leu Pro Ser Ala Pro Glu Ile Tyr Ser His Leu Ser
            20                  25                  30 ccc acc aaa ccc gat tac atc aac ctt cga ccc tgc ccc                 135
Pro Thr Lys Pro Asp Tyr Ile Asn Leu Arg Pro Cys Pro
        35                  40                  45

<210> SEQ ID NO 24
<211> LENGTH: 45
<212> TYPE: PRT
<213> ORGANISM: Artificial Sequence
<220> FEATURE:
<223> OTHER INFORMATION: Synthetic Construct

<400> SEQUENCE: 24

Ala Pro His Phe Pro Glu Ile Ser Phe Pro Pro Lys Pro Asp Ser Asp
1               5                   10                  15

Ala Gln Ala Leu Leu Pro Ser Ala Pro Glu Ile Tyr Ser His Leu Ser
            20                  25                  30

Pro Thr Lys Pro Asp Tyr Ile Asn Leu Arg Pro Cys Pro
        35                  40                  45

<210> SEQ ID NO 25
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of CD of the TM protein of
      BLV: deletion of the 13 N-terminal residues and substitution of
      the residue Y of the 2nd motif YxxL

<400> SEQUENCE: 25 gca ccc cac ttc cct gaa atc tcc ttc ccc cct aaa ccc gat tct gat      48
Ala Pro His Phe Pro Glu Ile Ser Phe Pro Pro Lys Pro Asp Ser Asp
1               5                   10                  15 tat cag gcc ttg cta cca tcg gcg cca gag atc gca tct cac ctc tcc      96
Tyr Gln Ala Leu Leu Pro Ser Ala Pro Glu Ile Ala Ser His Leu Ser
            20                  25                  30 ccc acc aaa ccc gat tac atc aac ctt cga ccc tgc ccc                 135
Pro Thr Lys Pro Asp Tyr Ile Asn Leu Arg Pro Cys Pro
        35                  40                  45

<210> SEQ ID NO 26
<211> LENGTH: 45
<212> TYPE: PRT
<213> ORGANISM: Artificial Sequence
<220> FEATURE:
<223> OTHER INFORMATION: Synthetic Construct

<400> SEQUENCE: 26

Ala Pro His Phe Pro Glu Ile Ser Phe Pro Pro Lys Pro Asp Ser Asp
1               5                   10                  15

Tyr Gln Ala Leu Leu Pro Ser Ala Pro Glu Ile Ala Ser His Leu Ser
            20                  25                  30
```

```
Pro Thr Lys Pro Asp Tyr Ile Asn Leu Arg Pro Cys Pro
        35              40              45

<210> SEQ ID NO 27
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of CD of the TM protein of
      BLV: substitution of the residue Y of the 3rd motif YxxL

<400> SEQUENCE: 27 gca ccc cac ttc cct gaa atc tcc ttc ccc cct aaa ccc gat tct gat      48
Ala Pro His Phe Pro Glu Ile Ser Phe Pro Pro Lys Pro Asp Ser Asp
1               5                   10                  15 tat cag gcc ttg cta cca tcc gcg cca gag atc tac tct cac ctc tcc      96
Tyr Gln Ala Leu Leu Pro Ser Ala Pro Glu Ile Tyr Ser His Leu Ser
            20                  25                  30 ccc acc aaa ccc gat gcc atc aac ctt agg ccc tgc ccc                  135
Pro Thr Lys Pro Asp Ala Ile Asn Leu Arg Pro Cys Pro
        35              40              45

<210> SEQ ID NO 28
<211> LENGTH: 45
<212> TYPE: PRT
<213> ORGANISM: Artificial Sequence
<220> FEATURE:
<223> OTHER INFORMATION: Synthetic Construct

<400> SEQUENCE: 28

Ala Pro His Phe Pro Glu Ile Ser Phe Pro Pro Lys Pro Asp Ser Asp
1               5                   10                  15

Tyr Gln Ala Leu Leu Pro Ser Ala Pro Glu Ile Tyr Ser His Leu Ser
            20                  25                  30

Pro Thr Lys Pro Asp Ala Ile Asn Leu Arg Pro Cys Pro
        35              40              45

<210> SEQ ID NO 29
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of CD of the TM protein of
      BLV: substitution of the 13 N-terminal residues Y and substitution
      of the residue S before the 1st motif YxxL
<220> FEATURE:
<221> NAME/KEY: misc_feature
<222> LOCATION: (1)..(135)
<223> OTHER INFORMATION: Mutated derivative of CD of the TM protein of
      BLV: substitution of the 13 N-terminal residues and substitution
      of the residue S before the 1st motif YxxL

<400> SEQUENCE: 29 gca ccc cac ttc cct gaa atc tcc ttc ccc cct aaa ccc gat gct gat      48
Ala Pro His Phe Pro Glu Ile Ser Phe Pro Pro Lys Pro Asp Ala Asp
```

```
                1               5                   10                  15
tat cag gcg ttg cta cca tcc gcg cca gag atc tac tct cac ctc tcc        96
Tyr Gln Ala Leu Leu Pro Ser Ala Pro Glu Ile Tyr Ser His Leu Ser
                20                  25                  30 ccc acc aaa ccc gat tac atc aac ctt cga ccc tgc ccc                    135
Pro Thr Lys Pro Asp Tyr Ile Asn Leu Arg Pro Cys Pro
        35                  40                  45
```

<210> SEQ ID NO 30
<211> LENGTH: 45
<212> TYPE: PRT
<213> ORGANISM: Artificial Sequence
<220> FEATURE:
<223> OTHER INFORMATION: Synthetic Construct

<400> SEQUENCE: 30

```
Ala Pro His Phe Pro Glu Ile Ser Phe Pro Pro Lys Pro Asp Ala Asp
1               5                   10                  15

Tyr Gln Ala Leu Leu Pro Ser Ala Pro Glu Ile Tyr Ser His Leu Ser
                20                  25                  30

Pro Thr Lys Pro Asp Tyr Ile Asn Leu Arg Pro Cys Pro
        35                  40                  45
```

<210> SEQ ID NO 31
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of CD of the TM protein of
      BLV: deletion of the 13 N-terminal residues and substitution of
      the residue E before the 2nd motif YxxL

<400> SEQUENCE: 31

```
gca ccc cac ttc cct gaa atc tcc ttc ccc cct aaa ccc gat tct gat        48
Ala Pro His Phe Pro Glu Ile Ser Phe Pro Pro Lys Pro Asp Ser Asp
1               5                   10                  15 tat cag gcc ttg cta cca tcc gcg cca gcg atc tac tct cac ctc tcc        96
Tyr Gln Ala Leu Leu Pro Ser Ala Pro Ala Ile Tyr Ser His Leu Ser
                20                  25                  30 ccc acc aaa ccc gat tac atc aac ctt cga ccc tgc ccc                    135
Pro Thr Lys Pro Asp Tyr Ile Asn Leu Arg Pro Cys Pro
        35                  40                  45
```

<210> SEQ ID NO 32
<211> LENGTH: 45
<212> TYPE: PRT
<213> ORGANISM: Artificial Sequence
<220> FEATURE:
<223> OTHER INFORMATION: Synthetic Construct

<400> SEQUENCE: 32

```
Ala Pro His Phe Pro Glu Ile Ser Phe Pro Pro Lys Pro Asp Ser Asp
1               5                   10                  15

Tyr Gln Ala Leu Leu Pro Ser Ala Pro Ala Ile Tyr Ser His Leu Ser
                20                  25                  30

Pro Thr Lys Pro Asp Tyr Ile Asn Leu Arg Pro Cys Pro
        35                  40                  45
```

<210> SEQ ID NO 33
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of CD domain of the TM
      protein of BLV: deletion of the 13 N-terminal residues and
      substitution of the residue D before the 3rd motif YxxL

<400> SEQUENCE: 33

```
gca ccc cac ttc cct gaa atc tcc ttc ccc cct aaa ccc gat tct gat      48
Ala Pro His Phe Pro Glu Ile Ser Phe Pro Pro Lys Pro Asp Ser Asp
1               5                   10                  15 tat cag gcc ttg cta cca tcc gcg cca gag atc tac tct cac ctc tcc      96
Tyr Gln Ala Leu Leu Pro Ser Ala Pro Glu Ile Tyr Ser His Leu Ser
            20                  25                  30 ccc acc aag ccg gct tac atc aac ctt cga ccc tgc ccc                 135
Pro Thr Lys Pro Ala Tyr Ile Asn Leu Arg Pro Cys Pro
        35                  40                  45
```

<210> SEQ ID NO 34
<211> LENGTH: 45
<212> TYPE: PRT
<213> ORGANISM: Artificial Sequence
<220> FEATURE:
<223> OTHER INFORMATION: Synthetic Construct

<400> SEQUENCE: 34

```
Ala Pro His Phe Pro Glu Ile Ser Phe Pro Pro Lys Pro Asp Ser Asp
1               5                   10                  15

Tyr Gln Ala Leu Leu Pro Ser Ala Pro Glu Ile Tyr Ser His Leu Ser
            20                  25                  30

Pro Thr Lys Pro Ala Tyr Ile Asn Leu Arg Pro Cys Pro
        35                  40                  45
```

<210> SEQ ID NO 35
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(18)
<220> FEATURE:
<221> NAME/KEY: misc_feature
<222> LOCATION: (1)..(18)
<223> OTHER INFORMATION: Mutated derivative of CD domain of the TM
      protein of BLV: deletion of the 13 N-terminal residues and of the
      39 C-terminal residues

<400> SEQUENCE: 35

```
gca ccc cac ttc cct gaa                                              18
Ala Pro His Phe Pro Glu
1               5
```

<210> SEQ ID NO 36
<211> LENGTH: 6
<212> TYPE: PRT
<213> ORGANISM: Artificial Sequence
<220> FEATURE:

<223> OTHER INFORMATION: Synthetic Construct

<400> SEQUENCE: 36

Ala Pro His Phe Pro Glu
1               5

<210> SEQ ID NO 37
<211> LENGTH: 45
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(45)
<220> FEATURE:
<221> NAME/KEY: misc_feature
<222> LOCATION: (1)..(45)
<223> OTHER INFORMATION: Mutated derivative of CD domain of the TM
      protein of BLV: deletion of the 13 N-terminal residues and of the
      30 C-terminal residues

<400> SEQUENCE: 37 gca ccc cac ttc cct gaa atc tcc ttc ccc cct aaa ccc gat tct       45
Ala Pro His Phe Pro Glu Ile Ser Phe Pro Pro Lys Pro Asp Ser
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic Construct

<400> SEQUENCE: 38

Ala Pro His Phe Pro Glu Ile Ser Phe Pro Pro Lys Pro Asp Ser
1               5                   10                  15

<210> SEQ ID NO 39
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(63)
<220> FEATURE:
<221> NAME/KEY: misc_feature
<222> LOCATION: (1)..(63)
<223> OTHER INFORMATION: Mutated derivative of CD domain of the TM
      protein of BLV: deletion of the 13 N-terminal residues and of the
      24 C-terminal residues

<400> SEQUENCE: 39 gca ccc cac ttc cct gaa atc tcc ttc ccc cct aaa ccc gat tct gat   48
Ala Pro His Phe Pro Glu Ile Ser Phe Pro Pro Lys Pro Asp Ser Asp
1               5                   10                  15 tat cag gcc ttg cta                                                63
Tyr Gln Ala Leu Leu
            20

<210> SEQ ID NO 40
<211> LENGTH: 21
<212> TYPE: PRT
<213> ORGANISM: Artificial Sequence
<220> FEATURE:
<223> OTHER INFORMATION: Synthetic Construct

<400> SEQUENCE: 40

```
Ala Pro His Phe Pro Glu Ile Ser Phe Pro Pro Lys Pro Asp Ser Asp
1               5                   10                  15

Tyr Gln Ala Leu Leu
            20
```

<210> SEQ ID NO 41
<211> LENGTH: 78
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(78)
<220> FEATURE:
<221> NAME/KEY: misc_feature
<222> LOCATION: (1)..(78)
<223> OTHER INFORMATION: Mutated derivative of CD domain of the TM
      protein of BLV: deletion of the 13 N-terminal residues and of the
      19 C-terminal residues

<400> SEQUENCE: 41

```
gca ccc cac ttc cct gaa atc tcc ttc ccc cct aaa ccc gat tct gat      48
Ala Pro His Phe Pro Glu Ile Ser Phe Pro Pro Lys Pro Asp Ser Asp
1               5                   10                  15 tat cag gcc ttg cta cca tcc gcg cca gag                              78
Tyr Gln Ala Leu Leu Pro Ser Ala Pro Glu
            20                  25
```

<210> SEQ ID NO 42
<211> LENGTH: 26
<212> TYPE: PRT
<213> ORGANISM: Artificial Sequence
<220> FEATURE:
<223> OTHER INFORMATION: Synthetic Construct

<400> SEQUENCE: 42

```
Ala Pro His Phe Pro Glu Ile Ser Phe Pro Pro Lys Pro Asp Ser Asp
1               5                   10                  15

Tyr Gln Ala Leu Leu Pro Ser Ala Pro Glu
            20                  25
```

<210> SEQ ID NO 43
<211> LENGTH: 93
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(93)
<220> FEATURE:
<221> NAME/KEY: misc_feature
<222> LOCATION: (1)..(93)
<223> OTHER INFORMATION: Mutated derivative of CD domain of the TM
      protein of BLV: deletion of the 13 N-terminal residues and of the
      14 C-terminal residues

<400> SEQUENCE: 43

```
gca ccc cac ttc cct gaa atc tcc ttc ccc cct aaa ccc gat tct gat      48
Ala Pro His Phe Pro Glu Ile Ser Phe Pro Pro Lys Pro Asp Ser Asp
1               5                   10                  15 tat cag gcc ttg cta cca tcc gcg cca gag atc tac tct cac ctc          93
Tyr Gln Ala Leu Leu Pro Ser Ala Pro Glu Ile Tyr Ser His Leu
            20                  25                  30
```

<210> SEQ ID NO 44

```
<211> LENGTH: 31
<212> TYPE: PRT
<213> ORGANISM: Artificial Sequence
<220> FEATURE:
<223> OTHER INFORMATION: Synthetic Construct

<400> SEQUENCE: 44

Ala Pro His Phe Pro Glu Ile Ser Phe Pro Pro Lys Pro Asp Ser Asp
1               5                   10                  15
Tyr Gln Ala Leu Leu Pro Ser Ala Pro Glu Ile Tyr Ser His Leu
            20                  25                  30

<210> SEQ ID NO 45
<211> LENGTH: 111
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(111)
<220> FEATURE:
<221> NAME/KEY: misc_feature
<222> LOCATION: (1)..(111)
<223> OTHER INFORMATION: Mutated derivative of CD domain of the TM
      protein of BLV: deletion of the 13 N-terminal residues and of the
      8 C-terminal residues

<400> SEQUENCE: 45 gca ccc cac ttc cct gaa atc tcc ttc ccc cct aaa ccc gat tct gat      48
Ala Pro His Phe Pro Glu Ile Ser Phe Pro Pro Lys Pro Asp Ser Asp
1               5                   10                  15 tat cag gcc ttg cta cca tcc gcg cca gag atc tac tct cac ctc tcc      96
Tyr Gln Ala Leu Leu Pro Ser Ala Pro Glu Ile Tyr Ser His Leu Ser
            20                  25                  30 ccc acc aaa ccc gat                                                 111
Pro Thr Lys Pro Asp
        35

<210> SEQ ID NO 46
<211> LENGTH: 37
<212> TYPE: PRT
<213> ORGANISM: Artificial Sequence
<220> FEATURE:
<223> OTHER INFORMATION: Synthetic Construct

<400> SEQUENCE: 46

Ala Pro His Phe Pro Glu Ile Ser Phe Pro Pro Lys Pro Asp Ser Asp
1               5                   10                  15
Tyr Gln Ala Leu Leu Pro Ser Ala Pro Glu Ile Tyr Ser His Leu Ser
            20                  25                  30
Pro Thr Lys Pro Asp
        35

<210> SEQ ID NO 47
<211> LENGTH: 123
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(123)
<220> FEATURE:
<221> NAME/KEY: misc_feature
<222> LOCATION: (1)..(123)
<223> OTHER INFORMATION: Mutated derivative of CD domain of the TM
      protein of BLV: deletion of the 13 N-terminal residues and of the
```

4 C-terminal residues

<400> SEQUENCE: 47 gca ccc cac ttc cct gaa atc tcc ttc ccc cct aaa ccc gat tct gat      48
Ala Pro His Phe Pro Glu Ile Ser Phe Pro Pro Lys Pro Asp Ser Asp
1               5                   10                  15 tat cag gcc ttg cta cca tcc gcg cca gag atc tac tct cac ctc tcc      96
Tyr Gln Ala Leu Leu Pro Ser Ala Pro Glu Ile Tyr Ser His Leu Ser
            20                  25                  30 ccc acc aaa ccc gat tac atc aac ctt                                 123
Pro Thr Lys Pro Asp Tyr Ile Asn Leu
        35                  40

<210> SEQ ID NO 48
<211> LENGTH: 41
<212> TYPE: PRT
<213> ORGANISM: Artificial Sequence
<220> FEATURE:
<223> OTHER INFORMATION: Synthetic Construct

<400> SEQUENCE: 48

Ala Pro His Phe Pro Glu Ile Ser Phe Pro Pro Lys Pro Asp Ser Asp
1               5                   10                  15

Tyr Gln Ala Leu Leu Pro Ser Ala Pro Glu Ile Tyr Ser His Leu Ser
            20                  25                  30

Pro Thr Lys Pro Asp Tyr Ile Asn Leu
        35                  40

<210> SEQ ID NO 49
<211> LENGTH: 25
<212> TYPE: PRT
<213> ORGANISM: Homo sapiens
<220> FEATURE:
<221> NAME/KEY: MISC_FEATURE
<222> LOCATION: (1)..(24)
<223> OTHER INFORMATION: CD4

<400> SEQUENCE: 49

Met Asn Arg Gly Val Pro Phe Arg His Leu Leu Leu Val Leu Gln Leu
1               5                   10                  15

Ala Leu Leu Pro Ala Ala Thr Gln Gly
            20                  25

<210> SEQ ID NO 50
<211> LENGTH: 22
<212> TYPE: PRT
<213> ORGANISM: Mus musculus
<220> FEATURE:
<221> NAME/KEY: MISC_FEATURE
<222> LOCATION: (1)..(22)
<223> OTHER INFORMATION: CD4

<400> SEQUENCE: 50

Met Cys Arg Ala Ile Ser Leu Arg Arg Leu Leu Leu Leu Leu Leu Gln
1               5                   10                  15

Leu Ser Gln Leu Leu Ala
            20

<210> SEQ ID NO 51
<211> LENGTH: 27
<212> TYPE: PRT
<213> ORGANISM: Mus musculus
<220> FEATURE:
<221> NAME/KEY: MISC_FEATURE
<222> LOCATION: (1)..(27)

<223> OTHER INFORMATION: CD8 alpha

<400> SEQUENCE: 51

Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala
            20                  25

<210> SEQ ID NO 52
<211> LENGTH: 25
<212> TYPE: PRT
<213> ORGANISM: Artificial Sequence
<220> FEATURE:
<223> OTHER INFORMATION: bovine CD8 alpha protein

<400> SEQUENCE: 52

Met Ala Ser Leu Leu Thr Ala Leu Ile Leu Pro Leu Ala Leu Leu Leu
1               5                   10                  15

Leu Asp Ala Ala Lys Val Leu Gly Ser
            20                  25

<210> SEQ ID NO 53
<211> LENGTH: 21
<212> TYPE: PRT
<213> ORGANISM: Homo sapiens
<220> FEATURE:
<221> NAME/KEY: MISC_FEATURE
<222> LOCATION: (1)..(21)
<223> OTHER INFORMATION: CD8 alpha

<400> SEQUENCE: 53

Met Ala Leu Pro Val Thr Ala Leu Leu Leu Pro Leu Ala Leu Leu Leu
1               5                   10                  15

His Ala Ala Arg Pro
            20

<210> SEQ ID NO 54
<211> LENGTH: 26
<212> TYPE: PRT
<213> ORGANISM: Rattus norvegicus
<220> FEATURE:
<221> NAME/KEY: MISC_FEATURE
<222> LOCATION: (1)..(26)
<223> OTHER INFORMATION: CD8 alpha

<400> SEQUENCE: 54

Met Ala Leu Pro Val Thr Ala Leu Leu Leu Pro Leu Ala Leu Leu Leu
1               5                   10                  15

His Ala Ala Arg Pro Ser Gln Phe Arg Val
            20                  25

<210> SEQ ID NO 55
<211> LENGTH: 27
<212> TYPE: PRT
<213> ORGANISM: Homo sapiens
<220> FEATURE:
<221> NAME/KEY: MISC_FEATURE
<222> LOCATION: (1)..(27)
<223> OTHER INFORMATION: IL1R1

<400> SEQUENCE: 55

Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu
            20                  25

<210> SEQ ID NO 56
<211> LENGTH: 24
<212> TYPE: PRT
<213> ORGANISM: Homo sapiens
<220> FEATURE:
<221> NAME/KEY: MISC_FEATURE
<222> LOCATION: (1)..(24)
<223> OTHER INFORMATION: EGFR 1, HER 1

<400> SEQUENCE: 56

Met Arg Pro Ser Gly Thr Ala Gly Ala Ala Leu Leu Ala Leu Leu Ala
1               5                   10                  15

Ala Leu Cys Pro Ala Ser Arg Ala
            20

<210> SEQ ID NO 57
<211> LENGTH: 22
<212> TYPE: PRT
<213> ORGANISM: Homo sapiens
<220> FEATURE:
<221> NAME/KEY: MISC_FEATURE
<222> LOCATION: (1)..(22)
<223> OTHER INFORMATION: HER 2

<400> SEQUENCE: 57

Met Glu Leu Ala Ala Leu Cys Arg Trp Gly Leu Leu Leu Ala Leu Leu
1               5                   10                  15

Pro Pro Gly Ala Ala Ser
            20

<210> SEQ ID NO 58
<211> LENGTH: 19
<212> TYPE: PRT
<213> ORGANISM: Homo sapiens
<220> FEATURE:
<221> NAME/KEY: MISC_FEATURE
<222> LOCATION: (1)..(19)
<223> OTHER INFORMATION: HER 3

<400> SEQUENCE: 58

Met Arg Ala Asn Asp Ala Leu Gln Val Leu Gly Leu Leu Phe Ser Leu
1               5                   10                  15

Ala Arg Gly

<210> SEQ ID NO 59
<211> LENGTH: 25
<212> TYPE: PRT
<213> ORGANISM: Homo sapiens
<220> FEATURE:
<221> NAME/KEY: MISC_FEATURE
<222> LOCATION: (1)..(25)
<223> OTHER INFORMATION: HER 4

<400> SEQUENCE: 59

Met Lys Pro Ala Thr Gly Leu Trp Val Trp Val Ser Leu Leu Val Ala
1               5                   10                  15

Ala Gly Thr Val Gln Pro Ser Asp Ser
            20                  25

<210> SEQ ID NO 60
<211> LENGTH: 20
<212> TYPE: PRT
<213> ORGANISM: Mus musculus
<220> FEATURE:
<221> NAME/KEY: MISC_FEATURE

```
<222> LOCATION: (1)..(20)
<223> OTHER INFORMATION: IL-2

<400> SEQUENCE: 60

Met Tyr Ser Met Gln Leu Ala Ser Cys Val Thr Leu Thr Leu Val Leu
1               5                   10                  15

Leu Val Asn Ser
            20

<210> SEQ ID NO 61
<211> LENGTH: 24
<212> TYPE: PRT
<213> ORGANISM: Mus musculus
<220> FEATURE:
<221> NAME/KEY: MISC_FEATURE
<222> LOCATION: (1)..(24)
<223> OTHER INFORMATION: IL-6

<400> SEQUENCE: 61

Met Lys Phe Leu Ser Ala Arg Asp Phe His Pro Val Ala Phe Leu Gly
1               5                   10                  15

Leu Met Leu Val Thr Thr Thr Ala
            20

<210> SEQ ID NO 62
<211> LENGTH: 25
<212> TYPE: PRT
<213> ORGANISM: Homo sapiens
<220> FEATURE:
<221> NAME/KEY: MISC_FEATURE
<222> LOCATION: (1)..(25)
<223> OTHER INFORMATION: IL-7

<400> SEQUENCE: 62

Met Phe His Val Ser Phe Arg Tyr Ile Phe Gly Leu Pro Pro Leu Ile
1               5                   10                  15

Leu Val Leu Leu Pro Val Ala Ser Ser
            20                  25

<210> SEQ ID NO 63
<211> LENGTH: 18
<212> TYPE: PRT
<213> ORGANISM: Mus musculus
<220> FEATURE:
<221> NAME/KEY: MISC_FEATURE
<222> LOCATION: (1)..(18)
<223> OTHER INFORMATION: IL-10

<400> SEQUENCE: 63

Met Pro Gly Ser Ala Leu Leu Cys Cys Leu Leu Leu Thr Gly Met
1               5                   10                  15

Arg Ile

<210> SEQ ID NO 64
<211> LENGTH: 23
<212> TYPE: PRT
<213> ORGANISM: Homo sapiens
<220> FEATURE:
<221> NAME/KEY: MISC_FEATURE
<222> LOCATION: (1)..(23)
<223> OTHER INFORMATION: MIP-1-alpha chemokine

<400> SEQUENCE: 64

Met Gln Val Ser Thr Ala Ala Leu Ala Val Leu Leu Cys Thr Met Ala
1               5                   10                  15
```

-continued

Leu Cys Asn Gln Phe Ser Ala
            20

<210> SEQ ID NO 65
<211> LENGTH: 15
<212> TYPE: PRT
<213> ORGANISM: Influenza B virus
<220> FEATURE:
<221> NAME/KEY: MISC_FEATURE
<222> LOCATION: (1)..(15)
<223> OTHER INFORMATION: Influenza B virus hemagglutinin

<400> SEQUENCE: 65

Met Lys Ala Ile Ile Val Leu Leu Met Val Val Thr Ser Asn Ala
1               5                   10                  15

<210> SEQ ID NO 66
<211> LENGTH: 16
<212> TYPE: PRT
<213> ORGANISM: Influenza A virus
<220> FEATURE:
<221> NAME/KEY: MISC_FEATURE
<222> LOCATION: (1)..(16)
<223> OTHER INFORMATION: Influenza A H1N1 virus  hemagglutinin

<400> SEQUENCE: 66

Met Lys Ala Lys Leu Leu Val Leu Leu Cys Ala Leu Ser Ala Thr Asp
1               5                   10                  15

<210> SEQ ID NO 67
<211> LENGTH: 15
<212> TYPE: PRT
<213> ORGANISM: Influenza A virus
<220> FEATURE:
<221> NAME/KEY: MISC_FEATURE
<222> LOCATION: (1)..(15)
<223> OTHER INFORMATION: Influenza A H2N2 virus hemagglutinin

<400> SEQUENCE: 67

Met Ala Ile Ile Tyr Leu Ile Leu Leu Phe Thr Ala Val Arg Gly
1               5                   10                  15

<210> SEQ ID NO 68
<211> LENGTH: 16
<212> TYPE: PRT
<213> ORGANISM: Influenza A virus
<220> FEATURE:
<221> NAME/KEY: MISC_FEATURE
<222> LOCATION: (1)..(16)
<223> OTHER INFORMATION: Influenza A H3N2 virus hemagglutinin

<400> SEQUENCE: 68

Met Lys Thr Ile Ile Ala Leu Ser Tyr Ile Phe Cys Leu Ala Leu Gly
1               5                   10                  15

<210> SEQ ID NO 69
<211> LENGTH: 16
<212> TYPE: PRT
<213> ORGANISM: Influenza A virus
<220> FEATURE:
<221> NAME/KEY: MISC_FEATURE
<222> LOCATION: (1)..(16)
<223> OTHER INFORMATION: Influenza A H4N6 virus hemagglutinin

<400> SEQUENCE: 69

Met Leu Ser Ile Val Ile Leu Phe Leu Leu Ile Ala Glu Asn Ser Ser
1               5                   10                  15

```
<210> SEQ ID NO 70
<211> LENGTH: 16
<212> TYPE: PRT
<213> ORGANISM: Influenza A virus
<220> FEATURE:
<221> NAME/KEY: MISC_FEATURE
<222> LOCATION: (1)..(16)
<223> OTHER INFORMATION: Influenza A H5N1 virus hemagglutinin

<400> SEQUENCE: 70

Met Glu Lys Ile Val Leu Leu Leu Ala Ile Ile Ser Leu Val Lys Ser
1               5                   10                  15

<210> SEQ ID NO 71
<211> LENGTH: 16
<212> TYPE: PRT
<213> ORGANISM: Influenza A virus
<220> FEATURE:
<221> NAME/KEY: MISC_FEATURE
<222> LOCATION: (1)..(16)
<223> OTHER INFORMATION: Influenza A H6N5 virus hemagglutinin

<400> SEQUENCE: 71

Met Ile Ala Ile Ile Val Val Ala Ile Leu Ala Thr Ala Gly Arg Ser
1               5                   10                  15

<210> SEQ ID NO 72
<211> LENGTH: 18
<212> TYPE: PRT
<213> ORGANISM: Influenza A virus
<220> FEATURE:
<221> NAME/KEY: MISC_FEATURE
<222> LOCATION: (1)..(18)
<223> OTHER INFORMATION: Influenza A H7N7 virus hemagglutinin

<400> SEQUENCE: 72

Met Asn Thr Gln Ile Leu Ile Leu Thr Leu Val Ala Ala Ile His Thr
1               5                   10                  15

Asn Ala

<210> SEQ ID NO 73
<211> LENGTH: 16
<212> TYPE: PRT
<213> ORGANISM: Influenza A virus
<220> FEATURE:
<221> NAME/KEY: MISC_FEATURE
<222> LOCATION: (1)..(16)
<223> OTHER INFORMATION: Influenza A H8N4 virus hemagglutinin

<400> SEQUENCE: 73

Met Glu Lys Phe Ile Ala Ile Ala Thr Leu Ala Ser Thr Asn Ala Tyr
1               5                   10                  15

<210> SEQ ID NO 74
<211> LENGTH: 18
<212> TYPE: PRT
<213> ORGANISM: Influenza A virus
<220> FEATURE:
<221> NAME/KEY: MISC_FEATURE
<222> LOCATION: (1)..(18)
<223> OTHER INFORMATION: Influenza A H9N2 virus hemagglutinin

<400> SEQUENCE: 74

Met Glu Thr Lys Ala Ile Ile Ala Ala Leu Leu Met Val Thr Ala Ala
1               5                   10                  15

Asn Ala
```

-continued

```
<210> SEQ ID NO 75
<211> LENGTH: 16
<212> TYPE: PRT
<213> ORGANISM: Influenza A virus
<220> FEATURE:
<221> NAME/KEY: MISC_FEATURE
<222> LOCATION: (1)..(16)
<223> OTHER INFORMATION: Influenza A H10N7 virus hemagglutinin

<400> SEQUENCE: 75

Met Tyr Lys Val Val Val Ile Ile Ala Leu Leu Gly Ala Val Lys Gly
1               5                   10                  15

<210> SEQ ID NO 76
<211> LENGTH: 16
<212> TYPE: PRT
<213> ORGANISM: Influenza A virus
<220> FEATURE:
<221> NAME/KEY: MISC_FEATURE
<222> LOCATION: (1)..(16)
<223> OTHER INFORMATION: Influenza A H11N6 virus hemagglutinin

<400> SEQUENCE: 76

Met Glu Lys Thr Leu Leu Phe Ala Ala Ile Phe Leu Cys Val Lys Ala
1               5                   10                  15

<210> SEQ ID NO 77
<211> LENGTH: 17
<212> TYPE: PRT
<213> ORGANISM: Influenza A virus
<220> FEATURE:
<221> NAME/KEY: MISC_FEATURE
<222> LOCATION: (1)..(17)
<223> OTHER INFORMATION: Influenza A H12N5 virus hemagglutinin

<400> SEQUENCE: 77

Met Glu Lys Phe Ile Ile Leu Ser Thr Val Leu Ala Ala Ser Phe Ala
1               5                   10                  15
Tyr

<210> SEQ ID NO 78
<211> LENGTH: 18
<212> TYPE: PRT
<213> ORGANISM: Influenza A virus
<220> FEATURE:
<221> NAME/KEY: MISC_FEATURE
<222> LOCATION: (1)..(18)
<223> OTHER INFORMATION: Influenza A H13N6 virus hemagglutinin

<400> SEQUENCE: 78

Met Ala Leu Asn Val Ile Ala Thr Leu Thr Leu Ile Ser Val Cys Val
1               5                   10                  15
His Ala

<210> SEQ ID NO 79
<211> LENGTH: 246
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(246)
<223> OTHER INFORMATION: Construct X2
<220> FEATURE:
<221> NAME/KEY: CDS
<222> LOCATION: (1)..(246)

<400> SEQUENCE: 79
```

```
ctc att cat tct gtt cta agc cta ttc cta tta gcc ctt ttt ttg ctc      48
Leu Ile His Ser Val Leu Ser Leu Phe Leu Leu Ala Leu Phe Leu Leu
1               5                   10                  15 ttc ttg gcc ccc tgc ctg ata aaa tgc ttg acc tct cgc ctt tta aaa      96
Phe Leu Ala Pro Cys Leu Ile Lys Cys Leu Thr Ser Arg Leu Leu Lys
            20                  25                  30 ctc ctc cgg cag gct ccc cac ttc cct gaa atc tcc ttc ccc cct aaa     144
Leu Leu Arg Gln Ala Pro His Phe Pro Glu Ile Ser Phe Pro Pro Lys
        35                  40                  45 ccc gat tct gat tat cag gcc ttg cta cca tcc gcg cca gag atc tac     192
Pro Asp Ser Asp Tyr Gln Ala Leu Leu Pro Ser Ala Pro Glu Ile Tyr
    50                  55                  60 tct cac ctc tcc ccc acc aaa ccc gat tac atc aac ctt cga ccc tgc     240
Ser His Leu Ser Pro Thr Lys Pro Asp Tyr Ile Asn Leu Arg Pro Cys
65                  70                  75                  80 ccc tag                                                              246
Pro
```

<210> SEQ ID NO 80
<211> LENGTH: 81
<212> TYPE: PRT
<213> ORGANISM: Artificial Sequence
<220> FEATURE:
<223> OTHER INFORMATION: Synthetic Construct

<400> SEQUENCE: 80

```
Leu Ile His Ser Val Leu Ser Leu Phe Leu Leu Ala Leu Phe Leu Leu
1               5                   10                  15

Phe Leu Ala Pro Cys Leu Ile Lys Cys Leu Thr Ser Arg Leu Leu Lys
            20                  25                  30

Leu Leu Arg Gln Ala Pro His Phe Pro Glu Ile Ser Phe Pro Pro Lys
        35                  40                  45

Pro Asp Ser Asp Tyr Gln Ala Leu Leu Pro Ser Ala Pro Glu Ile Tyr
    50                  55                  60

Ser His Leu Ser Pro Thr Lys Pro Asp Tyr Ile Asn Leu Arg Pro Cys
65                  70                  75                  80

Pro
```

<210> SEQ ID NO 81
<211> LENGTH: 246
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(246)
<223> OTHER INFORMATION: Construct X3
<220> FEATURE:
<221> NAME/KEY: CDS
<222> LOCATION: (1)..(246)

<400> SEQUENCE: 81

```
att tac atc tgg gca ccc ttg gcc gga atc tgc gtg gcc ctt ctg cta      48
Ile Tyr Ile Trp Ala Pro Leu Ala Gly Ile Cys Val Ala Leu Leu Leu
1               5                   10                  15 agc ttg atc ccc tgc ctg ata aaa tgc ctg acc tct cgc ctt tta aaa      96
Ser Leu Ile Pro Cys Leu Ile Lys Cys Leu Thr Ser Arg Leu Leu Lys
            20                  25                  30 ctc ctc cgg cag gct ccc cac ttc cct gaa atc tcc ttc ccc cct aaa     144
Leu Leu Arg Gln Ala Pro His Phe Pro Glu Ile Ser Phe Pro Pro Lys
        35                  40                  45
```

```
ccc gat tct gat tat cag gcc ttg cta cca tcc gcg cca gag atc tac      192
Pro Asp Ser Asp Tyr Gln Ala Leu Leu Pro Ser Ala Pro Glu Ile Tyr
    50                  55                  60 tct cac ctc tcc ccc acc aaa ccc gat tac atc aac ctt cga ccc tgc      240
Ser His Leu Ser Pro Thr Lys Pro Asp Tyr Ile Asn Leu Arg Pro Cys
65                  70                  75                  80 ccc tag                                                               246
Pro
```

<210> SEQ ID NO 82
<211> LENGTH: 81
<212> TYPE: PRT
<213> ORGANISM: Artificial Sequence
<220> FEATURE:
<223> OTHER INFORMATION: Synthetic Construct

<400> SEQUENCE: 82

Ile Tyr Ile Trp Ala Pro Leu Ala Gly Ile Cys Val Ala Leu Leu Leu
1               5                   10                  15

Ser Leu Ile Pro Cys Leu Ile Lys Cys Leu Thr Ser Arg Leu Leu Lys
            20                  25                  30

Leu Leu Arg Gln Ala Pro His Phe Pro Glu Ile Ser Phe Pro Pro Lys
        35                  40                  45

Pro Asp Ser Asp Tyr Gln Ala Leu Leu Pro Ser Ala Pro Glu Ile Tyr
    50                  55                  60

Ser His Leu Ser Pro Thr Lys Pro Asp Tyr Ile Asn Leu Arg Pro Cys
65                  70                  75                  80

Pro

<210> SEQ ID NO 83
<211> LENGTH: 225
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(225)
<223> OTHER INFORMATION: Construct X4
<220> FEATURE:
<221> NAME/KEY: CDS
<222> LOCATION: (1)..(225)

<400> SEQUENCE: 83

```
att tac atc tgg gca ccc ttg gcc gga atc tgc gtg gcc ctt ctg ctg       48
Ile Tyr Ile Trp Ala Pro Leu Ala Gly Ile Cys Val Ala Leu Leu Leu
1               5                   10                  15 tcc ttg atc atc act ctc atc tgc tac cac agg tct aga gct ccc cac       96
Ser Leu Ile Ile Thr Leu Ile Cys Tyr His Arg Ser Arg Ala Pro His
            20                  25                  30 ttc cct gaa atc tcc ttc ccc cct aaa ccc gat tct gat tat cag gcc      144
Phe Pro Glu Ile Ser Phe Pro Pro Lys Pro Asp Ser Asp Tyr Gln Ala
        35                  40                  45 ttg cta cca tcc gcg cca gag atc tac tct cac ctc tcc ccc acc aaa      192
Leu Leu Pro Ser Ala Pro Glu Ile Tyr Ser His Leu Ser Pro Thr Lys
    50                  55                  60 ccc gat tac atc aac ctt cga ccc tgc ccc tag                          225
Pro Asp Tyr Ile Asn Leu Arg Pro Cys Pro
65                  70
```

<210> SEQ ID NO 84
<211> LENGTH: 74

```
<212> TYPE: PRT
<213> ORGANISM: Artificial Sequence
<220> FEATURE:
<223> OTHER INFORMATION: Synthetic Construct

<400> SEQUENCE: 84

Ile Tyr Ile Trp Ala Pro Leu Ala Gly Ile Cys Val Ala Leu Leu Leu
1               5                   10                  15

Ser Leu Ile Ile Thr Leu Ile Cys Tyr His Arg Ser Arg Ala Pro His
            20                  25                  30

Phe Pro Glu Ile Ser Phe Pro Pro Lys Pro Asp Ser Asp Tyr Gln Ala
        35                  40                  45

Leu Leu Pro Ser Ala Pro Glu Ile Tyr Ser His Leu Ser Pro Thr Lys
    50                  55                  60

Pro Asp Tyr Ile Asn Leu Arg Pro Cys Pro
65                  70

<210> SEQ ID NO 85
<211> LENGTH: 947
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(947)
<223> OTHER INFORMATION: mouse Cd8 alpha / CD domain of TM of BLV
      chimera
<220> FEATURE:
<221> NAME/KEY: CDS
<222> LOCATION: (28)..(831)

<400> SEQUENCE: 85
```

| | | |
|---|---|---|
| ggatcccttg ctggtggaga gcacacc atg gcc tca ccg ttg acc cgc ttt ctg | | 54 |
|                                       Met Ala Ser Pro Leu Thr Arg Phe Leu | | |
|                                       1                     5 | | |

```
tcg ctg aac ctg ctg ctg ctg ggt gag tcg att atc ctg ggg agt gga    102
Ser Leu Asn Leu Leu Leu Leu Gly Glu Ser Ile Ile Leu Gly Ser Gly
10                  15                  20                  25 gaa gct aag cca cag gca ccc gaa ctc cga atc ttt cca aag aaa atg    150
Glu Ala Lys Pro Gln Ala Pro Glu Leu Arg Ile Phe Pro Lys Lys Met
                30                  35                  40 gac gcc gaa ctt ggt cag aag gtg gac ctg gta tgt gaa gtg ttg ggg    198
Asp Ala Glu Leu Gly Gln Lys Val Asp Leu Val Cys Glu Val Leu Gly
            45                  50                  55 tcc gtt tcg caa gga tgc tct tgg ctc ttc cag aac tcc agc tcc aaa    246
Ser Val Ser Gln Gly Cys Ser Trp Leu Phe Gln Asn Ser Ser Ser Lys
        60                  65                  70 ctc ccc cag ccc acc ttc gtt gtc tat atg gct tca tcc cac aac aag    294
Leu Pro Gln Pro Thr Phe Val Val Tyr Met Ala Ser Ser His Asn Lys
    75                  80                  85 ata acg tgg gac gag aag ctg aat tcg tcg aaa ctg ttt tct gcc atg    342
Ile Thr Trp Asp Glu Lys Leu Asn Ser Ser Lys Leu Phe Ser Ala Met
90                  95                  100                 105 agg gac acg aat aat aag tac gtt ctc acc ctg aac aag ttc agc aag    390
Arg Asp Thr Asn Asn Lys Tyr Val Leu Thr Leu Asn Lys Phe Ser Lys
                110                 115                 120 gaa aac gaa ggc tac tat ttc tgc tca gtc atc agc aac tcg gtg atg    438
Glu Asn Glu Gly Tyr Tyr Phe Cys Ser Val Ile Ser Asn Ser Val Met
            125                 130                 135 tac ttc agt tct gtc gtg cca gtc ctt cag aaa gtg aac tct act act    486
Tyr Phe Ser Ser Val Val Pro Val Leu Gln Lys Val Asn Ser Thr Thr
        140                 145                 150
```

```
acc aag cca gtg ctg cga act ccc tca cct gtg cac cct acc ggg aca     534
Thr Lys Pro Val Leu Arg Thr Pro Ser Pro Val His Pro Thr Gly Thr
    155                 160                 165 tct cag ccc cag aga cca gaa gat tgt cgg ccc cgt ggc tca gtg aag     582
Ser Gln Pro Gln Arg Pro Glu Asp Cys Arg Pro Arg Gly Ser Val Lys
170                 175                 180                 185 ggg acc gga ttg gac ttc gcc tgt gat att tac atc tgg gca ccc ttg     630
Gly Thr Gly Leu Asp Phe Ala Cys Asp Ile Tyr Ile Trp Ala Pro Leu
                190                 195                 200 gcc gga atc tgc gtg gcc ctt ctg ctg tcc ttg atc atc act ctc atc     678
Ala Gly Ile Cys Val Ala Leu Leu Leu Ser Leu Ile Ile Thr Leu Ile
            205                 210                 215 tgc tac cac agg tct aga gct ccc cac ttc cct gaa atc tcc ttc ccc     726
Cys Tyr His Arg Ser Arg Ala Pro His Phe Pro Glu Ile Ser Phe Pro
        220                 225                 230 cct aaa ccc gat tct gat tat cag gcc ttg cta cca tcc gcg cca gag     774
Pro Lys Pro Asp Ser Asp Tyr Gln Ala Leu Leu Pro Ser Ala Pro Glu
    235                 240                 245 atc tac tct cac ctc tcc ccc acc aaa ccc gat tac atc aac ctt cga     822
Ile Tyr Ser His Leu Ser Pro Thr Lys Pro Asp Tyr Ile Asn Leu Arg
250                 255                 260                 265 ccc tgc ccc taggacccccc atgtttcacg caccctcagg ctgtggtggg            871
Pro Cys Pro gcactggctt agtggaatag tcagtgtacc atcacaagcc tcttcttgct gccagcaccg   931
agttcgaagc ggccgc                                                   947

<210> SEQ ID NO 86
<211> LENGTH: 268
<212> TYPE: PRT
<213> ORGANISM: Artificial Sequence
<220> FEATURE:
<223> OTHER INFORMATION: Synthetic Construct

<400> SEQUENCE: 86

Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala Lys Pro Gln Ala Pro
            20                  25                  30

Glu Leu Arg Ile Phe Pro Lys Lys Met Asp Ala Glu Leu Gly Gln Lys
        35                  40                  45

Val Asp Leu Val Cys Glu Val Leu Gly Ser Val Ser Gln Gly Cys Ser
    50                  55                  60

Trp Leu Phe Gln Asn Ser Ser Ser Lys Leu Pro Gln Pro Thr Phe Val
65                  70                  75                  80

Val Tyr Met Ala Ser Ser His Asn Lys Ile Thr Trp Asp Glu Lys Leu
                85                  90                  95

Asn Ser Ser Lys Leu Phe Ser Ala Met Arg Asp Thr Asn Asn Lys Tyr
            100                 105                 110

Val Leu Thr Leu Asn Lys Phe Ser Lys Glu Asn Glu Gly Tyr Tyr Phe
        115                 120                 125

Cys Ser Val Ile Ser Asn Ser Val Met Tyr Phe Ser Ser Val Val Pro
    130                 135                 140

Val Leu Gln Lys Val Asn Ser Thr Thr Thr Lys Pro Val Leu Arg Thr
145                 150                 155                 160

Pro Ser Pro Val His Pro Thr Gly Thr Ser Gln Pro Gln Arg Pro Glu
                165                 170                 175
```

```
Asp Cys Arg Pro Arg Gly Ser Val Lys Gly Thr Gly Leu Asp Phe Ala
            180                 185                 190

Cys Asp Ile Tyr Ile Trp Ala Pro Leu Ala Gly Ile Cys Val Ala Leu
        195                 200                 205

Leu Leu Ser Leu Ile Ile Thr Leu Ile Cys Tyr His Arg Ser Arg Ala
    210                 215                 220

Pro His Phe Pro Glu Ile Ser Phe Pro Pro Lys Pro Asp Ser Asp Tyr
225                 230                 235                 240

Gln Ala Leu Leu Pro Ser Ala Pro Glu Ile Tyr Ser His Leu Ser Pro
                245                 250                 255

Thr Lys Pro Asp Tyr Ile Asn Leu Arg Pro Cys Pro
            260                 265
```

<210> SEQ ID NO 87
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: CDS
<222> LOCATION: (1)..(12)

<400> SEQUENCE: 87 cca tcc gcg cca                                                    12
Pro Ser Ala Pro
1

<210> SEQ ID NO 88
<211> LENGTH: 4
<212> TYPE: PRT
<213> ORGANISM: Artificial Sequence
<220> FEATURE:
<223> OTHER INFORMATION: Synthetic Construct

<400> SEQUENCE: 88

Pro Ser Ala Pro
1

<210> SEQ ID NO 89
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 89

Pro Thr Ala Pro
1

<210> SEQ ID NO 90
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: CDS
<222> LOCATION: (1)..(12)

<400> SEQUENCE: 90 tac atc aac ctt                                                    12
Tyr Ile Asn Leu
1

-continued

```
<210> SEQ ID NO 91
<211> LENGTH: 4
<212> TYPE: PRT
<213> ORGANISM: Artificial Sequence
<220> FEATURE:
<223> OTHER INFORMATION: Synthetic Construct

<400> SEQUENCE: 91

Tyr Ile Asn Leu
1

<210> SEQ ID NO 92
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: CDS
<222> LOCATION: (1)..(15)

<400> SEQUENCE: 92 gat tac atc aac ctt                                              15
Asp Tyr Ile Asn Leu
1               5

<210> SEQ ID NO 93
<211> LENGTH: 5
<212> TYPE: PRT
<213> ORGANISM: Artificial Sequence
<220> FEATURE:
<223> OTHER INFORMATION: Synthetic Construct

<400> SEQUENCE: 93

Asp Tyr Ile Asn Leu
1               5

<210> SEQ ID NO 94
<211> LENGTH: 60
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: CDS
<222> LOCATION: (1)..(60)
<220> FEATURE:
<221> NAME/KEY: misc_feature
<222> LOCATION: (1)..(60)
<223> OTHER INFORMATION: Mutated derivative of the CD of the TM protein
      of BLV

<400> SEQUENCE: 94 cca tcc gcg cca gag atc tac tct cac ctc tcc ccc acc aaa ccc gat    48
Pro Ser Ala Pro Glu Ile Tyr Ser His Leu Ser Pro Thr Lys Pro Asp
1               5                   10                  15 tac atc aac ctt                                                    60
Tyr Ile Asn Leu
            20

<210> SEQ ID NO 95
<211> LENGTH: 20
<212> TYPE: PRT
<213> ORGANISM: Artificial Sequence
<220> FEATURE:
<223> OTHER INFORMATION: Synthetic Construct

<400> SEQUENCE: 95

Pro Ser Ala Pro Glu Ile Tyr Ser His Leu Ser Pro Thr Lys Pro Asp
```

```
                1               5                    10                   15
Tyr Ile Asn Leu
            20

<210> SEQ ID NO 96
<211> LENGTH: 12
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(12)

<400> SEQUENCE: 96 tac tct cac ctc                                                          12
Tyr Ser His Leu
1

<210> SEQ ID NO 97
<211> LENGTH: 4
<212> TYPE: PRT
<213> ORGANISM: Artificial Sequence
<220> FEATURE:
<223> OTHER INFORMATION: Synthetic Construct

<400> SEQUENCE: 97

Tyr Ser His Leu
1

<210> SEQ ID NO 98
<211> LENGTH: 40
<212> TYPE: DNA
<213> ORGANISM: Artificial Sequence
<220> FEATURE:
<223> OTHER INFORMATION: S to A primer, forward

<400> SEQUENCE: 98
ccctaaaccc gatgctgatt atcaggcgtt gctaccatcc                              40

<210> SEQ ID NO 99
<211> LENGTH: 40
<212> TYPE: DNA
<213> ORGANISM: Artificial Sequence
<220> FEATURE:
<223> OTHER INFORMATION: S to A primer, reverse

<400> SEQUENCE: 99
cgcggatggt agcaacgcct gataatcagc atcgggttta                              40

<210> SEQ ID NO 100
<211> LENGTH: 25
<212> TYPE: DNA
<213> ORGANISM: Artificial Sequence
<220> FEATURE:
<223> OTHER INFORMATION: D to A primer, forward

<400> SEQUENCE: 100
ccaccaagcc ggcatacatc aacct                                              25

<210> SEQ ID NO 101
<211> LENGTH: 27
<212> TYPE: DNA
<213> ORGANISM: Artificial Sequence
<220> FEATURE:
<223> OTHER INFORMATION: D to A primer, reverse
```

<400> SEQUENCE: 101
tcgaaggttg atgtatgccg gcttggt                                                27

<210> SEQ ID NO 102
<211> LENGTH: 25
<212> TYPE: DNA
<213> ORGANISM: Artificial Sequence
<220> FEATURE:
<223> OTHER INFORMATION: E to A primer, forward

<400> SEQUENCE: 102
gctaccatcc gcgccagcga tctac                                                  25

<210> SEQ ID NO 103
<211> LENGTH: 23
<212> TYPE: DNA
<213> ORGANISM: Artificial Sequence
<220> FEATURE:
<223> OTHER INFORMATION: E to A primer, reverse

<400> SEQUENCE: 103
gtagatcgct ggcgcggatg gta                                                    23

<210> SEQ ID NO 104
<211> LENGTH: 16
<212> TYPE: PRT
<213> ORGANISM: Artificial Sequence
<220> FEATURE:
<223> OTHER INFORMATION: Synthetic polypeptide - infra-membrane
      targeting domain derived from a Src protein

<400> SEQUENCE: 104

Met Gly Ser Ser Lys Ser Lys Pro Lys Asp Pro Ser Gln Arg Arg Arg
1               5                   10                  15

<210> SEQ ID NO 105
<211> LENGTH: 23
<212> TYPE: PRT
<213> ORGANISM: Artificial Sequence
<220> FEATURE:
<223> OTHER INFORMATION: Synthetic polypeptide - infra-membrane
      targeting domain derived from a Src protein

<400> SEQUENCE: 105

Met Gly Ser Ser Lys Ser Lys Pro Lys Asp Pro Ser Gln Arg Arg Arg
1               5                   10                  15

Lys Ser Arg Gly Pro Gly Gly
            20

<210> SEQ ID NO 106
<211> LENGTH: 7
<212> TYPE: PRT
<213> ORGANISM: Artificial Sequence
<220> FEATURE:
<223> OTHER INFORMATION: Synthetic polypeptide - linker

<400> SEQUENCE: 106

Pro Ala Gly Ser Gly Ala Pro
1               5

<210> SEQ ID NO 107
<211> LENGTH: 21
<212> TYPE: DNA
<213> ORGANISM: Artificial Sequence
<220> FEATURE:
<223> OTHER INFORMATION: Synthetic oligonucleotide - linker

<400> SEQUENCE: 107
cctgcaggaa gcggcgcgcc c                                              21

<210> SEQ ID NO 108
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 108
gccaccatgg gcagcagcaa gagcaagccc aaggac                              36

<210> SEQ ID NO 109
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 109
cccagccagc gccgccgcaa gtctagaggc ccgggaggc                           39

<210> SEQ ID NO 110
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 110
gcctcccggg cctctagact tg                                             22

<210> SEQ ID NO 111
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 111
cggcggcgct ggctggggtc cttgggcttg ctctt                               35

<210> SEQ ID NO 112
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 112
gctgctgccc atggtggc                                                  18

<210> SEQ ID NO 113
<211> LENGTH: 33
<212> TYPE: DNA
<213> ORGANISM: Artificial Sequence
<220> FEATURE:
<223> OTHER INFORMATION: Synthetic oligonucleotide - R1Src

<400> SEQUENCE: 113
gaattcgcca ccatgggcag cagcaagagc aag                                 33

<210> SEQ ID NO 114

```
<211> LENGTH: 35
<212> TYPE: DNA
<213> ORGANISM: Artificial Sequence
<220> FEATURE:
<223> OTHER INFORMATION: Synthetic oligonucleotide - SrcNhe 1

<400> SEQUENCE: 114
catgctagcg ctgcctcccg ggcctctaga ctttc                              35

<210> SEQ ID NO 115
<211> LENGTH: 37
<212> TYPE: DNA
<213> ORGANISM: Artificial Sequence
<220> FEATURE:
<223> OTHER INFORMATION: Synthetic oligonucleotide - NheSNAP

<400> SEQUENCE: 115
ggaggcagcg ctagcatgga caaagactgc gaaatga                            37

<210> SEQ ID NO 116
<211> LENGTH: 35
<212> TYPE: DNA
<213> ORGANISM: Artificial Sequence
<220> FEATURE:
<223> OTHER INFORMATION: Synthetic oligonucleotide - SNAPSbfAsc

<400> SEQUENCE: 116
gcgcgccgct tcctgcagga cccagcccag gcttg                              35

<210> SEQ ID NO 117
<211> LENGTH: 36
<212> TYPE: DNA
<213> ORGANISM: Artificial Sequence
<220> FEATURE:
<223> OTHER INFORMATION: Synthetic oligonucleotide - SbfscDCTM15

<400> SEQUENCE: 117
cctgcaggaa gcggcgcgcc ccacttccct gaaatc                             36

<210> SEQ ID NO 118
<211> LENGTH: 33
<212> TYPE: DNA
<213> ORGANISM: Artificial Sequence
<220> FEATURE:
<223> OTHER INFORMATION: Synthetic oligonucleotide - DCTM15Not

<400> SEQUENCE: 118
gcggccgctt cgaactcggt gctggcagca aga                                33

<210> SEQ ID NO 119
<211> LENGTH: 268
<212> TYPE: DNA
<213> ORGANISM: Artificial Sequence
<220> FEATURE:
<223> OTHER INFORMATION: Synthetic polynucleotide - CD domain :
      SbfAscDCTM_M15 Not

<400> SEQUENCE: 119
cctgcaggaa ggctggcgcg ccccacttcc ctgaaatctc cttccccct aaacccgatt    60 ctgattatca ggccttgcta ccatccgcgc cagagatcta ctctcacctc tcccccacca   120
aacccgatta catcaacctt cgaccggcgc cctaggaccc ccatgtttca cgcaccctca   180
ggctgtggtg gggcactggc ttagtggaat agtcagtgta ccatcacaag cctcttcttg   240
ctgccagcac cgagttcgaa gcggccgc                                     268
```

<210> SEQ ID NO 120
<211> LENGTH: 75
<212> TYPE: DNA
<213> ORGANISM: Artificial Sequence
<220> FEATURE:
<223> OTHER INFORMATION: Synthetic polynucleotide - Src fragment

<400> SEQUENCE: 120

```
gccaccatgg gcagcagcaa gagcaagccc aaggacccca gccagcgccg ccgcaagtct      60
agaggcccgg gaggc                                                      75
```

<210> SEQ ID NO 121
<211> LENGTH: 902
<212> TYPE: DNA
<213> ORGANISM: Artificial Sequence
<220> FEATURE:
<223> OTHER INFORMATION: Synthetic polynucleotide - Src-SNAP-DCTM (SSC)
      gene
<220> FEATURE:
<221> NAME/KEY: CDS
<222> LOCATION: (13)..(789)

<400> SEQUENCE: 121

```
gaattcgcca cc atg ggc agc agc aag agc aag ccc aag gac ccc agc cag      51
              Met Gly Ser Ser Lys Ser Lys Pro Lys Asp Pro Ser Gln
                1               5                  10 cgc cgc cgc aag tct aga ggc ccg gga ggc agc gct agc atg gac aaa        99
Arg Arg Arg Lys Ser Arg Gly Pro Gly Gly Ser Ala Ser Met Asp Lys
         15                  20                  25 gac tgc gaa atg aag cgc acc acc ctg gat agc cct ctg ggc aag ctg       147
Asp Cys Glu Met Lys Arg Thr Thr Leu Asp Ser Pro Leu Gly Lys Leu
 30                  35                  40                  45 gaa ctg tct ggg tgc gaa cag ggc ctg cac gag atc aag ctg ctg ggc       195
Glu Leu Ser Gly Cys Glu Gln Gly Leu His Glu Ile Lys Leu Leu Gly
                 50                  55                  60 aaa gga aca tct gcc gcc gac gcc gtg gaa gtg cct gcc cca gcc gcc       243
Lys Gly Thr Ser Ala Ala Asp Ala Val Glu Val Pro Ala Pro Ala Ala
             65                  70                  75 gtg ctg ggc gga cca gag cca ctg atg cag gcc acc gcc tgg ctc aac       291
Val Leu Gly Gly Pro Glu Pro Leu Met Gln Ala Thr Ala Trp Leu Asn
         80                  85                  90 gcc tac ttt cac cag cct gag gcc atc gag gag ttc cct gtg cca gcc       339
Ala Tyr Phe His Gln Pro Glu Ala Ile Glu Glu Phe Pro Val Pro Ala
     95                 100                 105 ctg cac cac cca gtg ttc cag cag gag agc ttt acc cgc cag gtg ctg       387
Leu His His Pro Val Phe Gln Gln Glu Ser Phe Thr Arg Gln Val Leu
110                 115                 120                 125 tgg aaa ctg ctg aaa gtg gtg aag ttc gga gag gtc atc agc tac cag       435
Trp Lys Leu Leu Lys Val Val Lys Phe Gly Glu Val Ile Ser Tyr Gln
                130                 135                 140 cag ctg gcc gcc ctg gcc ggc aat ccc gcc gcc acc gcc gcc gtg aaa       483
Gln Leu Ala Ala Leu Ala Gly Asn Pro Ala Ala Thr Ala Ala Val Lys
            145                 150                 155 acc gcc ctg agc gga aat ccc gtg ccc att ctg atc ccc tgc cac cgg       531
Thr Ala Leu Ser Gly Asn Pro Val Pro Ile Leu Ile Pro Cys His Arg
        160                 165                 170 gtg gtg tct agc tct ggc gcc gtg ggg ggc tac gag ggc ggg ctc gcc       579
Val Val Ser Ser Ser Gly Ala Val Gly Gly Tyr Glu Gly Gly Leu Ala
    175                 180                 185 gtg aaa gag tgg ctg ctg gcc cac gag ggc cac aga ctg ggc aag cct       627
Val Lys Glu Trp Leu Leu Ala His Glu Gly His Arg Leu Gly Lys Pro
190                 195                 200                 205
```

```
ggg ctg ggt cct gca gga agc ggc gcg ccc cac ttc cct gaa atc tcc      675
Gly Leu Gly Pro Ala Gly Ser Gly Ala Pro His Phe Pro Glu Ile Ser
                210                 215                 220 ttc ccc cct aaa ccc gat tct gat tat cag gcc ttg cta cca tcc gcg      723
Phe Pro Pro Lys Pro Asp Ser Asp Tyr Gln Ala Leu Leu Pro Ser Ala
            225                 230                 235 cca gag atc tac tct cac ctc tcc ccc acc aaa ccc gat tac atc aac      771
Pro Glu Ile Tyr Ser His Leu Ser Pro Thr Lys Pro Asp Tyr Ile Asn
        240                 245                 250 ctt cga ccg gcg ccc tag gaccccatg tttcacgcac cctcaggctg              819
Leu Arg Pro Ala Pro
    255 tggtggggca ctggcttagt ggaatagtca gtgtaccatc acaagcctct tcttgctgcc    879 agcaccgagt tcgaagcggc cgc                                            902
```

<210> SEQ ID NO 122
<211> LENGTH: 258
<212> TYPE: PRT
<213> ORGANISM: Artificial Sequence
<220> FEATURE:
<223> OTHER INFORMATION: Synthetic Construct

<400> SEQUENCE: 122

```
Met Gly Ser Ser Lys Ser Lys Pro Lys Asp Pro Ser Gln Arg Arg Arg
1               5                   10                  15

Lys Ser Arg Gly Pro Gly Gly Ser Ala Ser Met Asp Lys Asp Cys Glu
            20                  25                  30

Met Lys Arg Thr Thr Leu Asp Ser Pro Leu Gly Lys Leu Glu Leu Ser
        35                  40                  45

Gly Cys Glu Gln Gly Leu His Glu Ile Lys Leu Leu Gly Lys Gly Thr
    50                  55                  60

Ser Ala Ala Asp Ala Val Glu Val Pro Ala Pro Ala Ala Val Leu Gly
65                  70                  75                  80

Gly Pro Glu Pro Leu Met Gln Ala Thr Ala Trp Leu Asn Ala Tyr Phe
                85                  90                  95

His Gln Pro Glu Ala Ile Glu Glu Phe Pro Val Pro Ala Leu His His
            100                 105                 110

Pro Val Phe Gln Gln Glu Ser Phe Thr Arg Gln Val Leu Trp Lys Leu
        115                 120                 125

Leu Lys Val Val Lys Phe Gly Glu Val Ile Ser Tyr Gln Gln Leu Ala
    130                 135                 140

Ala Leu Ala Gly Asn Pro Ala Ala Thr Ala Ala Val Lys Thr Ala Leu
145                 150                 155                 160

Ser Gly Asn Pro Val Pro Ile Leu Ile Pro Cys His Arg Val Val Ser
                165                 170                 175

Ser Ser Gly Ala Val Gly Gly Tyr Glu Gly Gly Leu Ala Val Lys Glu
            180                 185                 190

Trp Leu Leu Ala His Glu Gly His Arg Leu Gly Lys Pro Gly Leu Gly
        195                 200                 205

Pro Ala Gly Ser Gly Ala Pro His Phe Pro Glu Ile Ser Phe Pro Pro
    210                 215                 220

Lys Pro Asp Ser Asp Tyr Gln Ala Leu Leu Pro Ser Ala Pro Glu Ile
225                 230                 235                 240

Tyr Ser His Leu Ser Pro Thr Lys Pro Asp Tyr Ile Asn Leu Arg Pro
                245                 250                 255
```

Ala Pro

<210> SEQ ID NO 123
<211> LENGTH: 872
<212> TYPE: DNA
<213> ORGANISM: Artificial Sequence
<220> FEATURE:
<223> OTHER INFORMATION: Synthetic polynucleotide - D-SNAP-DCTM (DSC) gene
<220> FEATURE:
<221> NAME/KEY: CDS
<222> LOCATION: (13)..(759)

<400> SEQUENCE: 123

```
gaattcgcca cc atg ggc agc agc aag agc aag tct aga ggc ccg gga ggc      51
              Met Gly Ser Ser Lys Ser Lys Ser Arg Gly Pro Gly Gly
                1               5                  10 agc gct agc atg gac aaa gac tgc gaa atg aag cgc acc acc ctg gat        99
Ser Ala Ser Met Asp Lys Asp Cys Glu Met Lys Arg Thr Thr Leu Asp
 15                  20                  25 agc cct ctg ggc aag ctg gaa ctg tct ggg tgc gaa cag ggc ctg cac       147
Ser Pro Leu Gly Lys Leu Glu Leu Ser Gly Cys Glu Gln Gly Leu His
 30                  35                  40                  45 gag atc aag ctg ctg ggc aaa gga aca tct gcc gcc gac gcc gtg gaa       195
Glu Ile Lys Leu Leu Gly Lys Gly Thr Ser Ala Ala Asp Ala Val Glu
                 50                  55                  60 gtg cct gcc cca gcc gcc gtg ctg ggc gga cca gag cca ctg atg cag       243
Val Pro Ala Pro Ala Ala Val Leu Gly Gly Pro Glu Pro Leu Met Gln
                 65                  70                  75 gcc acc gcc tgg ctc aac gcc tac ttt cac cag cct gag gcc atc gag       291
Ala Thr Ala Trp Leu Asn Ala Tyr Phe His Gln Pro Glu Ala Ile Glu
             80                  85                  90 gag ttc cct gtg cca gcc ctg cac cac cca gtg ttc cag cag gag agc       339
Glu Phe Pro Val Pro Ala Leu His His Pro Val Phe Gln Gln Glu Ser
         95                 100                 105 ttt acc cgc cag gtg ctg tgg aaa ctg ctg aaa gtg gtg aag ttc gga       387
Phe Thr Arg Gln Val Leu Trp Lys Leu Leu Lys Val Val Lys Phe Gly
110                 115                 120                 125 gag gtc atc agc tac cag cag ctg gcc gcc ctg gcc ggc aat ccc gcc       435
Glu Val Ile Ser Tyr Gln Gln Leu Ala Ala Leu Ala Gly Asn Pro Ala
                130                 135                 140 gcc acc gcc gcc gtg aaa acc gcc ctg agc gga aat ccc gtg ccc att       483
Ala Thr Ala Ala Val Lys Thr Ala Leu Ser Gly Asn Pro Val Pro Ile
                145                 150                 155 ctg atc ccc tgc cac cgg gtg gtg tct agc tct ggc gcc gtg ggg ggc       531
Leu Ile Pro Cys His Arg Val Val Ser Ser Ser Gly Ala Val Gly Gly
            160                 165                 170 tac gag ggc ggg ctc gcc gtg aaa gag tgg ctg ctg gcc cac gag ggc       579
Tyr Glu Gly Gly Leu Ala Val Lys Glu Trp Leu Leu Ala His Glu Gly
        175                 180                 185 cac aga ctg ggc aag cct ggg ctg ggt cct gca gga agc ggc gcg ccc       627
His Arg Leu Gly Lys Pro Gly Leu Gly Pro Ala Gly Ser Gly Ala Pro
190                 195                 200                 205 cac ttc cct gaa atc tcc ttc ccc cct aaa ccc gat tct gat tat cag       675
His Phe Pro Glu Ile Ser Phe Pro Pro Lys Pro Asp Ser Asp Tyr Gln
                210                 215                 220 gcc ttg cta cca tcc gcg cca gag atc tac tct cac ctc tcc ccc acc       723
Ala Leu Leu Pro Ser Ala Pro Glu Ile Tyr Ser His Leu Ser Pro Thr
                225                 230                 235 aaa ccc gat tac atc aac ctt cga ccg gcg ccc tag gaccccatg             769
Lys Pro Asp Tyr Ile Asn Leu Arg Pro Ala Pro
                240                 245
```
tttcacgcac cctcaggctg tggtggggca ctggcttagt ggaatagtca gtgtaccatc    829
acaagcctct tcttgctgcc agcaccgagt tcgaagcggc cgc                       872

<210> SEQ ID NO 124
<211> LENGTH: 248
<212> TYPE: PRT
<213> ORGANISM: Artificial Sequence
<220> FEATURE:
<223> OTHER INFORMATION: Synthetic Construct

<400> SEQUENCE: 124

Met Gly Ser Ser Lys Ser Lys Ser Arg Gly Pro Gly Gly Ser Ala Ser
1               5                   10                  15

Met Asp Lys Asp Cys Glu Met Lys Arg Thr Thr Leu Asp Ser Pro Leu
            20                  25                  30

Gly Lys Leu Glu Leu Ser Gly Cys Glu Gln Gly Leu His Glu Ile Lys
        35                  40                  45

Leu Leu Gly Lys Gly Thr Ser Ala Ala Asp Ala Val Glu Val Pro Ala
    50                  55                  60
Pro Ala Ala Val Leu Gly Gly Pro Glu Pro Leu Met Gln Ala Thr Ala
65                  70                  75                  80

Trp Leu Asn Ala Tyr Phe His Gln Pro Glu Ala Ile Glu Glu Phe Pro
                85                  90                  95

Val Pro Ala Leu His His Pro Val Phe Gln Gln Glu Ser Phe Thr Arg
            100                 105                 110

Gln Val Leu Trp Lys Leu Leu Lys Val Val Lys Phe Gly Glu Val Ile
        115                 120                 125

Ser Tyr Gln Gln Leu Ala Ala Leu Ala Gly Asn Pro Ala Ala Thr Ala
    130                 135                 140

Ala Val Lys Thr Ala Leu Ser Gly Asn Pro Val Pro Ile Leu Ile Pro
145                 150                 155                 160

Cys His Arg Val Val Ser Ser Ser Gly Ala Val Gly Gly Tyr Glu Gly
                165                 170                 175

Gly Leu Ala Val Lys Glu Trp Leu Leu Ala His Glu Gly His Arg Leu
            180                 185                 190

Gly Lys Pro Gly Leu Gly Pro Ala Gly Ser Gly Ala Pro His Phe Pro
        195                 200                 205

Glu Ile Ser Phe Pro Pro Lys Pro Asp Ser Asp Tyr Gln Ala Leu Leu
    210                 215                 220

Pro Ser Ala Pro Glu Ile Tyr Ser His Leu Ser Pro Thr Lys Pro Asp
225                 230                 235                 240

Tyr Ile Asn Leu Arg Pro Ala Pro
                245

<210> SEQ ID NO 125
<211> LENGTH: 6
<212> TYPE: PRT
<213> ORGANISM: Artificial Sequence
<220> FEATURE:
<223> OTHER INFORMATION: consensus sequence for membrane-anchoring
      domain (fragment of Src kinase protein)
<220> FEATURE:
<221> NAME/KEY: misc_feature
<222> LOCATION: (3)..(5)
<223> OTHER INFORMATION: Xaa can be any naturally occurring amino acid

<400> SEQUENCE: 125

Met Gly Xaa Xaa Xaa Ser
1               5

```
1               5

<210> SEQ ID NO 126
<211> LENGTH: 6
<212> TYPE: PRT
<213> ORGANISM: Artificial Sequence
<220> FEATURE:
<223> OTHER INFORMATION: consensus sequence for membrane-anchoring
      domain (fragment of Src kinase prootein)
<220> FEATURE:
<221> NAME/KEY: misc_feature
<222> LOCATION: (3)..(5)
<223> OTHER INFORMATION: Xaa can be any naturally occurring amino acid

<400> SEQUENCE: 126

Met Gly Xaa Xaa Xaa Cys
1               5

<210> SEQ ID NO 127
<211> LENGTH: 4
<212> TYPE: PRT
<213> ORGANISM: Artificial Sequence
<220> FEATURE:
<223> OTHER INFORMATION: motif of cytoplasmic vesicle-addressing domain
<220> FEATURE:
<221> NAME/KEY: misc_feature
<222> LOCATION: (2)..(3)
<223> OTHER INFORMATION: Xaa can be any naturally occurring amino acid

<400> SEQUENCE: 127

Tyr Xaa Xaa Leu
1

<210> SEQ ID NO 128
<211> LENGTH: 5
<212> TYPE: PRT
<213> ORGANISM: Artificial Sequence
<220> FEATURE:
<223> OTHER INFORMATION: motif of cytoplasmic vesicle-addressing domain
<220> FEATURE:
<221> NAME/KEY: misc_feature
<222> LOCATION: (3)..(4)
<223> OTHER INFORMATION: Xaa can be any naturally occurring amino acid

<400> SEQUENCE: 128

Asp Tyr Xaa Xaa Leu
1               5

<210> SEQ ID NO 129
<211> LENGTH: 13
<212> TYPE: PRT
<213> ORGANISM: Bovine leukemia virus

<400> SEQUENCE: 129

Lys Cys Leu Thr Ser Arg Leu Leu Lys Leu Leu Arg Gln
1               5                   10

<210> SEQ ID NO 130
<211> LENGTH: 40
<212> TYPE: PRT
<213> ORGANISM: Artificial Sequence
<220> FEATURE:
<223> OTHER INFORMATION: vesicle-addressing motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(8)
```

```
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (38)..(39)
<223> OTHER INFORMATION: Xaa can be any naturally occurring amino acid

<400> SEQUENCE: 130

Pro Xaa Xaa Pro Xaa Xaa Xaa Xaa Pro Xaa Xaa Pro Xaa Xaa Xaa Tyr
1               5                   10                  15

Xaa Xaa Leu Xaa Pro Xaa Xaa Pro Glu Xaa Tyr Xaa Xaa Leu Xaa Pro
            20                  25                  30

Xaa Xaa Pro Asp Tyr Xaa Xaa Leu
        35                  40

<210> SEQ ID NO 131
<211> LENGTH: 45
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (44)..(44)
<223> OTHER INFORMATION: Xaa is any amino acid other than Cys and is a
      non-palmytilable amino acid

<400> SEQUENCE: 131

Ala Pro His Phe Pro Glu Ile Ser Phe Pro Pro Lys Pro Asp Ser Asp
1               5                   10                  15

Tyr Gln Ala Leu Leu Pro Ser Ala Pro Glu Ile Tyr Ser His Leu Ser
            20                  25                  30

Pro Thr Lys Pro Asp Tyr Ile Asn Leu Arg Pro Xaa Pro
        35                  40                  45
```

The invention claimed is:

1. An exosome comprising a first chimeric polypeptide, wherein said first chimeric polypeptide is bound to the inner surface of the membrane of said exosome, without passing through said membrane, wherein said first chimeric polypeptide comprises
   (i) a peptide or polypeptide of interest,
   (ii) a membrane-anchoring domain, which binds the peptide or polypeptide of (i) to the inner surface of the membrane of said exosome, without being inserted into the lipid bilayer, wherein the amino acid sequence of said membrane-anchoring domain is
   a) the sequence of a fragment of a protein of the Src family, wherein said fragment comprises the amino acid sequence M-G-X1-X2-X3-S(SEQ ID NO: 125) or M-G-X1-X2-X3-C(SEQ ID NO: 126), in which X1, X2, and X3 independently designate any amino acid residue, or
   b) a sequence, which is at least 90% identical to said sequence of a), and which still comprises the amino acid sequence M-G-X1-X2-X3-S(SEQ ID NO: 125) or M-G-X1-X2-X3-C(SEQ ID NO: 126), in which X1, X2, and X3 independently designate any amino acid residue,
and
   (iii) an exosome-addressing domain, the amino acid sequence of which is at least 60% identical to the sequence of SEQ ID NO: 8 and with the C-terminal amino acids being PXP wherein X is an amino acid other than C and is a non-palmytilable amino acid, wherein said exosome-addressing domain comprises at least one PSAP (SEQ ID NO: 88) motif and at least one YxxL (SEQ ID NO: 127) or DYxxL (SEQ ID NO: 128) motif, wherein x independently represents any amino acid residue, and
wherein said first chimeric polypeptide does not comprise any transmembrane domain and does not comprise any signal peptide for importation into the endoplasmic reticulum.

2. A therapeutic composition, the active principle of which comprises one or more exosome(s) of claim 1.

3. A method for producing antibodies directed against one or more antigenic peptide(s) or polypeptide(s), wherein said method comprises:
   a) administering exosomes of claim 1 to a non-human animal to induce the production of antibodies in said non-human animal, wherein the peptide or polypeptide of interest of the first chimeric polypeptide of said exosomes of claim 1 comprises said antigenic peptide(s) or polypeptide(s); and
   b) recovering from said non-human animal antibodies, which specifically bind to said antigenic peptide(s) or polypeptide(s).

4. A method for producing monoclonal antibody(ies) directed against one or more antigenic peptide(s) or polypeptide(s), wherein said method comprises
   a) fusing spleen cells with myeloma cells to produce hybridomas, wherein said spleen cells have been collected from an animal, to which exosomes of claim 1 have been administered, wherein the peptide or polypeptide of interest of the first chimeric polypeptide of said exosomes of claim 1 comprises said antigenic peptide(s) or polypeptide(s);
   b) culturing the hybridomas produced at step a) to produce monoclonal antibodies; and
   c) recovering monoclonal antibody(ies), which is(are) directed against said antigenic peptide(s) or polypeptide(s), among the monoclonal antibodies produced at step b).

5. The exosome of claim 1, which, in addition to said first chimeric polypeptide, further comprises a second chimeric polypeptide, wherein said second chimeric polypeptide passes through the membrane of said exosome, and wherein said second chimeric polypeptide comprises
   (i) a peptide or polypeptide of interest, wherein said peptide or polypeptide of interest is identical to, or different from, the peptide or polypeptide of interest of said first chimeric polypeptide;
   (ii) a transmembrane domain; and
   (iii) an exosome-addressing domain, the amino acid sequence of which is at least 60% identical to the sequence of SEQ ID NO: 8 and with the C-terminal amino acids being PXP wherein X is an amino acid other than C and is a non-palmytilable amino acid, wherein said exosome-addressing domain comprises at least one PSAP (SEQ ID NO: 88) motif and at least one YxxL (SEQ ID NO: 127) or DYxxL (SEQ ID NO: 128) motif, wherein x independently represents any amino acid residue.

6. A method for in vitro screening molecules for their capacity to interact with a peptide or a polypeptide of interest, wherein said method comprises
   a) bringing exosomes of claim 5 into contact with said molecules, wherein said peptide or polypeptide of interest is comprised in the second chimeric polypeptide of said exosomes of claim 5 and is exposed on the outside of said membrane vesicle; and
   b) detecting molecules, which interact with said peptide or polypeptide of interest exposed on the outside of said membrane exosome, among the molecules contacted at step a).

7. The exosome of claim 1, which, in addition to said first chimeric polypeptide, further comprises at least one second chimeric polypeptide, wherein said second chimeric polypeptide passes through the membrane of said exosome, and wherein said at least one second chimeric polypeptide comprises
   (i) a peptide or polypeptide of interest, wherein said peptide or polypeptide of interest is identical to, or different from, the peptide or polypeptide of interest of said first chimeric polypeptide;
   (ii) a transmembrane domain; and
   (iii) an exosome-addressing domain, the amino acid sequence of which is at least 60% identical to the sequence of SEQ ID NO: 8 and with the C-terminal amino acids being PXP wherein X is an amino acid other than C and is a non-palmytilable amino acid, wherein said exosome-addressing domain comprises at least one PSAP (SEQ ID NO: 88) motif and at least one YxxL (SEQ ID NO: 127) or DYxxL (SEQ ID NO: 128) motif, wherein x independently represents any amino acid residue; and
   wherein said peptide or polypeptide of interest of said second chimeric polypeptide is exposed, in part or in its entirety, to the outside of said membrane exosome.

8. The exosome claim 1, wherein said domains (i) to (iii) are in the following N-term to C-term order: (ii)-(i)-(iii) or (ii)-(iii)-(i); or
   wherein said domain (i) consists of two non-contiguous portions, wherein a first of said two non-contiguous portions is in N-term of said domains (ii) and (iii), and wherein the second of said two non-contiguous portions is in C-term of said domains (ii) and (iii).

9. The exosome of claim 1, wherein said exosome-addressing domain of (iii) comprises two or three YxxL (SEQ ID NO: 127) motifs, wherein x represents any residue.

10. The exosome of claim 1, wherein said exosome-addressing domain of (iii) comprises at least one YxxL or DYxxL motif selected from YINL, YSHL and DYINL.

11. The exosome of claim 1, wherein said membrane-anchoring domain of (ii) binds said peptide or polypeptide of (i) to the inner surface of the membrane of said exosome, via a lipid, a fatty acid, a myristic acid, a palmitic acid, a geranyl-geranyl, a farnesyl or a FYVE domain.

12. The exosome of claim 1, wherein, in said M-G-X1-X2-X3-S(SEQ ID NO: 125) or M-G-X1-X2-X3-C(SEQ ID NO: 126) sequence,
X1 is C, S or L; and/or
X2 is S, I, V, M or L; and/or
X3 is K, Q, H, F, C or S.

13. The exosome of claim 1, wherein said membrane-anchoring domain of (ii) comprises a plurality of basic amino acid residues.

14. The exosome of claim 1, wherein said protein of the Src family of claim 1 (ii) a) is the Src, Yes, Lyn, Fyn, Lck, Blk, Fgr, Hck or Yrk protein.

15. The exosome of claim 1, wherein said fragment of claim 1 (ii) a), which comprises the amino acid sequence M-G-X1-X2-X3-S(SEQ ID NO: 125) or M-G-X1-X2-X3-C(SEQ ID NO: 126), comprises or consists of the amino acid sequence M-G-S-S-K-S-K-P-K-D-P-S-Q-R-R-R (SEQ ID NO: 104) or the amino acid sequence G-S-S-K-S-K-P-K-D-P-S-Q-R-R-R-K-S-R-G-P-G-G (SEQ ID NO: 105).

16. The exosome of claim 1, wherein said first chimeric polypeptide further comprises at least one linker linking two of said (i)-(iii) domains together and wherein said linker is a peptide or a polypeptide.

17. The exosome of claim 1, wherein said exosome-addressing domain of (iii) comprises the sequence Pxx-PxxxxPxxxPxxxYxxLxPxxPExYxxLxPxxPDYxxL (SEQ ID NO: 130).

18. The exosome of claim 1, wherein the sequence of said exosome-addressing domain of (iii) consists of the sequence of SEQ ID NO: 12.

19. The exosome of claim 1, wherein said exosome-addressing domain of (iii) does not comprise the sequence KCLTSRLLKLLRQ (SEQ ID NO: 129).

20. The exosome of claim 1, wherein the peptide or polypeptide of interest of said first chimeric polypeptide comprises one or more domain(s) of a cytosolic protein, or one or more fragment(s) of said cytosolic protein domain(s).

21. The exosome of claim 1, wherein the peptide or the polypeptide of interest of said first chimeric polypeptide comprises or consists of a fragment from a protein of a pathogenic organism, a pathogenic agent, a tumoral antigen, a cytoplasmic antigen, or a ligand receptor.

22. A therapeutic composition, the active principle of which comprises one or more exosome(s) of claim 1.

23. A therapeutic composition, the active principle of which comprises one or more exosome(s) of claim 7.

24. The exosome of claim 1, wherein said fragment of (ii) a) comprises the amino acid sequence M-G-X1-X2-X3-C (SEQ ID NO: 126), in which X1, X2, and X3 independently designate any amino acid residue, and wherein said sequence of (ii) b) is at least 60% identical to said sequence of (ii) a) and still comprises the amino acid sequence M-G-X1-X2-X3-C(SEQ ID NO: 126), in which X1, X2, and X3 independently designate any amino acid residue.

25. The exosome of claim 1, wherein the peptide or polypeptide of interest of said first chimeric polypeptide comprises one or more domain(s) of a nuclear protein, or one or more fragment(s) of said nuclear protein domain(s).

26. The exosome of claim 1, wherein said non-palmytilable amino acid is the amino acid A.

27. The exosome of claim 5, wherein said non-palmytilable amino acid is the amino acid A.

28. The exosome of claim 7, wherein said non-palmytilable amino acid is the amino acid A.

29. The exosome of claim 1, wherein the amino acid sequence of said exosome-addressing domain is at least 70% or 80% identical to SEQ ID NO: 8 and with the C-terminal amino acids being PXP wherein X is an amino acid other than C and is a non-palmytilable amino acid.

30. The exosome of claim 1, wherein the amino acid sequence of said exosome-addressing domain is at least 90% or 95% identical to SEQ ID NO: 8 and with the C-terminal amino acids being PXP wherein X is an amino acid other than C and is a non-palmytilable amino acid.

31. The exosome of claim 1, which, in addition to said first chimeric polypeptide, further comprises at least one second chimeric polypeptide, wherein said second chimeric polypeptide passes through the membrane of said exosome.

* * * * *